(12) United States Patent
Mikheev et al.

(10) Patent No.: US 9,959,683 B2
(45) Date of Patent: May 1, 2018

(54) METHOD OF DETERMINING THE POSITION OF AN OBJECT USING PROJECTIONS OF MARKERS OR STRUTS

(71) Applicants: AMEI TECHNOLOGIES, INC., Wilmington, DE (US); TEXAS SCOTTISH RITE HOSPITAL FOR CHILDREN, Dallas, TX (US)

(72) Inventors: Konstantin Evgenevich Mikheev, Sarov (RU); Petr Stanislavovich Vvedenskiy, Nizhniy Novgorod (RU); Alexander Alexandrovich Morenko, Sarov (RU); Dmitry Alexandrovich Sivachev, Sarov (RU); Mikhail Samchukov, Dallas, TX (US); Alexander Cherkashin, Dallas, TX (US)

(73) Assignees: Texas Scottish Rite Hospital for Children, Dallas, TX (US); AMEI Technologies, Inc., Wilmington, DE (US)

( * ) Notice: Subject to any disclaimer, the term of this patent is extended or adjusted under 35 U.S.C. 154(b) by 0 days. days.

(21) Appl. No.: 14/777,417

(22) PCT Filed: Mar. 15, 2013

(86) PCT No.: PCT/RU2013/000203
§ 371 (c)(1),
(2) Date: Sep. 15, 2015

(87) PCT Pub. No.: WO2014/142703
PCT Pub. Date: Sep. 18, 2014

(65) Prior Publication Data
US 2016/0042571 A1 Feb. 11, 2016

(51) Int. Cl.
*G06T 19/20* (2011.01)
*G06T 7/80* (2017.01)

(52) U.S. Cl.
CPC ............ *G06T 19/20* (2013.01); *G06T 7/85* (2017.01); *G06T 2207/10116* (2013.01); *G06T 2219/2004* (2013.01)

(58) Field of Classification Search
USPC ............... 345/419; 382/128, 132; 600/426
See application file for complete search history.

(56) References Cited

U.S. PATENT DOCUMENTS 7,117,027 B2 * 10/2006 Zheng ................ A61B 6/4441
378/196
7,756,244 B2 * 7/2010 Mostafavi ............ A61B 6/032
378/20

(Continued)

OTHER PUBLICATIONS

Ghanem, R.N., et al., "Heart-Surface Reconstruction and ECG Electrodes Localization Using Fluoroscopy, Epipolar Geometry and Stereovision: Application to Noninvasive Imaging of Cardiac Electrical Activity," IEEE Transactions on Medical Imaging, vol. 22, No. 10, (Oct. 2003), 12 pages.

(Continued)

*Primary Examiner* — Kimbinh T Nguyen
(74) *Attorney, Agent, or Firm* — Baker & McKenzie LLP

(57) ABSTRACT

A 3-D model of a body part is created by using an object comprising markers, fixation members, and struts. The method involves first and second roentgenograms of the body part and the object disposed between an x-ray source and an x-ray imager. It then determines first and second sets of distances between projections of the markers or the struts, and determines first and second 3-D positions of the x-ray source and of the object with respect to the x-ray imager using predetermined distances between the markers or struts and the first and second sets of distances between their (Continued)

projections. The method then aligns the first and second 3-D object projections in a 3-D reference frame using the 3-D positions of the markers or struts with respect to the x-ray imager in the two orientations. The method creates the 3-D model of the object based on the 3-D object projections.

28 Claims, 22 Drawing Sheets

(56) References Cited

U.S. PATENT DOCUMENTS

| | | | | |
|---|---|---|---|---|
| 7,881,768 | B2* | 2/2011 | Lang | A61B 5/055 600/407 |
| 8,104,958 | B2* | 1/2012 | Weiser | A61B 6/583 378/162 |
| 8,265,770 | B2* | 9/2012 | Toy | A61N 1/37211 607/60 |
| 8,326,403 | B2* | 12/2012 | Pescatore | A61B 6/02 378/205 |
| 8,333,766 | B2* | 12/2012 | Edelhauser | A61B 17/62 606/55 |
| 2007/0211849 | A1* | 9/2007 | Movassaghi | G06T 11/005 378/26 |
| 2011/0071389 | A1* | 3/2011 | Simon | A61B 6/12 600/426 |
| 2011/0103676 | A1* | 5/2011 | Mullaney | A61B 17/6458 382/132 |
| 2011/0262024 | A1* | 10/2011 | Bulitta | A61B 6/583 382/132 |
| 2011/0313418 | A1* | 12/2011 | Nikonovas | A61B 17/62 606/56 |

OTHER PUBLICATIONS

Li, Y., et al., "Distortion Correction and Geometric Calibration for X-Ray Angiography System," IEEE Transactions on Nuclear Science, vol. 56, No. 3, (Jun. 2009), 12 pages.

Selby, B.P., et al., "Patient positioning with X-ray detector self-calibration for image guided therapy," Australas Phys. Eng. Sci. Med., vol. 34, No. 3, (2011), 10 pages.

Canero, C., et al., "Predictive (Un)distortion Model and 3-D Reconstruction by Biplane Snakes, IEEE Transactions on Medical Imaging," vol. 21, No. 9, (Sep. 2002), 14 pages.

Zheng, G., et al., "A 2D/3D correspondence building method for reconstruction of a patient-specific 3D bone surface model using point distribution models and calibrated X-ray images," Medical Image Analysis, vol. 13, No. 6, (2009), 17 pages.

Yang, G., et al., "Novel Approach for 3-D Reconstruction of Coronary Arteries from Two Uncalibrated Angiographic Images," IEEE Transactions on Image Processing, vol. 18, No. 7, (Jul. 2009), 10 pages.

International Search Report, PCT/RU2013/000203, dated Jan. 29, 2014, 4 pages.

Written Opinion of the International Searching Authority, PCT/RU2013/000203, dated Jan. 29, 2014, 6 pagtes.

* cited by examiner

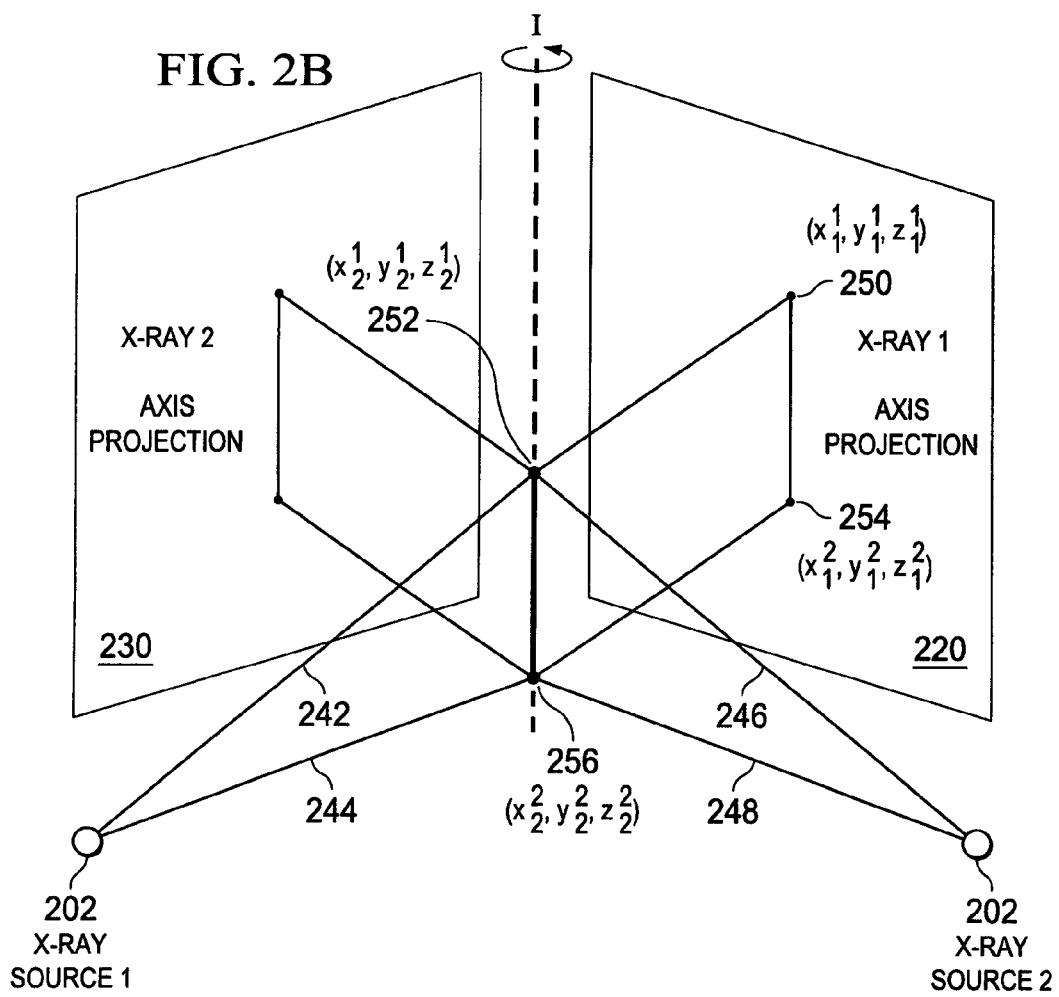

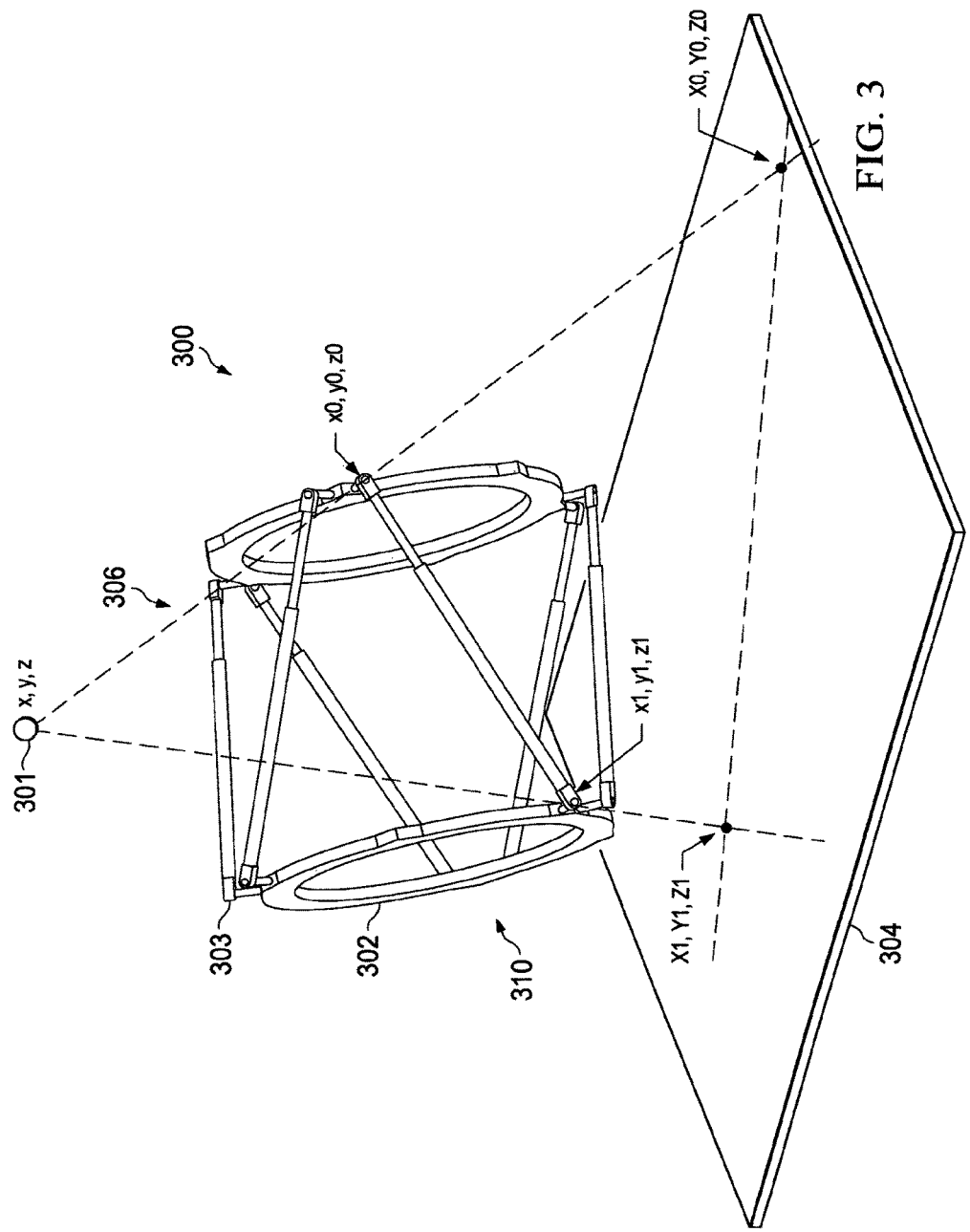

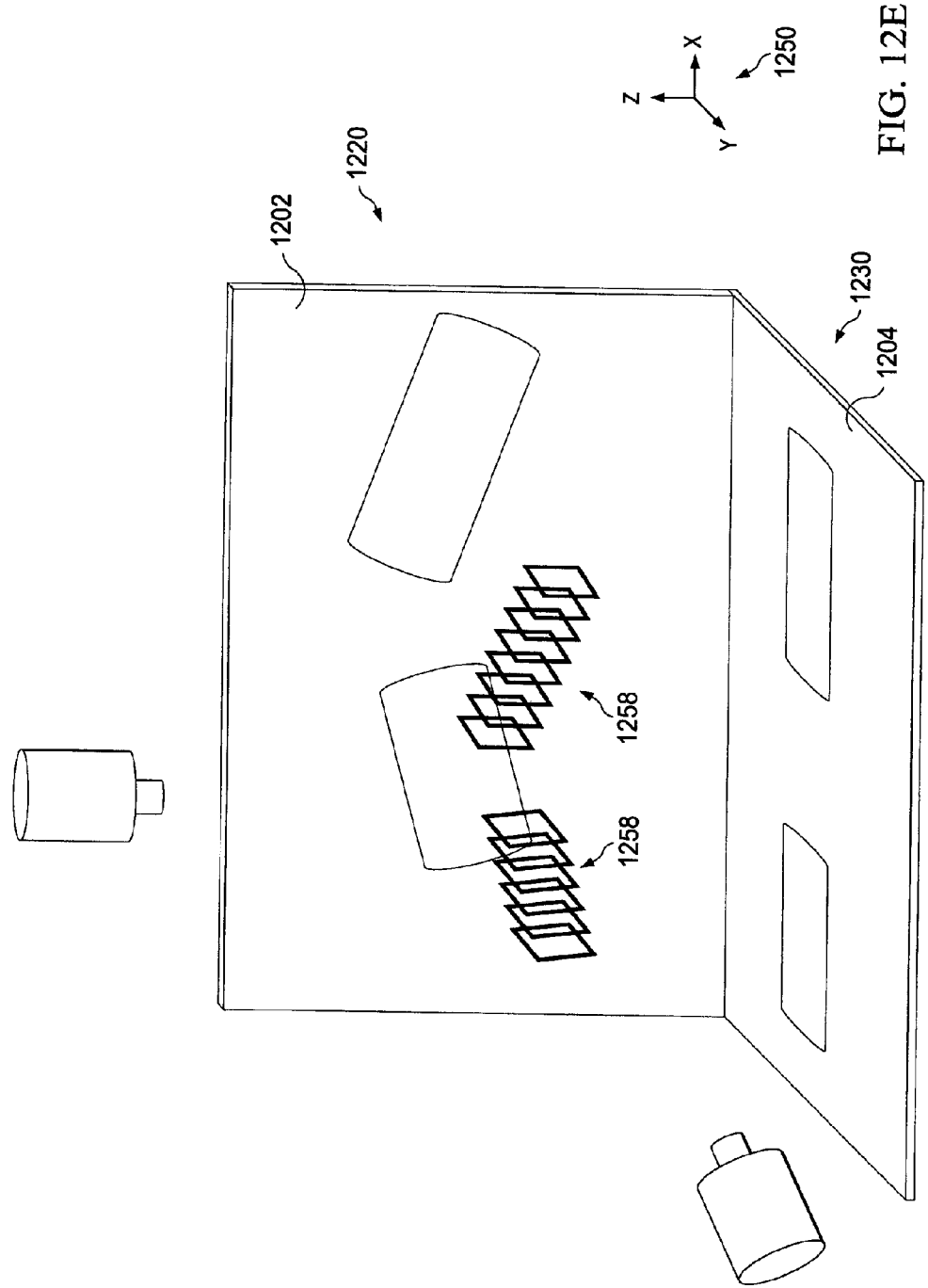

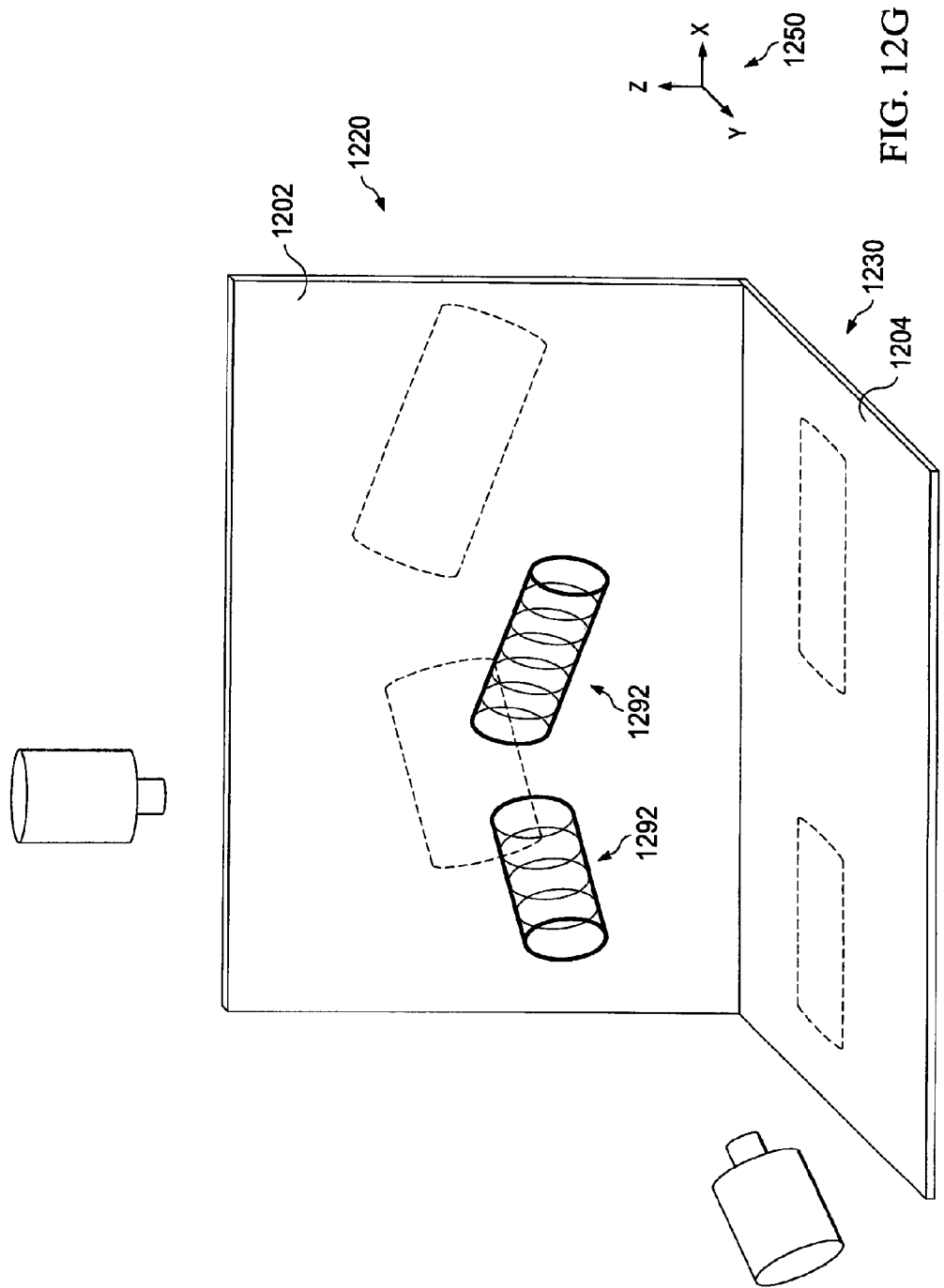

US 9,959,683 B2

METHOD OF DETERMINING THE POSITION OF AN OBJECT USING PROJECTIONS OF MARKERS OR STRUTS

TECHNICAL FIELD

The present disclosure relates in general to the field of roentgenography, and more specifically, to creating three-dimensional (3-D) models of objects in space based on two-dimensional (2-D) roentgenograms.

BACKGROUND

Modeling an object in 3-D space has a number of useful applications. A 3-D model of objects may allow one to more easily visualize and analyze orientations of the objects relative to each other. This aspect of modeling is particularly useful in orthopedics, or more specifically, in analyzing bone deformities. Computed tomography (CT) is one conventional technique that has been used in the field of orthopedics to generate 3-D representation of human tissues. Another conventional technique involves visualizing and analyzing bone deformities with the aid of 2-D roentgenograms. First, radiographic images of deformed bone segments are obtained in orthogonal views. Subsequently, the deformities can be analyzed by creating 2-D linear representations of the imaged bone segments and projecting such linear representations in the plane of the deformity. Alternatively, the outlines of the deformed bone segments in the 2-D roentgenograms may be manually determined and extrapolated to build a 3-D model of the deformed bone segments.

SUMMARY

The present disclosure provides a method of creating a 3-D model of a body part, the body part being coupled to an object, the object comprising a plurality of markers at predetermined distances along the object. In an embodiment, the method comprises: 1) receiving a first roentgenogram of the body part and the object disposed between an x-ray source and an x-ray imager, wherein the first roentgenogram includes an image of the body part, the object, and the plurality of markers; 2) receiving a second roentgenogram of the body part and the object disposed between the x-ray source and the x-ray imager, wherein the second roentgenogram includes an image of the body part, the object, and the plurality of markers; 3) determining a first set of distances between projections of the plurality of markers on the first roentgenogram; 4) determining a first 3-D position of the x-ray source and a first 3-D position of the object with respect to the x-ray imager using the predetermined distances between the plurality of markers and the first set of distances between the projections of the plurality of markers on the first roentgenogram; 4) determining a second set of distances between projections of the plurality of markers on the second roentgenogram; 5) determining a second 3-D position of the x-ray source and a second 3-D position of the object with respect to the x-ray imager using the predetermined distances between the plurality of markers and the second set of distances between the projections of the plurality of markers on the second roentgenogram; and 6) aligning the first and second 3-D object projections in a 3-D reference frame using the 3-D positions of the plurality of markers with respect to the x-ray imager in the first and second orientations; and 7) creating a 3-D model of the imaged object in the 3-D reference frame based on the first and second 3-D object projections. In an embodiment, the plurality of markers comprises a plurality of joints where a plurality of struts are connected to at least one ring. In an embodiment, the object is an orthopedic fixator. In an embodiment, the plurality of markers comprises five markers and 3-D positions of the x-ray source and of the object are determined by mathematical relationships. In other embodiments, the plurality of markers comprises four markers and 3-D positions of the x-ray source and of the object are determined by mathematical relationships. Another embodiment provides a method of creating a 3-D model of an object, the object being coupled to an object, the object comprising a plurality of struts with predetermined lengths that are each connected to at least two fixation members with predetermined dimensions, the method comprising: 1) receiving a first roentgenogram of the object disposed between an x-ray source and an x-ray imager, wherein the first roentgenogram includes an image of the object and the plurality of struts with predetermined lengths that are each connected to the at least two fixation members at two connection points, wherein the distances between the two connection points are predetermined; 2) receiving a second roentgenogram of the object disposed between the x-ray source and the x-ray imager, wherein the second roentgenogram includes an image of the object and the plurality of struts with predetermined lengths that are each connected to the at least two fixation members at two connection points, wherein the distances between the two connection points are predetermined; 3) determining a first set of projections of longitudinal axes of the plurality of struts on the first roentgenogram; 4) determining a first 3-D position of the x-ray source and a first 3-D position of the object with respect to the x-ray imager using the predetermined distances between the connection points of the plurality of struts and the first set of the projections of the longitudinal axes of the plurality of struts on the first roentgenogram; 5) determining a second set of projections of longitudinal axes of the plurality of struts on the second roentgenogram; 6) determining a second 3-D position of the x-ray source and a second 3-D position of the object with respect to the x-ray imager using the predetermined distances between the connection points of the plurality of struts and the second set of the projections of the longitudinal axes of the plurality of struts on the second roentgenogram; 7) aligning the first and second 3-D object projections in a 3-D reference frame using the 3-D positions of the plurality of struts with respect to the x-ray imager in the first and second orientations; and 8) creating a 3-D model of the imaged object in the 3-D reference frame based on the first and second 3-D object projections. In an embodiment, the object is an orthopedic fixator. In an embodiment, the plurality of struts comprises five struts and the 3-D positions of the x-ray source and of the object are determined by mathematical relationships. In other embodiments, the plurality of struts comprises four struts and the 3-D positions of the x-ray source and of the object are determined by mathematical relationships.

In an embodiment, the method comprises identifying a first body part outline of the imaged body part in the first roentgenogram, identifying a second body part outline of the imaged body part in the second roentgenogram, preparing a first 3-D body part projection from the first body part outline to the first 3-D position of the x-ray source, preparing a second 3-D body part projection from the second body part outline to the second 3-D position of the x-ray source, and creating a 3-D model of the imaged body part in the 3-D reference frame based on the first and second body part projections. In another embodiment, the method further comprises identifying a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation, identifying one or more intersection planes passing through the tilt axis and through the first and second 3-D projections of the imaged body part in the 3-D reference frame, for each of the one or more intersection planes, performing the following steps, a) through c): a) identifying one or more intersection points between the first and second 3-D body part projections, and said intersection plane in the 3-D reference frame; b) preparing one or more polygons connecting the intersection points in said intersection plane; c) preparing one or more closed curves within the each of the one or more polygons, wherein the one or more closed curves corresponds to a cross-sectional view of the imaged body part in said intersection plane, and preparing a surface in the 3-D reference frame that connects each of the closed curves to form a 3-D model of the imaged body part.

BRIEF DESCRIPTION OF THE DRAWINGS

For a more complete understanding of the present disclosure and its advantages, reference is now made to the following description taken in conjunction with the accompanying drawings, in which like reference numbers indicate like features, and:

FIG. 2B is another perspective view of the imaging system and the object in the first orientation and the second orientation, in accordance with the present disclosure;

FIG. 3 is a perspective view of an imaging system and an object with markers in an orientation, in accordance with the present disclosure;

FIG. 12E is a schematic diagram illustrating a plurality of polygons connecting the intersection points in the intersection plane shown in FIG. 12D, in accordance with the present disclosure;

FIG. 12G is a schematic diagram illustrating a surface that connects each of the closed curves shown in FIG. 12F, in accordance with the present disclosure;

DETAILED DESCRIPTION

Figure 1A:
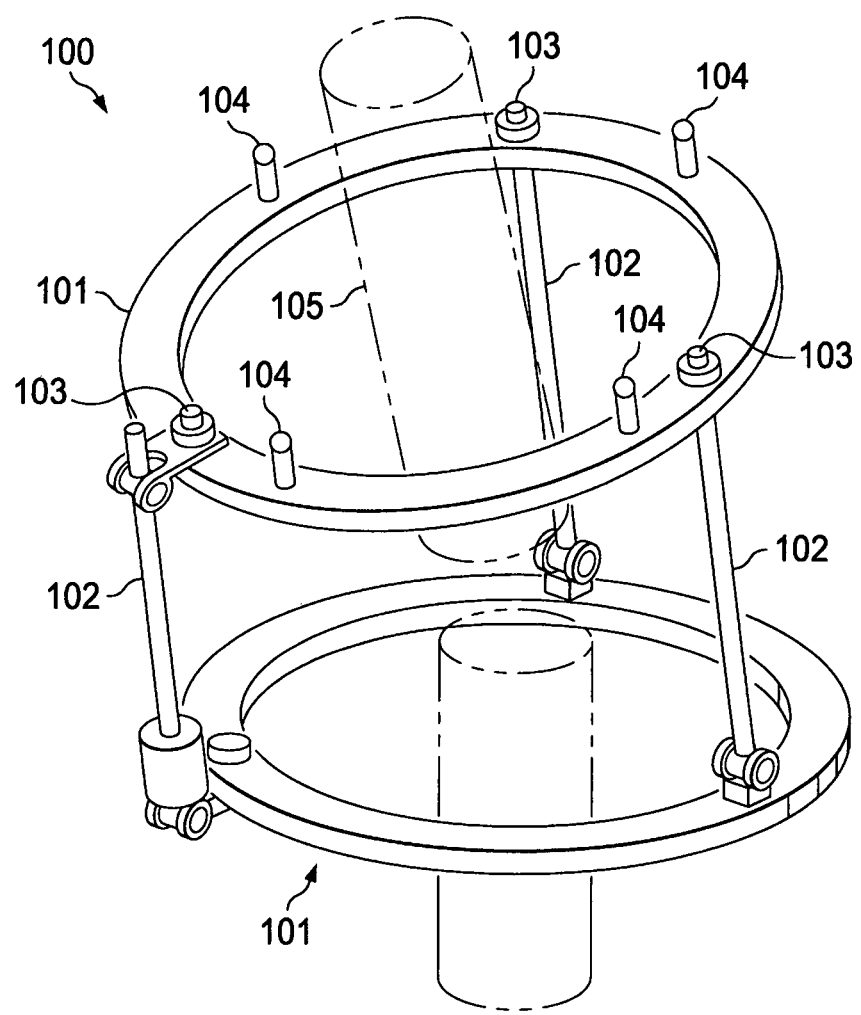
FIG. 1A is a perspective view of an embodiment of an orthopedic fixator.

Conventional techniques for generating 3-D models have many shortcomings. A CT scan generates a set of cross-sectional images that can be combined to produce a 3-D representation of human tissues. The use of CT scans in orthopedic applications, however, may not be practical due to several limitations. During a CT scan, the patient is subject to a relatively large amount of radiation, and repeated use of CT scan can expose the patient to excessive radiation and present health risks. Furthermore, a CT scan is relatively expensive, and is not suitable to image metals, which can cause undesirable distortions. Moreover, the patient is required to remain still during the CT scan, and anesthesia may be required if the patient is a young child. The use of anesthesia, however, increases the cost of treatment and may present additional health risks.

Another conventional technique involves manually determining the outlines of the deformed bone segments in 2-D roentgenograms and extrapolating the 2-D outlines to build a 3-D model of the deformed bone segments. A variety of factors, however, can adversely affect the accuracy of the models created using such a technique. First, projecting linear representations of deformed bone segments do not account for the girth of the bone segments in 3-D space and may cause a physician to prescribe treatments that do not sufficiently correct the bone deformities. Moreover, models created by conventional techniques are based on the assumption that roentgenograms were taken at orthogonal positions, and the accuracy of the model is adversely affected when this is not the case. Although a technician can be trained to estimate orthogonal positions for taking the roentgenograms, minor human errors are inevitable and thus render the models generated by conventional techniques inaccurate. Furthermore, due to the magnification effect of x-rays traveling from an x-ray source to an imager, the object in the roentgenograms appears larger than its actual size. To account for the magnification effect, a reference marker(s) of known dimensions has to be precisely disposed on the object proximate to the region of interest, and the known dimensions of the reference marker is used to determine and account for the magnification effect. Again, the inevitable human imprecision in the placement of the reference marker can lead to inaccuracy.

Due to the above described errors in conventional techniques, the linear and angular parameters obtained are projections rather than true parameters. Projections do not correspond to the true size or shape of objects; they are distorted relative to the true shape of the object. Such techniques are not adequate to accurately determine the coordinates of the points on a chosen object in 3-D space, and in orthopedic applications, such methods are not adequate to accurately calculate the desired distraction, compression, displacement, or other movement of tissue segments.

The present disclosure provides techniques for creating a 3-D model of an object using roentgenograms. From the present disclosure, one of ordinary skill in the art will appreciate that the techniques of the present disclosure may obviate the need to use a precisely placed marker to account for the magnification effect of x-rays. The techniques of the present disclosure also may not require roentgenograms taken at orthogonal positions and may be suitable for roentgenograms taken at various relative orientations. Furthermore, the techniques of the present disclosure may not require use of markers placed on imagers when taking roentgenograms. And the techniques of the present disclosure may also obviate the need to use markers with fiducials.

Embodiments of the present disclosure enable accurate 3-D modeling of objects based on 2-D roentgenograms. These embodiments may determine the position of body parts such as bones by using an object with a known geometry. An embodiment of the object may be an external fixator comprising fixation members, struts, and/or markers. FIG. 1A is an embodiment of the external fixator 100 (circular fixator) that comprises two fixation members 101, three struts 102, and six markers 103, wherein the six markers 103 are points where the two fixation members 101 connect with the three struts 102. Other embodiments may have markers placed in different parts of the external fixator 100. The external fixator 100 may also use additional markers 104 that are attached on the fixation members 101. The external fixator 100 surrounds body parts 105 and may be used to immobilize the body parts 105 to allow their fractures to heal. The fixation members 101 are rings in this embodiment, but other embodiments may have fixation members 101 that are shaped like a hexagon, rectangle, pentagon, or other suitable shapes. Furthermore, while this embodiment employs the three struts 102, other embodiments may employ any suitable number of struts, such as four, five, or six struts.

Figure 1B:
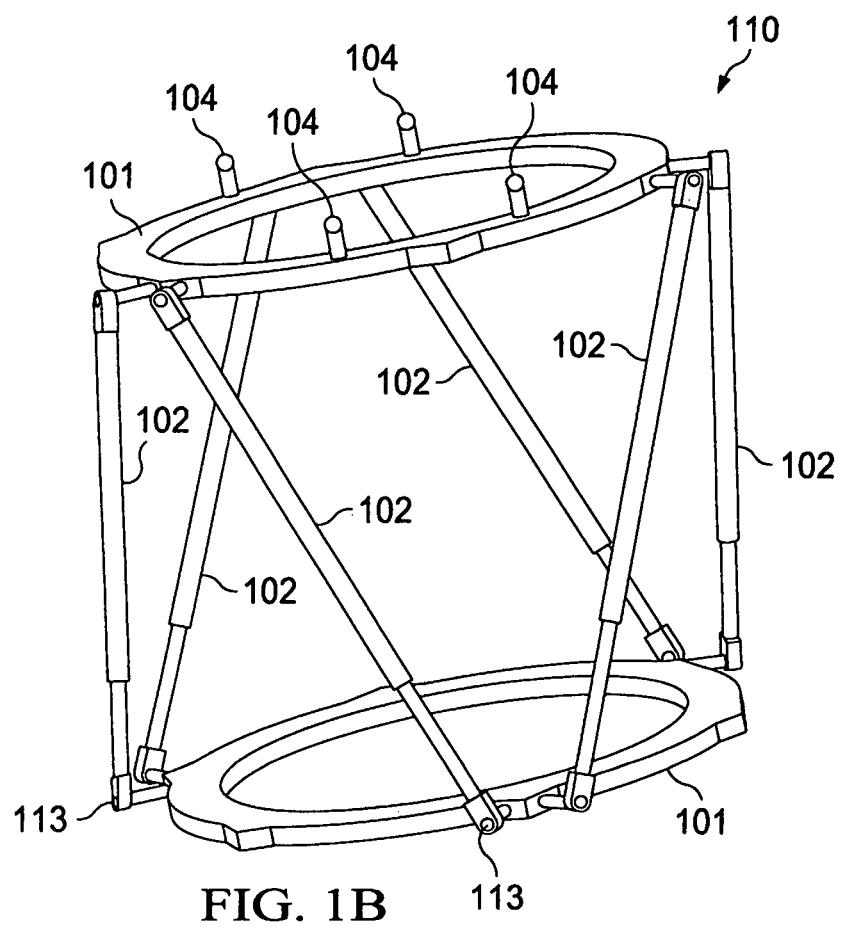
FIG. 1B is a perspective view of another embodiment of an orthopedic fixator.

FIG. 1B is another embodiment of the external fixator 110 that comprises two fixation members 101, six struts 102, and twelve markers 113, wherein the twelve markers are placed where the two fixation members 101 connect with the six struts 102. Once again, other embodiments may have additional markers 104 placed on different parts of the fixation members 101. It is to be appreciated that the embodiments illustrated in FIGS. 1A-1B are merely exemplary, and may be modified according to various design factors disclosed herein or known in the art.

The present disclosure enables the 3-D modeling of a body part by using mathematical models involving the known geometry of an object, such as an external fixator, and its projections on 2-D roentgenograms to derive the positions of the x-ray source, the body parts, and the objects in space. By determining the position of the body parts in space, a physician or other medical staff members may adjust the object, such as an external fixator, for optimal immobilization of bones being treated. They may also use the known positions of the body parts of other medical purposes.

Certain embodiments employ mathematical models that use a plurality of markers to produce the 3-D modeling of objects. In an embodiment, the plurality of markers may further include fiducials. But the plurality of markers is not limited to the markers where the struts meet the fixation members or the markers with fiducials. Furthermore, the plurality of markers may comprise five markers or four markers.

Other embodiments may employ mathematical models that use a plurality of struts instead of the plurality of markers to produce the 3-D modeling of objects. In an embodiment, the plurality of struts may comprise struts that are connected to the fixation members, wherein the plurality of struts may comprise five struts or four struts.

Using Projections of Markers

Figure 2A:
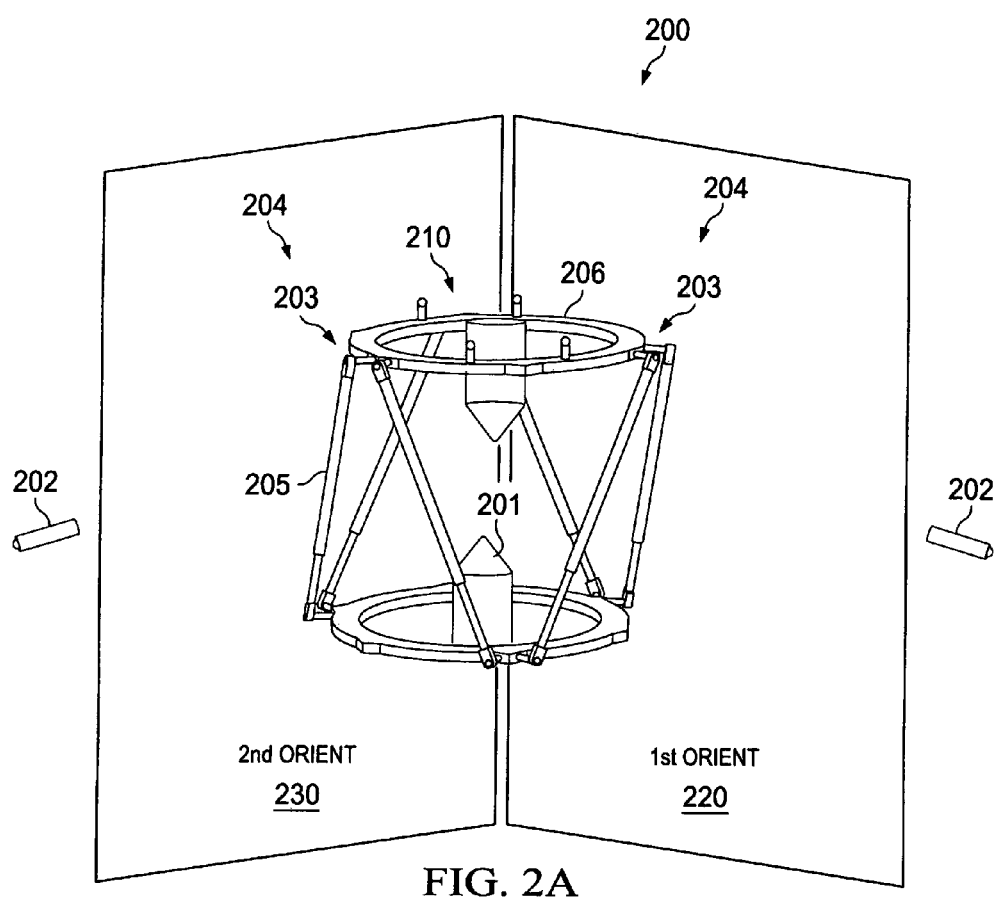
FIG. 2A is a perspective view of an imaging system and an object in a first orientation and a second orientation, in accordance with the present disclosure.

An embodiment of the techniques disclosed herein comprises receiving first and second roentgenograms of a body part and an object disposed between an x-ray source and an imager. The body part is coupled to the object. FIG. 2A is a schematic diagram operable to obtain the first and second roentgenograms in first and second orientations 220, 230, respectively. To obtain the first and second roentgenograms, a body part 201 surrounded by an object 210 is placed between an x-ray source 202 and an imager 204. The object 210 may be an orthopedic fixator, or more specifically a hexapod as shown in FIG. 2A. The object 210 comprises a plurality of markers 203 at predetermined distances along the object 210. To generate the first roentgenogram, the body part 201 surrounded by the object 210, the x-ray source 202, and the imager 204 are in the first orientation 220 relative to each other. The second roentgenogram may be generated by either rotating the body part 201 surrounded by the object 210 to a new second orientation 230 with respect to the x-ray source 202 and the imager 204, or as shown in FIG. 2A, by rotating the x-ray source 202 and the imager 204 to the new second orientation 230 about the body part 201. The first roentgenogram therefore includes an image of the body part 201, the object 210, and the plurality of markers 203 in the first orientation 220. Similarly, the second roentgenogram includes an image of the body part 201, the object 210, and the plurality of markers 203 in the second orientation 230. In the present embodiment, the markers 203 are where struts 205 connect with the fixation members 206, but in other embodiments, the markers 203 may be placed on other parts of the object. The fixation members 206 may be configured as rings or other suitable shapes.

The present embodiment determines a first set of projections of the plurality of markers 203 as depicted on an x-ray imager 204 of the first roentgenogram and a second set of projections of the plurality of markers 203 as depicted on an x-ray imager 204 of the second roentgenogram. FIG. 2B illustrates determining projections of two markers as depicted on the first roentgenogram 220 and as depicted on the second roentgenogram 230. The present embodiment may then determine a first 3-D position of the x-ray source 202 and a first 3-D position of the object 210 with respect to the x-ray imager using the predetermined distances between the plurality of markers and the first set of projections of the plurality of markers as depicted on the first roentgenogram 220. Similarly, the technique may then determine a second 3-D position of the x-ray source 202 and a second 3-D position of the object 210 with respect to the x-ray imager using the predetermined distances between the plurality of markers and the second set of projections of the plurality of markers on the second roentgenogram 230. In an embodiment, the first and second sets of projections of the plurality of markers may more specifically be projections of distances between the plurality of markers on the first and second roentgenograms, respectively. Various mathematical models may be employed for determining the first and second 3-D positions of the x-ray source 202 and of the object. These models will be described in greater detail later.

Once the first and second 3-D positions of the x-ray source and of the object are determined, the technique may then align the first and second 3-D object projections in a 3-D reference frame using the 3-D positions of the plurality of markers with respect to the x-ray imager in the first and second orientations. The embodiment may then create a 3-D model of the imaged body part in the 3-D reference frame based on the first and second 3-D object projections. Another embodiment may create a 3-D model of the object 210 alone or in addition to the 3-D model of the imaged body part.

Model 1

In an embodiment of the techniques disclosed herein, the plurality of markers may comprise five markers associated with an object. FIG. 3 depicts an object 310, an orthopedic fixator in this case, comprising two fixation members 302 and at least five markers 303 in an orientation. The at least five markers 303 are where struts 306 meet the fixation members 302. In other embodiments, the at least five markers 303 may be placed in different parts of the object 310. In the present embodiment, first 3-D positions of the x-ray source 301 and of the object 310 may be determined by using a mathematical model discussed below, in which it is assumed that (x,y,z) are coordinates of the x-ray source 301, (x0,y0,z0) through (x4,y4,z4) are coordinates of the five markers 303, (X0,Y0,Z0) through (X4,Y4,Z4) are coordinates of a first set of projections of the five markers 303 on the first roentgenogram, and l01, l02, l03, l04, l12, l13, l14, l23, l24, l34 are predetermined distances between the five markers 303. There are thus 18 unknown parameters, which require a system with 18 equations to determine the positions of the x-ray source 301 and of the object 310.

The three points (x, y, z), (xi, yi, zi), and (Xi, Yi, Zi) are situated on the same line passing from the x-ray source 301, to the marker 303, and then to the imager 304. The equation for this line may thus be expressed as:

$$\frac{x-xi}{Xi-xi} = \frac{y-yi}{Yi-yi} = \frac{z-zi}{Zi-zi}$$

Here, i is a number that goes from 0 through 4.

This equation may alternatively be expressed with two equations:

$$\begin{cases} (x-xi)*(Yi-yi)-(y-yi)*(Xi-xi)=0 \\ (x-xi)*(Zi-zi)-(z-zi)*(Xi-xi)=0 \end{cases}$$

Since there are five markers in the present embodiment and there is a pair of equations above for each of the five markers, there are 10 equations that describe distances between the markers. Eight additional equations involving the positions of the markers may be derived through use of the Pythagorean Theorem. Accordingly, the following equations may result:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z2-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x-x4)*(Y4-y4)-(y-y4)*(X4-x4)=0 \\ (x-x4)*(Z4-z4)-(z-z4)*(X4-x4)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x2-x3)^2-(y2-y3)^2-(z2-z3)^2-l23^2=0 \end{cases}$$

However, this set of equations does not include all equations that describe the positions of the markers relative to each other. It is therefore necessary to check the solutions of the set of equations for the 3-D positions of the x-ray source 301 and of the object 310 in relation to the following equations that were not included in the system:

$$\begin{cases} (x2-x3)^2-(y2-y3)^2-(z2-z3)^2-l23^2=0, \\ (x2-x4)^2-(y2-y4)^2-(z2-z4)^2-l24^2=0, \\ (x3-x4)^2-(y3-y4)^2-(32-z4)^2-l34^2=0. \end{cases}$$

Second 3-D positions of the x-ray source 301 and of the object 310 may be determined by using a substantially similar mathematical model discussed below, in which it is assumed that ('x,'y,'z) are coordinates of the x-ray source 301 and ('X0,'Y0,'Z0) through ('X4,'Y4,'Z4) are coordinates of a second set of projections of the five markers on the second roentgenogram.

$$\begin{cases} ('x-x0)*(Y'0-y0)-('y-y0)*('X0-x0)=0 \\ ('x-x0)*(Z'0-z0)-('z-z0)*('X0-x0)=0 \\ ('x-x1)*(Y'1-y1)-('y-y1)*('X1-x1)=0 \\ ('x-x1)*(Z'1-z1)-('z-z1)*('X1-x1)=0 \\ ('x-x2)*(Y'2-y2)-('y-y2)*('X2-x2)=0 \\ ('x-x2)*(Z'2-z2)-('z-z2)*('X2-x2)=0 \\ ('x-x3)*(Y'3-y3)-('y-y3)*('X3-x3)=0 \\ ('x-x3)*(Z'3-z3)-('z-z3)*('X3-x3)=0 \\ ('x-x4)*(Y'4-y4)-('y-y4)*('X4-x4)=0 \\ ('x-x4)*(Z'4-z4)-('z-z4)*('X4-x4)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x2-x3)^2-(y2-y3)^2-(z2-z3)^2-l23^2=0 \end{cases}$$

However, this set of equations does not include all equations that describe the positions of the markers relative to each other. It is therefore necessary to check the solutions of the set of equations for the 3-D positions of the x-ray source 301 and of the object 310 in relation to the following equations that were not included in the system:

$$\begin{cases} (x2-x3)^2-(y2-y3)^2-(z2-z3)^2-l23^2=0, \\ (x2-x4)^2-(y2-y4)^2-(z2-z4)^2-l24^2=0, \\ (x3-x4)^2-(y3-y4)^2-(32-z4)^2-l34^2=0. \end{cases}$$

The first and second 3-D positions of the x-ray source 301 and of the object 310 may thereby be found.

In certain situations, changes in the Z coordinate of the x-ray source 301 may result in proportional changes of projections of the markers on the roentgenograms. In these situations, the Z coordinate of the x-ray source 301 can be set as a constant parameter that does not have to be solved when solving the set of equations. Here, the constant parameter for the Z coordinate should be a large number that allows the object to fit between the x-ray source 301 and the roentgenogram. This allows use of less markers for determining the 3-D positions of the x-ray source 301 and of the object 310 as illustrated in Models 2 through 4 below.

Model 2

In the present embodiment of the techniques, the plurality of markers may comprise four markers. In the present embodiment, the first 3-D positions of the x-ray source 301 and of the object 310 may be determined by using the mathematical model discussed below, in which it is assumed that (x,y,z) are coordinates of the x-ray source 301, (x0,y0,z0) through (x3,y3,z3) are coordinates of the four markers 303, (X0,Y0,Z0) through (X3,Y3,Z3) are coordinates of a first set of projections of the four markers 303 on a first roentgenogram, and l01, l02, l03, l12, l13, l23 are predetermined distances between the four markers 303. The relationships between these variables are further depicted in FIG. 4.

The three points (x, y, z), (xi, yi, zi), and (Xi, Yi, Zi) are situated on the same line passing from the x-ray source 301, to the marker 303, and then to the imager 304. The equation for this line may thus be expressed as:

$$\frac{x-xi}{Xi-xi}=\frac{y-yi}{Yi-yi}=\frac{z-zi}{Zi-zi}$$

This equation may alternatively be expressed with two equations:

$$\begin{cases} (x-xi)*(Yi-yi)-(y-yi)*(Xi-xi)=0 \\ (x-xi)*(Zi-zi)-(z-zi)*(Xi-xi)=0 \end{cases}$$

Here, i is a number that goes from 0 through 3.

Since there are four markers in the present embodiment and there is a pair of equations above for each of the four markers, there are eight equations that describe distances between the markers. Six additional equations involving the positions of the markers can be derived through use of the Pythagorean Theorem. Accordingly, the following equations may result:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z2-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

The second 3-D positions of the x-ray source 301 and of the object 310 may be determined by using a substantially similar mathematical model discussed below, in which it is assumed that ('x,'y,'z) are coordinates of the x-ray source 301 and ('X0,'Y0,'Z0) through ('X3,'Y3,'Z3) are coordinates of a second set of projections of the four markers on the second roentgenogram.

$$\begin{cases} ('x-x0)*(Y'0-y0)-('y-y0)*('X0-x0)=0 \\ ('x-x0)*(Z'0-z0)-('z-z0)*('X0-x0)=0 \\ ('x-x1)*(Y'1-y1)-('y-y1)*('X1-x1)=0 \\ ('x-x1)*(Z'1-z1)-('z-z1)*('X1-x1)=0 \\ ('x-x2)*(Y'2-y2)-('y-y2)*('X2-x2)=0 \\ ('x-x2)*(Z'2-z2)-('z-z2)*('X2-x2)=0 \\ ('x-x3)*(Y'3-y3)-('y-y3)*('X3-x3)=0 \\ ('x-x3)*(Z'3-z3)-('z-z3)*('X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

The first and second 3-D positions of the x-ray source 301 and of the object 310 may thereby be found.

Model 3

In another embodiment of the techniques, the plurality of markers may once again be four markers. In the present embodiment, the first 3-D positions of the x-ray source 301 and of the object 310 may be determined by using the mathematical model discussed below, in which it is assumed that (x,y,z) are coordinates of the x-ray source 301, (x0,y0,z0) through (x3,y3,z3) are coordinates of the four markers 303, (X0,Y0,Z0) through (X3,Y3,Z3) are coordinates of the first set of projections of the four markers 303 on the first roentgenogram, and l01, l02, l03, l12, l13, l23 are predetermined distances between the four markers 303. The relationships between these variables are further depicted in FIG. 4.

The present embodiment employs the following parametric equations:

$$x=x0+\alpha*t; y=y0+\beta*t; z=z0+\gamma*t$$

Here, $\alpha, \beta, \gamma$ refer to directing vectors, and t is a parameter characterizing the point (x,y,z) on a line relative to another point, for example (x0,y0,z0). And the three points (x, y, z), (xi, yi, zi), and (Xi, Yi, Zi) are situated on the same line. The parametric equations for this line may thus be expressed as:

$$xi=x+\alpha_i*t_i; yi=y+\beta_i*t_i; zi=z+\gamma_i*t_i$$

where:

$$\alpha_i=Xi-x; \beta_i=Yi-y; \gamma_i=Zi-z$$

Here, i is a number that goes from 0 through 3.

The present embodiment employs 14 equations by adding an appropriate number of equations for distances between the markers on the object (six equations for six distances between connection points of known geometry). By placing them into equations for distances between the markers, the present embodiment provides the following six equations:

$$\begin{cases} (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

The embodiment may determine t0 through t3, x, and y by solving for the six equations above. The first 3-D positions of the x-ray source 301 and of the object 310 may then be determined. The second 3-D positions of the x-ray source 301 and of the object 310 may be determined by using a substantially similar mathematical model.

The three points ('x,'y,'z), (xi, yi, zi), and ('Xi,'Yi,'Zi) are situated on the same line. The parametric equations for this line may thus be expressed as:

$$xi='x+\alpha_i*t_i; yi='y+\beta_i*t_i; zi='z+\gamma_i*t_i$$

where:

$$\alpha_i='Xi-x; \beta_i='Yi-y; \gamma_i='Zi-z$$

Here, i is a number that goes from 0 through 3.

The present embodiment employs 14 equations by adding an appropriate number of equations for distances between the markers on the object (six equations for six distances between the connection points of known geometry). By placing them into equations for distances between the markers, the present embodiment provides the following six equations:

$$\begin{cases} (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

The first and second 3-D positions of the x-ray source 301 and of the object (t0 through t3,x,y) may thereby be found.

Model 4

Figure 4:
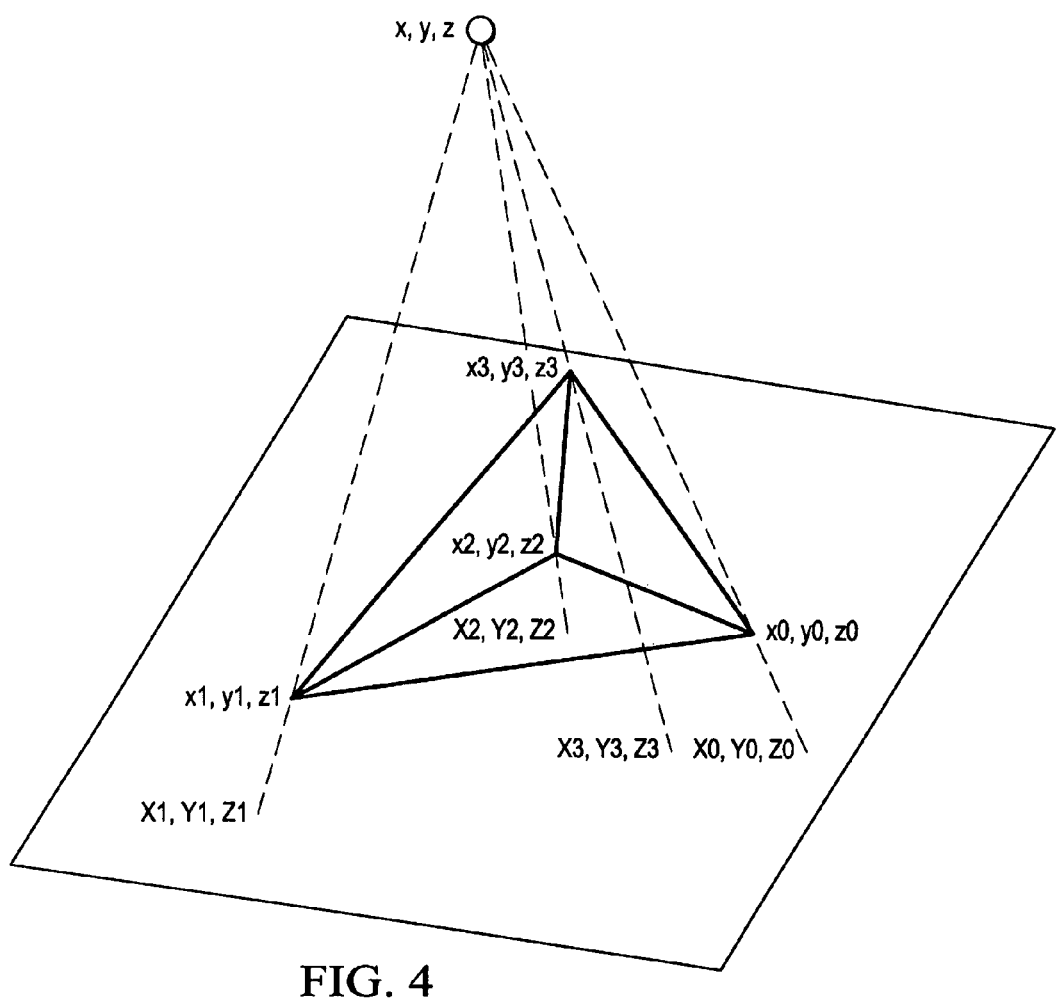
FIG. 4 is a schematic view of coordinates of an x-ray source and projections of markers on an imager, in accordance with the present disclosure.

In another embodiment of the techniques, the plurality of markers may comprise four markers. In the present embodiment, the first 3-D positions of the x-ray source 301 and of the object 310 may be determined by using the mathematical model discussed below, in which it is assumed that (x,y,z) are coordinates of the x-ray source 301, (x0,y0,z0) through (x3,y3,z3) are coordinates of the four markers 303, (X0,Y0,Z0) through (X3,Y3,Z3) are coordinates of a first set of projections of the four markers 303 on the first roentgenogram, and l01, l02, l03, l12, l13, l23 are predetermined distances between the four markers 303. The relationships between these variables are depicted in FIG. 4. Furthermore, each marker is located on a plane that crosses the x-ray source 301, a projection point of the marker, and a projection point of a neighboring marker. Thus, two planes appurtenant equations may be determined for each marker of the object, creating a system of eight equations for the object 310 with four markers as provided below.

$$\begin{cases} \begin{vmatrix} x0-x & y0-y & z0-z \\ X0-x & Y0-x & Z0-z \\ X1-x & Y1-y & Z1-z \end{vmatrix} = 0 \\ \begin{vmatrix} x1-x & y1-y & z1-z \\ X0-x & Y0-x & Z0-z \\ X1-x & Y1-y & Z1-z \end{vmatrix} = 0 \\ \begin{vmatrix} x1-x & y1-y & z1-z \\ X1-x & Y1-x & Z1-z \\ X2-x & Y2-y & Z2-z \end{vmatrix} = 0 \\ \begin{vmatrix} x2-x & y2-y & z2-z \\ X1-x & Y1-x & Z1-z \\ X2-x & Y2-y & Z2-z \end{vmatrix} = 0 \end{cases}$$

$$\begin{cases} \begin{vmatrix} x2-x & y2-y & z2-z \\ X2-x & Y2-x & Z2-z \\ X3-x & Y3-y & Z3-z \end{vmatrix} = 0 \\ \begin{vmatrix} x3-x & y3-y & z3-z \\ X2-x & Y2-x & Z2-z \\ X3-x & Y3-y & Z3-z \end{vmatrix} = 0 \\ \begin{vmatrix} x3-x & y3-y & z3-z \\ X3-x & Y3-x & Z3-z \\ X0-x & Y0-y & Z0-z \end{vmatrix} = 0 \\ \begin{vmatrix} x0-x & y0-y & z0-z \\ X3-x & Y3-x & Z3-z \\ X0-x & Y0-y & Z0-z \end{vmatrix} = 0 \end{cases}$$

Now, by adding an appropriate number of equations for distances between the markers (e.g., six equations for six distances between four points of known geometry fixator), the embodiment provides the following mathematical model of 14 equations:

$$\begin{cases} \begin{vmatrix} x0-x & y0-y & z0-z \\ X0-x & Y0-x & Z0-z \\ X1-x & Y1-y & Z1-z \end{vmatrix} = 0 \\ \begin{vmatrix} x1-x & y1-y & z1-z \\ X0-x & Y0-x & Z0-z \\ X1-x & Y1-y & Z1-z \end{vmatrix} = 0 \\ \begin{vmatrix} x1-x & y1-y & z1-z \\ X1-x & Y1-x & Z1-z \\ X2-x & Y2-y & Z2-z \end{vmatrix} = 0 \\ \begin{vmatrix} x2-x & y2-y & z2-z \\ X1-x & Y1-x & Z1-z \\ X2-x & Y2-y & Z2-z \end{vmatrix} = 0 \\ \begin{vmatrix} x2-x & y2-y & z2-z \\ X2-x & Y2-x & Z2-z \\ X3-x & Y3-y & Z3-z \end{vmatrix} = 0 \end{cases}$$

-continued $$\begin{cases} \begin{vmatrix} x3-x & y3-y & z3-z \\ X2-x & Y2-x & Z2-z \\ X3-x & Y3-y & Z3-z \end{vmatrix} = 0 \\ \begin{vmatrix} x3-x & y3-y & z3-z \\ X3-x & Y3-x & Z3-z \\ X0-x & Y0-y & Z0-z \end{vmatrix} = 0 \\ \begin{vmatrix} x0-x & y0-y & z0-z \\ X3-x & Y3-x & Z3-z \\ X0-x & Y0-y & Z0-z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x2-x3)^2 - (y2-y3)^2 - (z2-z3)^2 - l23^2 = 0 \end{cases}$$

The first 3-D position of the x-ray source 301 and of the object 310 may be determined by solving for the equations above. The second 3-D positions of the x-ray source 301 and of the object 310 may be determined by using a substantially similar mathematical model discussed below, in which it is assumed that ('x,'y,'z) are coordinates of the x-ray source 301 and ('X0,'Y0,'Z0) through ('X3,'Y3,'Z3) are coordinates of a second set of projections of the four markers on the second roentgenogram.

$$\begin{cases} \begin{vmatrix} x0-'x & y0-'y & z0-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X1-'x & 'Y1-'x & 'Z1-'z \\ 'X2-'x & 'Y2-'y & 'Z2-'z \end{vmatrix} = 0 \\ \begin{vmatrix} x2-'x & y2-'y & z2-'z \\ 'X1-'x & 'Y1-'x & 'Z1-'z \\ 'X2-'x & 'Y2-'y & 'Z2-'z \end{vmatrix} = 0 \\ \begin{vmatrix} x2-'x & y2-'y & z2-'z \\ 'X2-'x & 'Y2-'x & 'Z2-'z \\ 'X3-'x & 'Y3-'y & 'Z3-'z \end{vmatrix} = 0 \end{cases}$$

-continued $$\begin{vmatrix} x3 - {'}x & y3 - {'}y & z3 - {'}z \\ {'}X2 - {'}x & {'}Y2 - {'}x & {'}Z2 - {'}z \\ {'}X3 - {'}x & {'}Y3 - {'}y & {'}Z3 - {'}z \end{vmatrix} = 0$$

$$\begin{vmatrix} x3 - {'}x & y3 - {'}y & z3 - {'}z \\ {'}X3 - {'}x & {'}Y3 - {'}x & {'}Z3 - {'}z \\ {'}X0 - {'}x & {'}Y0 - {'}y & {'}Z0 - {'}z \end{vmatrix} = 0$$

$$\begin{vmatrix} x0 - {'}x & y0 - {'}y & z0 - {'}z \\ {'}X3 - {'}x & {'}Y3 - {'}x & {'}Z3 - {'}z \\ {'}X0 - {'}x & {'}Y0 - {'}y & {'}Z0 - {'}z \end{vmatrix} = 0$$

$(x0 - x1)^2 - (y0 - y1)^2 - (z0 - z1)^2 - l01^2 = 0$
$(x0 - x2)^2 - (y0 - y2)^2 - (z0 - z2)^2 - l02^2 = 0$
$(x0 - x3)^2 - (y0 - y3)^2 - (z0 - z3)^2 - l03^2 = 0$
$(x1 - x2)^2 - (y1 - y2)^2 - (z1 - z2)^2 - l12^2 = 0$
$(x1 - x3)^2 - (y1 - y3)^2 - (z1 - z3)^2 - l13^2 = 0$
$(x2 - x3)^2 - (y2 - y3)^2 - (z2 - z3)^2 - l23^2 = 0$

The first and second 3-D positions of the x-ray 301 and of the object may thereby be determined.

Using Projections of Struts

Another embodiment of the techniques disclosed herein comprises receiving first and second roentgenograms of an object disposed between an x-ray source and an imager. FIG. 2A is a schematic diagram operable to obtain the first and second roentgenograms in first and second orientations 220, 230, respectively. To obtain the first and second roentgenograms, a body part 201 surrounded by an object 210 is placed between an x-ray source 202 and an imager 204. The object 210 may be an orthopedic fixator, or more specifically a hexapod as shown in FIG. 2A. The object 210 comprises a plurality of struts 205 with predetermined lengths that are each connected to at least two fixation members 206 with predetermined dimensions. In this embodiment, the fixation members 206 are rings, but other embodiments may employ differently shaped fixation members. To generate the first roentgenogram, the body part 201 surrounded by the object 210, the x-ray source 202, and the imager 204 are in a first orientation 220 relative to each other. The second roentgenogram may be generated by either rotating the body part 201 surrounded by the object 210 to a new second orientation 230 with respect to the x-ray source 202 and the imager 204, or as shown in FIG. 2A, by rotating the x-ray source 202 and the imager 204 to a new second orientation 230 about the body part 201. The first roentgenogram therefore includes a first image of the body part 201, the object 210, and the plurality of struts 205 with predetermined lengths that are each connected to at least two fixation members 206 with predetermined dimensions. Similarly, the second roentgenogram includes a second image of the body part 201, the object 210, and the plurality of struts 205 with predetermined lengths that are each connected to the at least two fixation members 206 with predetermined dimensions.

The present embodiment determines a first set of projections of the plurality of struts 205 as depicted on the first roentgenogram and a second set of projections of the plurality of struts 205 as depicted on the second roentgenogram. In an embodiment, the first and second sets of projections of the plurality of struts 205 more specifically involve projections of longitudinal axes of the plurality of the struts 205. In another embodiment, the first and second sets of projections of the plurality of struts 205 involve the projections of strut connection points, wherein the strut connection points refer to points where the struts 205 meet the fixation members 206. In another embodiment, sets of the projections of the longitudinal axes of the struts and of the projections of the strut connection points are both employed. FIG. 2B illustrates determining a projection of a strut 205 as depicted on the first roentgenogram 220 and as depicted on the second roentgenogram 230. The present embodiment may then determine a first 3-D position of the x-ray source 202 and a first 3-D position of the object 210 with respect to the x-ray imager using the predetermined lengths of the plurality of struts 205 and the first set of projections of the plurality of struts 205 as depicted on the first roentgenogram 220. Similarly, the technique may then determine a second 3-D position of the x-ray source 202 and a second 3-D position of the object 210 with respect to the x-ray imager using the predetermined lengths of the plurality of struts 205 and the second set of projections of the plurality of struts 205 as depicted on the second roentgenogram 230. Various mathematical models may be employed to determine the first and second 3-D positions of the x-ray source 202 and of the object 210. These models will be described in greater detail later.

Once the first and second 3-D positions of the x-ray source 202 and of the object 210 are determined, the technique may then align the first and second 3-D object projections in a 3-D reference frame using the 3-D positions of the plurality of struts 205 with respect to the x-ray imager 204 in the first and second orientations 220, 230. The embodiment may then create a 3-D model of the imaged body part in the 3-D reference frame based on the first and second 3-D object projections. Another embodiment may create a 3-D model of the object 210 only or in addition to the 3-D model of the imaged body part.

Model 5

Figure 5:
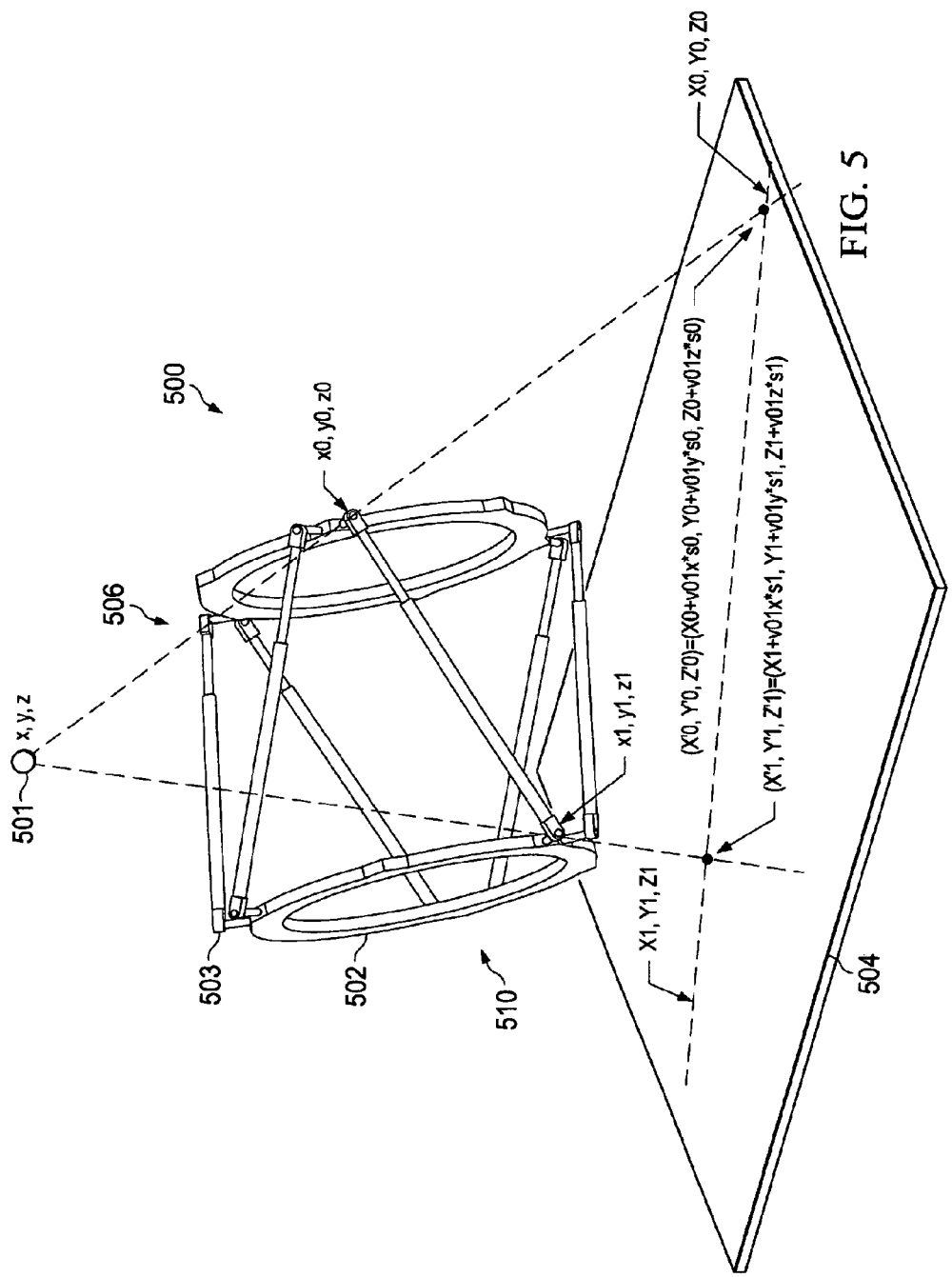
FIG. 5 is a perspective view of an imaging system and an object with struts in an orientation, in accordance with the present disclosure.

In an exemplary embodiment of the techniques disclosed herein, the plurality of struts may comprise five struts. FIG. 5 depicts object 510 comprising two fixation members 502 and five struts 506 in an orientation. In the present embodiment, the first 3-D positions of the x-ray source 501 and of the object 510 may be determined by using the mathematical model discussed below, in which it is assumed that (x,y,z) are coordinates of the x-ray source 501, (x0,y0,z0) through (x9,y9,z9) are coordinates of the ten strut connection points 503 to the fixation members 502, (X0,Y0,Z0) to (X1,Y1, Z1), . . . (X8,Y8,Z8) to (X9,Y9,Z9) are a first set of projections of longitudinal axes of the struts 506 on the first roentgenogram, l01, l02, l03, l04, l06, l07, l08, l09, l12, l13, l14, l15, l16, l17, l18, l19, l23, l24, l25, l26, l27, l28, l29 are the predetermined distances between the ten strut connection points 503, si are unknown ratios, and v(i−1)ix, v(i−1)iy, v(i−1)iz are vectors of the projections of the longitudinal axes of the struts 506, wherein v(i−1)ix=Xi−X(i−1), v(i−1)iy=Yi−Y(i−1), v(i−1)iz=Zi−Z(i−1). Here, i is a number that goes from 0 through 9. Thus, for example, v01x=X1−X0, v01y=Y1−Y0, v01z=Z1−Z0. There are thus 33 unknown parameters, which require a system with 33 equations to determine the positions of the x-ray source 501 and of the object 510.

Furthermore, coordinates of the projections of the strut connection points can be represented by the following equations:

X coordinate: $X0 + v01x * s0$

Y coordinate: $Y0 + v01y * s0$

Z coordinate: $Z0 + v01z * s0$.

Coordinates of other strut connection points 503 are determined similarly, which results in 43 unknown parameters. Thus, 43 equations are needed to solve the mathematical model with 43 unknown parameters. However, this mathematical model may produce unlimited number of solutions. The present embodiment may determine a single distinguishable point on the projection to limit the number of solutions. The projection of one of the strut ends may be manually determined by a user. For example, the user may determine the projection of the point (X9, Y9, Z9) in which case s9=0, allowing the mathematical model of 42 equations to be solved.

In the present embodiment, the x-ray source 501, the strut connection points 503, and the projections of the strut connection points lie on the same line. Thus, for point (x0, y0, z0), the following pair of equations may be determined:

$$\begin{cases} (x-x0)*(Y0+v01y*s0-y0)-(y-y0)*(X0+v01x*s0-x0)=0 \\ (x-x0)*(Z0+v01z*s0-z0)-(z-z0)*(X0+v01x*s0-x0)=0 \end{cases}$$

Since there are five struts in the present embodiment and there is a pair of equations above for each strut, there are 10 equations that describe the strut connection points. 22 additional equations involving the positions of the strut connection points can be derived through use of the Pythagorean Theorem. Accordingly, the following equations may result:

$$\begin{cases}
(x-x0)*(Y0+v01y*s0-y0)-(y-y0)*(X0+v01x*s0-x0)=0 \\
(x-x0)*(Z0+v01z*s0-z0)-(z-z0)*(X0+v01x*s0-x0)=0 \\
(x-x1)*(Y1+v01y*s1-y1)-(y-y1)*(X1+v01x*s1-x1)=0 \\
(x-x1)*(Z1+v01z*s1-z1)-(z-z1)*(X1+v01x*s1-x1)=0 \\
(x-x2)*(Y2+v23y*s2-y2)-(y-y2)*(X2+v23x*s2-x2)=0 \\
(x-x2)*(Z2+v23z*s2-z2)-(z-z2)*(X2+v23x*s2-x2)=0 \\
(x-x3)*(Y3+v23y*s3-y3)-(y-y3)*(X3+v23x*s3-x3)=0 \\
(x-x3)*(Z3+v23z*s3-z3)-(z-z3)*(X3+v23x*s3-x3)=0 \\
(x-x4)*(Y4+v45y*s4-y4)-(y-y4)*(X4+v45x*s4-x4)=0 \\
(x-x4)*(Z4+v45z*s4-z4)-(z-z4)*(X4+v45x*s4-x4)=0 \\
(x-x5)*(Y5+v45y*s5-y5)-(y-y5)*(X5+v45x*s5-x5)=0 \\
(x-x5)*(Z5+v45z*s5-z5)-(z-z5)*(X5+v45x*s5-x5)=0 \\
(x-x6)*(Y6+v67y*s6-y6)-(y-y6)*(X6+v67x*s6-x6)=0 \\
(x-x6)*(Z6+v67z*s6-z6)-(z-z6)*(X6+v67x*s6-x6)=0 \\
(x-x7)*(Y7+v67y*s7-y7)-(y-y7)*(X7+v67x*s7-x7)=0 \\
(x-x7)*(Z7+v67z*s7-z7)-(z-z7)*(X7+v67x*s7-x7)=0 \\
(x-x8)*(Y8+v89y*s8-y8)-(y-y8)*(X8+v89x*s8-x8)=0 \\
(x-x8)*(Z8+v89z*s8-z8)-(z-z8)*(X8+v89x*s8-x8)=0 \\
(x-x9)*(Y9+v89y*s9-y9)-(y-y9)*(X9+v89x*s9-x9)=0 \\
(x-x9)*(Z9+v89z*s9-z9)-(z-z9)*(X9+v89x*s9-x9)=0 \\
(x0-x1)^2-(y0-y1)^2-(z0-z1)^2-l01^2=0 \\
(x0-x2)^2-(y0-y2)^2-(z0-z2)^2-l02^2=0 \\
(x0-x3)^2-(y0-y3)^2-(z0-z3)^2-l03^2=0 \\
(x0-x4)^2-(y0-y4)^2-(z0-z4)^2-l04^2=0 \\
(x0-x5)^2-(y0-y5)^2-(z0-z5)^2-l05^2=0 \\
(x0-x6)^2-(y0-y6)^2-(z0-z6)^2-l06^2=0 \\
(x0-x7)^2-(y0-y7)^2-(z0-z7)^2-l07^2=0 \\
(x0-x8)^2-(y0-y8)^2-(z0-z8)^2-l08^2=0 \\
(x0-x9)^2-(y0-y9)^2-(z0-z9)^2-l09^2=0 \\
(x1-x2)^2-(y1-y2)^2-(z1-z2)^2-l12^2=0 \\
(x1-x3)^2-(y1-y3)^2-(z1-z3)^2-l13^2=0 \\
(x1-x4)^2-(y1-y4)^2-(z1-z4)^2-l14^2=0 \\
(x1-x5)^2-(y1-y5)^2-(z1-z5)^2-l15^2=0 \\
(x1-x6)^2-(y1-y6)^2-(z1-z6)^2-l16^2=0 \\
(x1-x7)^2-(y1-y7)^2-(z1-z7)^2-l17^2=0 \\
(x1-x8)^2-(y1-y8)^2-(z1-z8)^2-l18^2=0 \\
(x1-x9)^2-(y1-y9)^2-(z1-z9)^2-l19^2=0 \\
(x2-x3)^2-(y2-y3)^2-(z2-z3)^2-l23^2=0 \\
(x2-x4)^2-(y2-y4)^2-(z2-z4)^2-l24^2=0 \\
(x2-x5)^2-(y2-y5)^2-(z2-z5)^2-l25^2=0 \\
(x2-x6)^2-(y2-y6)^2-(z2-z6)^2-l26^2=0 \\
(x2-x7)^2-(y2-y7)^2-(z2-z7)^2-l27^2=0
\end{cases}$$

However, this set of equations does not include all equations that describe the positions of the markers relative to each other. Therefore, it is necessary to check the solutions of the set of equations for the 3-D positions of the x-ray source 501 and of the object 510 in relation to those equations that were not included in the system:

$$\begin{cases} (x2-x8)^2-(y2-y8)^2-(z2-z8)^2-l28^2=0 \\ (x2-x9)^2-(y2-y9)^2-(z2-z9)^2-l29^2=0 \end{cases}$$

The second 3-D positions of the x-ray source 501 and of the object 510 may be determined by using a substantially similar mathematical model discussed below, in which it is assumed that ('x,'y,'z) are coordinates of the x-ray source 301, ('X0,'Y0,'Z0) to ('X1,'Y1,'Z1), ... ('X8,'Y8,'Z8) to ('X9,'Y9,'Z9) are a second set of projections of longitudinal axes of the struts 506 on the second roentgenogram, 'si are unknown ratios, and 'v(i−1)ix, 'v(i−1)iy, 'v(i−1)iz are vectors of projections of the longitudinal axes of the struts 506, wherein 'v(i−1)ix='Xi−'X(i−1), 'v(i−1)iy='Yi−'v(i−1), 'v(i−1)iz='Zi−'Z(i−1). Here, i is a number that goes from 0 through 9. Thus, for example, 'v01x='X1−'X0, 'v01y='Y1−'Y0, 'v01z='Z1−'Z0.

$$\begin{cases} ('x-x0)*('Y0+'v01y*'s0-y0)-('y-y0)*('X0+'v01x*'s0-x0)=0 \\ ('x-x0)*('Z0+'v01z*'s0-z0)-('z-z0)*('X0+'v01x*'s0-x0)=0 \\ ('x-x1)*('Y1+'v01y*'s1-y1)-('y-y1)*('X1+'v01x*'s1-x1)=0 \\ ('x-x1)*('Z1+'v01z*'s1-z1)-('z-z1)*('X1+'v01x*'s1-x1)=0 \\ ('x-x2)*('Y2+'v23y*'s2-y2)-('y-y2)*('X2+'v23x*'s2-x2)=0 \\ ('x-x2)*('Z2+'v23z*'s2-z2)-('z-z2)*('X2+'v23x*'s2-x2)=0 \\ ('x-x3)*('Y3+'v23y*'s3-y3)-('y-y3)*('X3+'v23x*'s3-x3)=0 \\ ('x-x3)*('Z3+'v23z*'s3-z3)-('z-z3)*('X3+'v23x*'s3-x3)=0 \\ ('x-x4)*('Y4+'v45y*'s4-y4)-('y-y4)*('X4+'v45x*'s4-x4)=0 \\ ('x-x4)*('Z4+'v45z*'s4-z4)-('z-z4)*('X4+'v45x*'s4-x4)=0 \\ ('x-x5)*('Y5+'v45y*'s5-y5)-('y-y5)*('X5+'v45x*'s5-x5)=0 \\ ('x-x5)*('Z5+'v45z*'s5-z5)-('z-z5)*('X5+'v45x*'s5-x5)=0 \\ ('x-x6)*('Y6+'v67y*'s6-y6)-('y-y6)*('X6+'v67x*'s6-x6)=0 \\ ('x-x6)*('Z6+'v67z*'s6-z6)-('z-z6)*('X6+'v67x*'s6-x6)=0 \\ ('x-x7)*('Y7+'v67y*'s7-y7)-('y-y7)*('X7+'v67x*'s7-x7)=0 \\ ('x-x7)*('Z7+'v67z*'s7-z7)-('z-z7)*('X7+'v67x*'s7-x7)=0 \\ ('x-x8)*('Y8+'v89y*'s8-y8)-('y-y8)*('X8+'v89x*'s8-x8)=0 \\ ('x-x8)*('Z8+'v89z*'s8-z8)-('z-z8)*('X8+'v89x*'s8-x8)=0 \\ ('x-x9)*('Y9+'v89y*'s9-y9)-('y-y9)*('X9+'v89x*'s9-x9)=0 \\ ('x-x9)*('Z9+'v89z*'s9-z9)-('z-z9)*('X9+'v89x*'s9-x9)=0 \end{cases}$$

$$\begin{cases} (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x0-x5)^2-(y0-y5)^2-(z0-z5)^2-l05^2=0 \\ (x0-x6)^2-(y0-y6)^2-(z0-z6)^2-l06^2=0 \\ (x0-x7)^2-(y0-y7)^2-(z0-z7)^2-l07^2=0 \\ (x0-x8)^2-(y0-y8)^2-(z0-z8)^2-l08^2=0 \\ (x0-x9)^2-(y0-y9)^2-(z0-z9)^2-l09^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x1-x5)^2-(y1-y5)^2-(z1-z5)^2-l15^2=0 \\ (x1-x6)^2-(y1-y6)^2-(z1-z6)^2-l16^2=0 \\ (x1-x7)^2-(y1-y7)^2-(z1-z7)^2-l17^2=0 \\ (x1-x8)^2-(y1-y8)^2-(z1-z8)^2-l18^2=0 \\ (x1-x9)^2-(y1-y9)^2-(z1-z9)^2-l19^2=0 \\ (x2-x3)^2-(y2-y3)^2-(z2-z3)^2-l23^2=0 \\ (x2-x4)^2-(y2-y4)^2-(z2-z4)^2-l24^2=0 \\ (x2-x5)^2-(y2-y5)^2-(z2-z5)^2-l25^2=0 \\ (x2-x6)^2-(y2-y6)^2-(z2-z6)^2-l26^2=0 \\ (x2-x7)^2-(y2-y7)^2-(z2-z7)^2-l27^2=0 \end{cases}$$

However, this set of equations does not include all equations that describe the positions of the struts 506 and the strut connection points 503. It is therefore necessary to check the solutions of the set of equations for the 3-D positions of the x-ray source 501 and of the object 510 in relation to those equations that were not included in the system:

$$\begin{cases} (x2-x8)^2-(y2-y8)^2-(z2-z8)^2-l28^2=0 \\ (x2-x9)^2-(y2-y9)^2-(z2-z9)^2-l29^2=0 \end{cases}$$

The first and second 3-D positions of the x-ray source 501 and of the object 510 may thereby be found.

In certain situations, changes in the Z coordinate of the x-ray source 501 result in proportional changes of projections of the markers on the roentgenograms. In these situations, the Z coordinate of the x-ray source 501 can be set as a constant parameter that does not have to be solved when solving the set of equations. Here, the constant parameter for the Z coordinate should be a large number that allows the object 510 to fit between the x-ray source 501 and the roentgenogram. This allows use of less markers for determining the 3-D positions of the x-ray source 501 and of the object 510 as illustrated in Models 6 through 8 below.

Model 6

In the present embodiment of the techniques, the plurality of struts 506 may comprise four struts 506. In the present embodiment, the first 3-D positions of the x-ray source 501 and of the object 510 may be determined by using the mathematical model discussed below, in which it is assumed that (x,y,z) are coordinates of the x-ray source 501, (x0,y0, z0) through (x7,y7,z7) are coordinates of the eight strut connection points 503, (X0, Y0, Z0) to (X1, Y1, Z1), . . . (X6, Y6, Z6) to (X7, Y7, Z7) are a first set of projections of longitudinal axes of the struts on the first roentgenogram, l01, l02, l03, l04, l06, l07, l12, l13, l14, l15, l16, l17, l23, l24, l25, l26, l27 are predetermined distances between the eight strut connection points 503, si are unknown ratios, and v(i−1)ix, v(i−1)iy, v(i−1)iz are vectors of projections of the longitudinal axes of the struts, wherein v(i−1)ix=Xi−X(i−1), v(i−1)iy=Yi−Y(i−1), v(i−1)iz=Zi−Z(i−1). Here, i is a number that goes from 0 through 7. Thus, for example, v01x=X1−X0, v01y=Y1−Y0, v01z=Z1−Z0. These relationships of variables are further depicted in FIG. 6.

Furthermore, it is assumed that (X'0, Y'0, Z'0) through (X'7, Y'7, Z'7) are a first set of projections of the eight strut connection points 503 on the first roentgenogram, which may be represented in the following manner:

$$X'0 = X0 + v01x * s0;$$

$$Y'0 = Y0 + v01y * s0;$$

$$Z'0 = Z0 + v01z * s0.$$

Similar equations are determined for other strut connection points 503 to the fixation members 502.

The three points (x, y, z), (xi, yi, zi), and (X'i, Y'i, Z'i) are situated on the same line. The equation for this line may thus be expressed as:

$$\frac{x - xi}{X'i - xi} = \frac{y - yi}{Y'i - yi} = \frac{z - zi}{Z'i - zi}$$

This equation may alternatively be expressed with two equations:

$$\begin{cases} (x - xi)*(Y'i - yi) - (y - yi)*(X'i - xi) = 0 \\ (x - xi)*(Z'i - zi) - (z - zi)*(X'i - xi) = 0 \end{cases}$$

Since there are eight strut connection points 503 to the fixation members 502 and there is a pair of equations above for each strut connection point 503, there are 16 equations that describe the lengths of the struts 506. Eighteen additional equations involving the positions of the strut connections can be derived through use of the Pythagorean Theorem.

$$\begin{cases}
(x - x0) * (Y'0 - y0) - (y - y0) * (X'0 - x0) = 0 \\
(x - x0) * (Z'0 - z0) - (z - z0) * (X'0 - x0) = 0 \\
(x - x1) * (Y'1 - y1) - (y - y1) * (X'1 - x1) = 0 \\
(x - x1) * (Z'1 - z1) - (z - z1) * (X'1 - x1) = 0 \\
(x - x2) * (Y'2 - y2) - (y - y2) * (X'2 - x2) = 0 \\
(x - x2) * (Z'1 - z2) - (z - z2) * (X'2 - x2) = 0 \\
(x - x3) * (Y'3 - y3) - (y - y3) * (X'3 - x3) = 0 \\
(x - x3) * (Z'3 - z3) - (z - z3) * (X'3 - x3) = 0 \\
(x - x4) * (Y'4 - y4) - (y - y4) * (X'4 - x4) = 0 \\
(x - x4) * (Z'4 - z4) - (z - z4) * (X'4 - x4) = 0 \\
(x - x5) * (Y'5 - y5) - (y - y5) * (X'5 - x5) = 0 \\
(x - x5) * (Z'5 - z5) - (z - z5) * (X'5 - x5) = 0 \\
(x - x6) * (Y'6 - y6) - (y - y6) * (X'6 - x6) = 0 \\
(x - x6) * (Z'6 - z6) - (z - z6) * (X'6 - x6) = 0 \\
(x - x7) * (Y'7 - y7) - (y - y7) * (X'7 - x7) = 0 \\
(x - x7) * (Z'7 - z7) - (z - z7) * (X'7 - x7) = 0 \\
(x0 - x1)^2 - (y0 - y1)^2 - (z0 - z1)^2 - l01^2 = 0
\end{cases}$$

-continued $$\begin{cases}
(x0 - x2)^2 - (y0 - y2)^2 - (z0 - z2)^2 - l02^2 = 0 \\
(x0 - x3)^2 - (y0 - y3)^2 - (z0 - z3)^2 - l03^2 = 0 \\
(x0 - x4)^2 - (y0 - y4)^2 - (z0 - z4)^2 - l04^2 = 0 \\
(x0 - x5)^2 - (y0 - y5)^2 - (z0 - z5)^2 - l05^2 = 0 \\
(x0 - x6)^2 - (y0 - y6)^2 - (z0 - z6)^2 - l06^2 = 0 \\
(x0 - x7)^2 - (y0 - y7)^2 - (z0 - z7)^2 - l07^2 = 0 \\
(x1 - x2)^2 - (y1 - y2)^2 - (z1 - z2)^2 - l12^2 = 0 \\
(x1 - x3)^2 - (y1 - y3)^2 - (z1 - z3)^2 - l13^2 = 0 \\
(x1 - x4)^2 - (y1 - y4)^2 - (z1 - z4)^2 - l14^2 = 0 \\
(x1 - x5)^2 - (y1 - y5)^2 - (z1 - z5)^2 - l15^2 = 0 \\
(x1 - x6)^2 - (y1 - y6)^2 - (z1 - z6)^2 - l16^2 = 0 \\
(x1 - x7)^2 - (y1 - y7)^2 - (z1 - z7)^2 - l17^2 = 0 \\
(x2 - x3)^2 - (y2 - y3)^2 - (z2 - z3)^2 - l23^2 = 0 \\
(x2 - x4)^2 - (y2 - y4)^2 - (z2 - z4)^2 - l24^2 = 0 \\
(x2 - x5)^2 - (y2 - y5)^2 - (z2 - z5)^2 - l25^2 = 0 \\
(x2 - x6)^2 - (y2 - y6)^2 - (z2 - z6)^2 - l26^2 = 0 \\
(x2 - x7)^2 - (y2 - y7)^2 - (z2 - z7)^2 - l27^2 = 0
\end{cases}$$

The second 3-D positions of the x-ray source 501 and of the object 510 may be determined by using a substantially similar mathematical model discussed below, in which it is assumed that ('x,'y,'z) are coordinates of the x-ray source 501, ('X0,'Y0,'Z0) to ('X1,'Y1,'Z1), . . . ('X6,'Y6,'Z6) to ('X7,'Y7,'Z7) are a second set of projections of longitudinal axes of the struts 506 on the second roentgenogram, ('X'0, 'Y'0,'Z'0) through ('X'7,'Y'7,'Z'7) are coordinates of a second set of projections of the eight strut connection points 503 on the second roentgenogram, l01, l02, l03, l04, l06, l07, l12, l13, l14, l15, l16, l17, l23, l24, l25, l26, l27 are the predetermined distances of the eight strut connection points 503, si are unknown ratios, and 'v(i−1)ix, 'v(i−1)iy, 'v(i−1)iz are vectors of projections of the longitudinal axes of the struts 506, wherein 'v(i−1)ix='Xi−X(i−1), 'v(i−1)iy='Yi−'Y(i−1), 'v01z='Zi−'Z(i−1). Here, i is a number that goes from 0 through 7. Thus, for example, v01x=X1−X0, v01y=Y1−Y0, v01z=Z1−Z0.

$$\begin{cases}
('x - x0) * ('Y'0 - y0) - ('y - y0) * ('X'0 - x0) = 0 \\
('x - x0) * ('Z'0 - z0) - ('z - z0) * ('X'0 - x0) = 0 \\
('x - x1) * ('Y'1 - y1) - ('y - y1) * ('X'1 - x1) = 0 \\
('x - x1) * ('Z'1 - z1) - ('z - z1) * ('X'1 - x1) = 0 \\
('x - x2) * ('Y'2 - y2) - ('y - y2) * ('X'2 - x2) = 0 \\
('x - x2) * ('Z'1 - z2) - ('z - z2) * ('X'2 - x2) = 0 \\
('x - x3) * ('Y'3 - y3) - ('y - y3) * ('X'3 - x3) = 0 \\
('x - x3) * ('Z'3 - z3) - ('z - z3) * ('X'3 - x3) = 0 \\
('x - x4) * ('Y'4 - y4) - ('y - y4) * ('X'4 - x4) = 0 \\
('x - x4) * ('Z'4 - z4) - ('z - z4) * ('X'4 - x4) = 0 \\
('x - x5) * ('Y'5 - y5) - ('y - y5) * ('X'5 - x5) = 0 \\
('x - x5) * ('Z'5 - z5) - ('z - z5) * ('X'5 - x5) = 0 \\
('x - x6) * ('Y'6 - y6) - ('y - y6) * ('X'6 - x6) = 0 \\
('x - x6) * ('Z'6 - z6) - ('z - z6) * ('X'6 - x6) = 0 \\
('x - x7) * ('Y'7 - y7) - ('y - y7) * ('X'7 - x7) = 0 \\
('x - x7) * ('Z'7 - z7) - ('z - z7) * ('X'7 - x7) = 0 \\
(x0 - x1)^2 - (y0 - y1)^2 - (z0 - z1)^2 - l01^2 = 0
\end{cases}$$

-continued
$$\begin{cases}
(x0-x2)^2 - (y0-y2)^2 - (z0-z2)^2 - l02^2 = 0 \\
(x0-x3)^2 - (y0-y3)^2 - (z0-z3)^2 - l03^2 = 0 \\
(x0-x4)^2 - (y0-y4)^2 - (z0-z4)^2 - l04^2 = 0 \\
(x0-x5)^2 - (y0-y5)^2 - (z0-z5)^2 - l05^2 = 0 \\
(x0-x6)^2 - (y0-y6)^2 - (z0-z6)^2 - l06^2 = 0 \\
(x0-x7)^2 - (y0-y7)^2 - (z0-z7)^2 - l07^2 = 0 \\
(x1-x2)^2 - (y1-y2)^2 - (z1-z2)^2 - l12^2 = 0 \\
(x1-x3)^2 - (y1-y3)^2 - (z1-z3)^2 - l13^2 = 0 \\
(x1-x4)^2 - (y1-y4)^2 - (z1-z4)^2 - l14^2 = 0 \\
(x1-x5)^2 - (y1-y5)^2 - (z1-z5)^2 - l15^2 = 0 \\
(x1-x6)^2 - (y1-y6)^2 - (z1-z6)^2 - l16^2 = 0 \\
(x1-x7)^2 - (y1-y7)^2 - (z1-z7)^2 - l17^2 = 0 \\
(x2-x3)^2 - (y2-y3)^2 - (z2-z3)^2 - l23^2 = 0 \\
(x2-x4)^2 - (y2-y4)^2 - (z2-z4)^2 - l24^2 = 0 \\
(x2-x5)^2 - (y2-y5)^2 - (z2-z5)^2 - l25^2 = 0 \\
(x2-x6)^2 - (y2-y6)^2 - (z2-z6)^2 - l26^2 = 0 \\
(x2-x7)^2 - (y2-y7)^2 - (z2-z7)^2 - l27^2 = 0
\end{cases}$$

The first and second 3-D positions of the x-ray source 501 and of the object 510 may thereby be found.

Model 7

Figure 6:
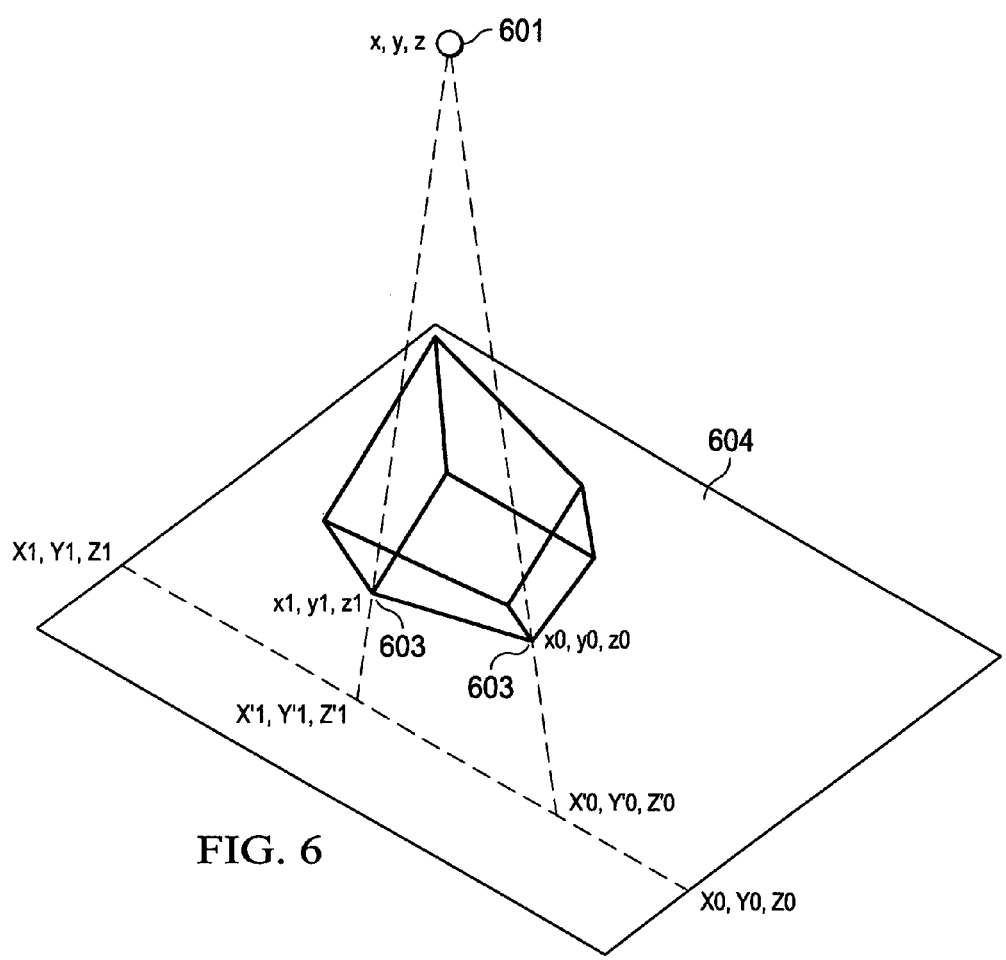
FIG. 6 is a schematic view of coordinates of an x-ray source and projections of strut connection points on an imager, in accordance with the present disclosure.

In another embodiment of the technique, the plurality of markers may comprise four struts. In the present embodiment, the first 3-D positions of the x-ray source 501 and of the object 510 may be determined by using the mathematical model discussed below, in which it is assumed that (x,y,z) are coordinates of the x-ray source 501, (x0,y0,z0) through (x7,y7,z7) are coordinates of the eight strut connection points 503 to the fixation members 502, (X0,Y0,Z0) to (X1,Y1,Z1), . . . (X6,Y6,Z6) to (X7,Y7,Z7) are a first set of projections of longitudinal axes of the struts 506 on the first roentgenogram, l01, l02, l03, l04, l06, l07, l12, l13, l14, l15, l16, l17, l23, l24, l25, l26, l27 are predetermined distances between the eight strut connection points 503, si are unknown ratios, and v(i−1)ix, v(i−1)iy, v(i−1)iz are vectors of projections of the longitudinal axes of the struts, wherein v(i−1)ix=Xi−X(i−1), v(i−1)iy=Yi−Y(i−1), v(i−1)iz=Zi−Z(i−1). Here, i is a number that goes from 0 through 7. Thus, for example, v01x=X1−X0, v01y=Y1−Y0, v01z=Z1−Z0. These relationships of variables are depicted in FIG. 6.

Furthermore, it is assumed that (X'0, Y'0, Z'0) through (X'7, Y'7, Z'7) are a first set of projections of the eight strut connection points 503 on the first roentgenogram, which may be represented in the following manner:

$X'0 = X0 + v01x * s0;$ $Y'0 = Y0 + v01y * s0;$ $Z'0 = Z0 + v01z * s0.$

Similar equations are determined for other strut connection points 503 to the fixation members 502.

The present embodiment employs the following parametric equations:

$x = x0 + \alpha * t; y = y0 + \beta * t; z = z0 + \gamma * t$

Here, α, β, γ refer to directing vectors, and t is a parameter characterizing the point (x,y,z) on a line relative to another point, for example (x0,y0,z0). And the three points (x, y, z), (xi, yi, zi), and (X'i, Y'i, Z'i) are situated on the same line passing from the x-ray source 601, to the marker 603, and then to the imager 604. Here, i is a number that goes from 0 through 7. The parametric equations for this line may thus be expressed as:

$xi = x + \alpha_i * t_i; yi = y + \beta_i * t_i; zi = z + \gamma_i * t_i$ where:

$\alpha_i = X'i - x; \beta_i = Y'i - y; \gamma_i = Z'i - z$

The present embodiment determines 18 equations by adding appropriate number of equations for distances between the strut connection points 503 on the fixation members 502 (18 equations for 18 distances between 8 strut connection points 503 of four struts 506 of known geometry fixator). The resulting 18 equations are provided below:

$$\begin{cases}
(x0-x1)^2 - (y0-y1)^2 - (z0-z1)^2 - l01^2 = 0 \\
(x0-x2)^2 - (y0-y2)^2 - (z0-z2)^2 - l02^2 = 0 \\
(x0-x3)^2 - (y0-y3)^2 - (z0-z3)^2 - l03^2 = 0 \\
(x0-x4)^2 - (y0-y4)^2 - (z0-z4)^2 - l04^2 = 0 \\
(x0-x5)^2 - (y0-y5)^2 - (z0-z5)^2 - l05^2 = 0 \\
(x0-x6)^2 - (y0-y6)^2 - (z0-z6)^2 - l06^2 = 0 \\
(x0-x7)^2 - (y0-y7)^2 - (z0-z7)^2 - l07^2 = 0 \\
(x1-x2)^2 - (y1-y2)^2 - (z1-z2)^2 - l12^2 = 0 \\
(x1-x3)^2 - (y1-y3)^2 - (z1-z3)^2 - l13^2 = 0 \\
(x1-x4)^2 - (y1-y4)^2 - (z1-z4)^2 - l14^2 = 0 \\
(x1-x5)^2 - (y1-y5)^2 - (z1-z5)^2 - l15^2 = 0 \\
(x1-x6)^2 - (y1-y6)^2 - (z1-z6)^2 - l16^2 = 0 \\
(x1-x7)^2 - (y1-y7)^2 - (z1-z7)^2 - l17^2 = 0 \\
(x2-x3)^2 - (y2-y3)^2 - (z2-z3)^2 - l23^2 = 0 \\
(x2-x4)^2 - (y2-y4)^2 - (z2-z4)^2 - l24^2 = 0 \\
(x2-x5)^2 - (y2-y5)^2 - (z2-z5)^2 - l25^2 = 0 \\
(x2-x6)^2 - (y2-y6)^2 - (z2-z6)^2 - l26^2 = 0 \\
(x2-x7)^2 - (y2-y7)^2 - (z2-z7)^2 - l27^2 = 0
\end{cases}$$

The embodiment may determine t0 through t7, s0 through s7, and the first 3-D position of the x-ray source 501 followed by calculation of coordinates of the strut connection points 503. The second 3-D positions of the x-ray source 501 and of the object 510 may be determined by using a substantially similar mathematical model discussed below, in which it is assumed that ('x,'y,'z) are coordinates of the x-ray source 501 and ('X0,'Y0,'Z0) to ('X1,'Y1,'Z1), . . . ('X6,'Y6,'Z6) to ('X7,'Y7,'Z7) are a second set of projections of longitudinal axes of the struts 506 on the second roentgenogram.

Furthermore, it is assumed that ('X'0,'Y'0,'Z'0) through ('X'7,'Y'7, 'Z'7) are coordinates of a second set of projections of the eight strut connection points 503 on the second roentgenogram, which may be represented in the following manner:

$'X'0 = 'X0 + 'v01x * 's0;$ $'Y'0 = 'Y0 + 'v01y * 's0;$ $'Z'0 = 'Z0 + 'v01z * 's0.$

Similar equations are determined for other strut connection points 503 to the fixation members 502.

The present embodiment employs the following parametric equations:

$$'x = x0 + \alpha * t;\ 'y = y0 + \beta * t;\ 'z = z0 + \gamma * t$$

The three points ('x,'y,'z), (xi, yi, zi), and ('X'i,'Y'i,'Z'i) are situated on the same line passing from the x-ray source 601, to the marker 603, and then to the imager 604. The parametric equations for this line may thus be expressed as:

$$xi = 'x + \alpha_i * t_i;\ yi = 'y + \beta_i * t_i;\ zi = 'z + \gamma_i * t_i$$

where:

$$\alpha_i = 'X'i - 'x;\ \beta_i = 'Y'i - 'y;\ \gamma_i = 'Z'i - 'z$$

The present embodiment determines 18 equations by adding appropriate number of equations for distances between the strut connection points on the ring. The resulting 18 equations are provided below:

$$\begin{cases}(x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0\end{cases}$$

The first and second 3-D positions of the x-ray source and of the object may thereby be found.

Model 8

In another embodiment of the technique, the plurality of struts 506 may comprise four struts. In the present embodiment, the first 3-D positions of the x-ray source 501 and of the object 510 may be determined by using the mathematical model discussed below, in which it is assumed that (x,y,z) are coordinates of the x-ray source 501, (x0,y0,z0) through (x7,y7,z7) are coordinates of the eight strut connection points 503 to the fixation members 502, (X0,Y0,Z0) to (X1,Y1,Z1), . . . (X6,Y6,Z6) to (X7,Y7,Z7) are a first set of projections of longitudinal axes of the struts 506 on the first roentgenogram, and l01, l02, l03, l04, l06, l07, l12, l13, l14, l15, l16, l17, l23, l24, l25, l26, l27 are the predetermined distances between the eight strut connection points 503. These relationships of variables are depicted in FIG. 6.

Furthermore, each strut connection point 503 is located on a plane that crosses the x-ray source 501 and projection of the longitudinal axis of the strut. Thus, one plane appurtenant equations may be determined for each strut connection point 503, creating a system of eight equations for the fixator with four struts 506 as provided below.

$$\begin{cases}\begin{vmatrix} x0-x & y0-y & z0-z \\ X0-x & Y0-x & Z0-z \\ X1-x & Y1-y & Z1-z \end{vmatrix} = 0 \\[2mm] \begin{vmatrix} x1-x & y1-y & z1-z \\ X0-x & Y0-x & Z0-z \\ X1-x & Y1-y & Z1-z \end{vmatrix} = 0 \\[2mm] \begin{vmatrix} x2-x & y2-y & z2-z \\ X2-x & Y2-x & Z2-z \\ X3-x & Y3-y & Z3-z \end{vmatrix} = 0 \\[2mm] \begin{vmatrix} x3-x & y3-y & z3-z \\ X2-x & Y2-x & Z2-z \\ X3-x & Y3-y & Z3-z \end{vmatrix} = 0 \\[2mm] \begin{vmatrix} x4-x & y4-y & z4-z \\ X4-x & Y4-x & Z4-z \\ X5-x & Y5-y & Z5-z \end{vmatrix} = 0 \\[2mm] \begin{vmatrix} x5-x & y5-y & z5-z \\ X4-x & Y4-x & Z4-z \\ X5-x & Y5-y & Z5-z \end{vmatrix} = 0 \\[2mm] \begin{vmatrix} x6-x & y6-y & z6-z \\ X6-x & Y6-x & Z6-z \\ X7-x & Y7-y & Z7-z \end{vmatrix} = 0 \\[2mm] \begin{vmatrix} x7-x & y7-y & z7-z \\ X6-x & Y6-x & Z6-z \\ X7-x & Y7-y & Z7-z \end{vmatrix} = 0\end{cases}$$

Now, by adding an appropriate number of equations for distances between the strut connection points (e.g., 18 equations for 18 distances between eight strut connection points of four struts of known geometry fixator), the embodiment provides the following mathematical model of 26 equations:

$$\begin{cases}\begin{vmatrix} x0-x & y0-y & z0-z \\ X0-x & Y0-x & Z0-z \\ X1-x & Y1-y & Z1-z \end{vmatrix} = 0 \\[2mm] \begin{vmatrix} x1-x & y1-y & z1-z \\ X0-x & Y0-x & Z0-z \\ X1-x & Y1-y & Z1-z \end{vmatrix} = 0 \\[2mm] \begin{vmatrix} x2-x & y2-y & z2-z \\ X2-x & Y2-x & Z2-z \\ X3-x & Y3-y & Z3-z \end{vmatrix} = 0 \\[2mm] \begin{vmatrix} x3-x & y3-y & z3-z \\ X2-x & Y2-x & Z2-z \\ X3-x & Y3-y & Z3-z \end{vmatrix} = 0 \\[2mm] \begin{vmatrix} x4-x & y4-y & z4-z \\ X4-x & Y4-x & Z4-z \\ X5-x & Y5-y & Z5-z \end{vmatrix} = 0\end{cases}$$

-continued $$\begin{vmatrix} x5-x & y5-y & z5-z \\ X4-x & Y4-x & Z4-z \\ X5-x & Y5-y & Z5-z \end{vmatrix} = 0$$

$$\begin{vmatrix} x6-x & y6-y & z6-z \\ X6-x & Y6-x & Z6-z \\ X7-x & Y7-y & Z7-z \end{vmatrix} = 0$$

$$\begin{vmatrix} x7-x & y7-y & z7-z \\ X6-x & Y6-x & Z6-z \\ X7-x & Y7-y & Z7-z \end{vmatrix} = 0$$

$(x0-x1)^2 - (y0-y1)^2 - (z0-z1)^2 - l01^2 = 0$ $(x0-x2)^2 - (y0-y2)^2 - (z0-z2)^2 - l02^2 = 0$ $(x0-x3)^2 - (y0-y3)^2 - (z0-z3)^2 - l03^2 = 0$ $(x0-x4)^2 - (y0-y4)^2 - (z0-z4)^2 - l04^2 = 0$ $(x0-x5)^2 - (y0-y5)^2 - (z0-z5)^2 - l05^2 = 0$ $(x0-x6)^2 - (y0-y6)^2 - (z0-z6)^2 - l06^2 = 0$ $(x0-x7)^2 - (y0-y7)^2 - (z0-z7)^2 - l07^2 = 0$ $(x1-x2)^2 - (y1-y2)^2 - (z1-z2)^2 - l12^2 = 0$ $(x1-x3)^2 - (y1-y3)^2 - (z1-z3)^2 - l13^2 = 0$ $(x1-x4)^2 - (y1-y4)^2 - (z1-z4)^2 - l14^2 = 0$ $(x1-x5)^2 - (y1-y5)^2 - (z1-z5)^2 - l15^2 = 0$ $(x1-x6)^2 - (y1-y6)^2 - (z1-z6)^2 - l16^2 = 0$ $(x1-x7)^2 - (y1-y7)^2 - (z1-z7)^2 - l17^2 = 0$ $(x2-x3)^2 - (y2-y3)^2 - (z2-z3)^2 - l23^2 = 0$ $(x2-x4)^2 - (y2-y4)^2 - (z2-z4)^2 - l24^2 = 0$ $(x2-x5)^2 - (y2-y5)^2 - (z2-z5)^2 - l25^2 = 0$ $(x2-x6)^2 - (y2-y6)^2 - (z2-z6)^2 - l26^2 = 0$ $(x2-x7)^2 - (y2-y7)^2 - (z2-z7)^2 - l27^2 = 0$

The first 3-D positions of the x-ray source 501 and of the object 510 may be determined by solving for the equations above. The second 3-D positions of the x-ray source 501 and of the object 510 may be determined by using a substantially similar mathematical model discussed below, in which it is assumed that ('x,'y,'z) are coordinates of the x-ray source 501 and ('X0,'Y0,'Z0) to ('X1,'Y1,'Z1), . . . ('X6,'Y6,'Z6) to ('X7,'Y7,'Z7) are a second set of projections of the four struts on the second roentgenogram:

$$\begin{vmatrix} x0-'x & y0-'y & z0-'z \\ 'X0-'x & 'Y0-'x & 'Z0-'z \\ 'X1-'x & 'Y1-'y & 'Z1-'z \end{vmatrix} = 0$$

$$\begin{vmatrix} x1-'x & y1-'y & z1-'z \\ 'X0-'x & 'Y0-'x & 'Z0-'z \\ 'X1-'x & 'Y1-'y & 'Z1-'z \end{vmatrix} = 0$$

$$\begin{vmatrix} x2-'x & y2-'y & z2-'z \\ 'X2-'x & 'Y2-'x & 'Z2-'z \\ 'X3-'x & 'Y3-'y & 'Z3-'z \end{vmatrix} = 0$$

$$\begin{vmatrix} x3-'x & y3-'y & z3-'z \\ 'X2-'x & 'Y2-'x & 'Z2-'z \\ 'X3-'x & 'Y3-'y & 'Z3-'z \end{vmatrix} = 0$$

$$\begin{vmatrix} x4-'x & y4-'y & z4-'z \\ 'X4-'x & 'Y4-'x & 'Z4-'z \\ 'X5-'x & 'Y5-'y & 'Z5-'z \end{vmatrix} = 0$$

$$\begin{vmatrix} x5-'x & y5-'y & z5-'z \\ 'X4-'x & 'Y4-'x & 'Z4-'z \\ 'X5-'x & 'Y5-'y & 'Z5-'z \end{vmatrix} = 0$$

$$\begin{vmatrix} x6-'x & y6-'y & z6-'z \\ 'X6-'x & 'Y6-'x & 'Z6-'z \\ 'X7-'x & 'Y7-'y & 'Z7-'z \end{vmatrix} = 0$$

$$\begin{vmatrix} x7-'x & y7-'y & z7-'z \\ 'X6-'x & 'Y6-'x & 'Z6-'z \\ 'X7-'x & 'Y7-'y & 'Z7-'z \end{vmatrix} = 0$$

$(x0-x1)^2 - (y0-y1)^2 - (z0-z1)^2 - l01^2 = 0$ $(x0-x2)^2 - (y0-y2)^2 - (z0-z2)^2 - l02^2 = 0$ $(x0-x3)^2 - (y0-y3)^2 - (z0-z3)^2 - l03^2 = 0$ $(x0-x4)^2 - (y0-y4)^2 - (z0-z4)^2 - l04^2 = 0$ $(x0-x5)^2 - (y0-y5)^2 - (z0-z5)^2 - l05^2 = 0$ $(x0-x6)^2 - (y0-y6)^2 - (z0-z6)^2 - l06^2 = 0$ $(x0-x7)^2 - (y0-y7)^2 - (z0-z7)^2 - l07^2 = 0$ $(x1-x2)^2 - (y1-y2)^2 - (z1-z2)^2 - l12^2 = 0$ $(x1-x3)^2 - (y1-y3)^2 - (z1-z3)^2 - l13^2 = 0$ $(x1-x4)^2 - (y1-y4)^2 - (z1-z4)^2 - l14^2 = 0$ $(x1-x5)^2 - (y1-y5)^2 - (z1-z5)^2 - l15^2 = 0$ $(x1-x6)^2 - (y1-y6)^2 - (z1-z6)^2 - l16^2 = 0$ $(x1-x7)^2 - (y1-y7)^2 - (z1-z7)^2 - l17^2 = 0$ $(x2-x3)^2 - (y2-y3)^2 - (z2-z3)^2 - l23^2 = 0$ $(x2-x4)^2 - (y2-y4)^2 - (z2-z4)^2 - l24^2 = 0$ $(x2-x5)^2 - (y2-y5)^2 - (z2-z5)^2 - l25^2 = 0$ $(x2-x6)^2 - (y2-y6)^2 - (z2-z6)^2 - l26^2 = 0$ $(x2-x7)^2 - (y2-y7)^2 - (z2-z7)^2 - l27^2 = 0$

The first and second 3-D positions of the x-ray source 501 and of the object 510 may thereby be determined.

Approximating the Location of the X-Ray Source

It is to be appreciated that in some cases, the resolution of the first and second roentgenograms may not be enough to allow one to precisely identify the positions of the shadows created by the markers on the respective roentgenograms. With reference to FIG. 2B, small errors may exist and cause the vectors/trajectories (e.g., 242 and 244) to misalign and not intersect. In such cases, the position of the x-ray source 202 may be determined using an approximation model. According to an exemplary approximation model, the orientation and position of a segment between the vectors/trajectories 242 and 244 may be determined, and a point on the segment may be chosen to represent the position of the x-ray source 202. In an embodiment, the segment chosen may be a common perpendicular of the vectors/trajectories 242 and 244, and the midpoint of the common perpendicular may be chosen to represent the position of the x-ray source 202. It is to be appreciated that while a common perpendicular of both vectors/trajectories 242 and 244 may be the shortest segment between the vectors/trajectories 242 and 244 and may allow for an accurate approximation of the x-ray source 202, other segments may also be chosen, depending on the desired accuracy of the approximation model.

In an exemplary embodiment, the common perpendicular of the vectors/trajectories 242 and 244 may be determined by using the mathematical model discussed below, in which it is assumed that $(x^1_1, y^1_1, z^1_1)$ are the coordinates of the marker 1 shadow (250), $(x^1_2, Y^1_2, z^1_2)$ are the coordinates of the marker 1 (252), $(x^2_1, y^2_1, z^2_1)$ are the coordinates of the marker 2 shadow (254), $(x^2_2, y^2_2, z^2_2)$ are the coordinates of marker 2 (256). The equation for the first line 242 may thus be expressed as:

$$\frac{x - x^1_2}{x^1_2 - x^1_1} = \frac{y - y^1_2}{y^1_2 - y^1_1} = \frac{z - z^1_2}{z^1_2 - z^1_1}$$

and the equation for the second line 244 may be expressed as:

$$\frac{x - x^2_2}{x^2_2 - x^2_1} = \frac{y - y^2_2}{y^2_2 - y^2_1} = \frac{z - z^2_2}{z^2_2 - z^2_1}$$

The resulting vectors of the first line 242 and second line 244 may respectively be represented as:

$\vec{a} = (a_1, a_2, a_3)$ $\vec{b} = (b_1, b_2, b_3)$ where:

$a_1 = x_2^1 - x_1^1$ $a_2 = y_2^1 - y_1^1$ $a_3 = z_2^1 - z_1^1$ $b_1 = x_2^2 - x_1^2$ $b_2 = y_2^2 - y_1^2$ $b_3 = z_2^2 - z_1^2$

Multiplying vectors a and b according to the equation below would provide a vector c that is perpendicular both lines 242 and 244:

$$\vec{c} = [\vec{a} \times \vec{b}] = \begin{vmatrix} \vec{i} & \vec{j} & \vec{k} \\ a_1 & a_2 & a_3 \\ b_1 & b_2 & b_3 \end{vmatrix} =$$

$$\vec{i} * (a_2 * b_3 - b_2 * a_3) + \vec{j} * (b_1 * a_3 - a_1 * b_3) + \vec{k} * (a_1 * b_2 - b_1 * a_2)$$

Where i, j, and k are unit vectors directed along the coordinate axes x, y, and z.

$\vec{c} = (c_1, c_2, c_3)$ $c_1 = (a_2 * b_3 - b_2 * a_3)$ $c_2 = (b_1 * a_3 - a_1 * b_3)$ $c_3 = (a_1 * b_2 - b_1 * a_2)$ In an embodiment, approximating the location of the x-ray source 202 may involve defining a segment S that lies in vector c and connects lines 242 and 244. As such, the segment S is a common perpendicular to the lines 242 and 244. One way of doing so is to build a plane D that includes marker 1 shadow (250), the first line 242, and the vector c. A perpendicular vector to such a plane D is the product of vector multiplication $[\vec{a} \times \vec{c}]$, and may be expressed as:

$$\vec{n}' = [\vec{a} \times \vec{b}] = \begin{vmatrix} \vec{i} & \vec{j} & \vec{k} \\ a_1 & a_2 & a_3 \\ c_1 & c_2 & c_3 \end{vmatrix} =$$

$$\vec{i} * (a_2 * c_3 - c_2 * a_3) + \vec{j} * (c_1 * a_3 - a_1 * c_3) + \vec{k} * (a_1 * c_2 - c_1 * a_2)$$

$n'_1 = (a_2 * c_3 - c_2 * a_3)$ $n'_2 = (c_1 * a_3 - a_1 * c_3)$ $n'_3 = (a_1 * c_2 - c_1 * a_2)$

This vector can be normalized with respect to a unit length and expressed as:

$$\vec{n} = \frac{\vec{n}'}{\|\vec{n}'\|}$$

$$\|\vec{n}'\| = \sqrt{(n'_1)^2 + (n'_2)^2 + (n'_3)^2}$$

$$n_1 = \frac{(a_2 * c_3 - c_2 * a_3)}{\|\vec{n}'\|}$$

$$n_2 = \frac{(c_1 * a_3 - a_1 * c_3)}{\|\vec{n}'\|}$$

$$n_3 = \frac{(a_1 * c_2 - c_1 * a_2)}{\|\vec{n}'\|}$$

A plane D going through marker 1 shadow (250) having coordinates $(x_1^1, y_1^1, z_1^1)$ and having a perpendicular vector $\vec{n} = (n_1, n_2, n_3)$ may thus be represented by the following equations:

$n_1 * x + n_2 * y + n_3 * z + D = 0$ $D = n_1 * x_1^1 + n_2 * y_1^1 + n_3 * z_1^1$

One of the endpoints of the segment S may be the crossing point where the plane D intersects with line 244. To determine the location of this crossing point, a right triangle may be drawn such that its hypotenuse G extends along line 244 and connects the marker 2 shadow 254 and the crossing point at which line 244 intersects the plane D. Furthermore, a first leg R of the right triangle may be defined by a vector r perpendicular to plane D and extending from the marker 2 shadow 254 to the plane D. The second leg of the right triangle may be defined by the projection of the hypotenuse G in the plane D.

The length of the first leg R, which is distance between marker 2 shadow 254 and the plane D, may be determined by a scalar multiplication of plane D's normalized perpendicular vector n and the vector r. In this case, the product of this scalar multiplication may be expressed in terms of the coordinates of the "marker 2 shadow 254" as illustrated in the following equation:

$R = (\vec{n} \cdot \vec{r}) = n_1 \cdot x_1^2 + n_2 \cdot y_1^2 + n_3 \cdot z_1^2$ Furthermore, the cosine of the angle φ between the vector r and the vector b may be expressed as:

$$\cos\phi = \frac{(\vec{b}\cdot\vec{n})}{|\vec{b}|\cdot|\vec{n}|} = \frac{b_1*n_1 + b_2*n_2 + b_3*n_3}{\sqrt{(b_1)^2 + (b_2)^2 + (b_3)^2} * \sqrt{(n_1)^2 + (n_2)^2 + (n_3)^2}}$$

Accordingly, the length of the hypotenuse G can be determined by dividing the length of the first leg R by the cosine of the angle between the first leg R and hypotenuse G:

$$G = \frac{R}{|\cos\phi|}$$

In order to find coordinates of the crossing point where line 244 intersects the plane D, a vector $\vec{L}$ extending along line 244 may be defined from the marker 2 shadow 254 and a length of G:

$$\vec{L} = G*\frac{\vec{b}}{\|\vec{b}\|} = \vec{i}*\frac{G*b_1}{\sqrt{(b_1)^2+(b_2)^2+(b_3)^2}} +$$
$$\vec{j}*\frac{G*b_2}{\sqrt{(b_1)^2+(b_2)^2+(b_3)^2}} + \vec{k}*\frac{G*b_3}{\sqrt{(b_1)^2+(b_2)^2+(b_3)^2}}$$

$$\vec{L} = \vec{i}*L_1 + \vec{j}*L_2 * \vec{k}*L_3$$

where $x' = x_1^2 + L_1$ $y' = y_1^2 + L_2$ $z' = z_1^2 + L_3$

These coordinates define one of the endpoints of segment S. In order to find coordinates of the second endpoint of segment S, similar calculations may be performed. In an embodiment, a plane may be defined along the line 244 and finding the crossing point of this plane on the line 244. In an embodiment, after defining the endpoints of the segment S, the positioning of the x-ray source 202 may be approximated to be located in the middle of segment S and calculated as the mean of those coordinates:

$$x_{light} = \frac{x'+x''}{2}$$

$$y_{light} = \frac{y'+y''}{2}$$

$$z_{light} = \frac{z''+z''}{2}$$

It is to be appreciated that in other embodiments, the approximated location of the x-ray source 202 may be anywhere between the endpoints of the segment S. It is to be further appreciated that while the above discussed exemplary mathematical model provides an efficient and precise method of approximating the location of x-ray source 202, other suitable models according to the principles of the present disclosure may also be used to approximate the location of x-ray source 202.

Figure 12A:
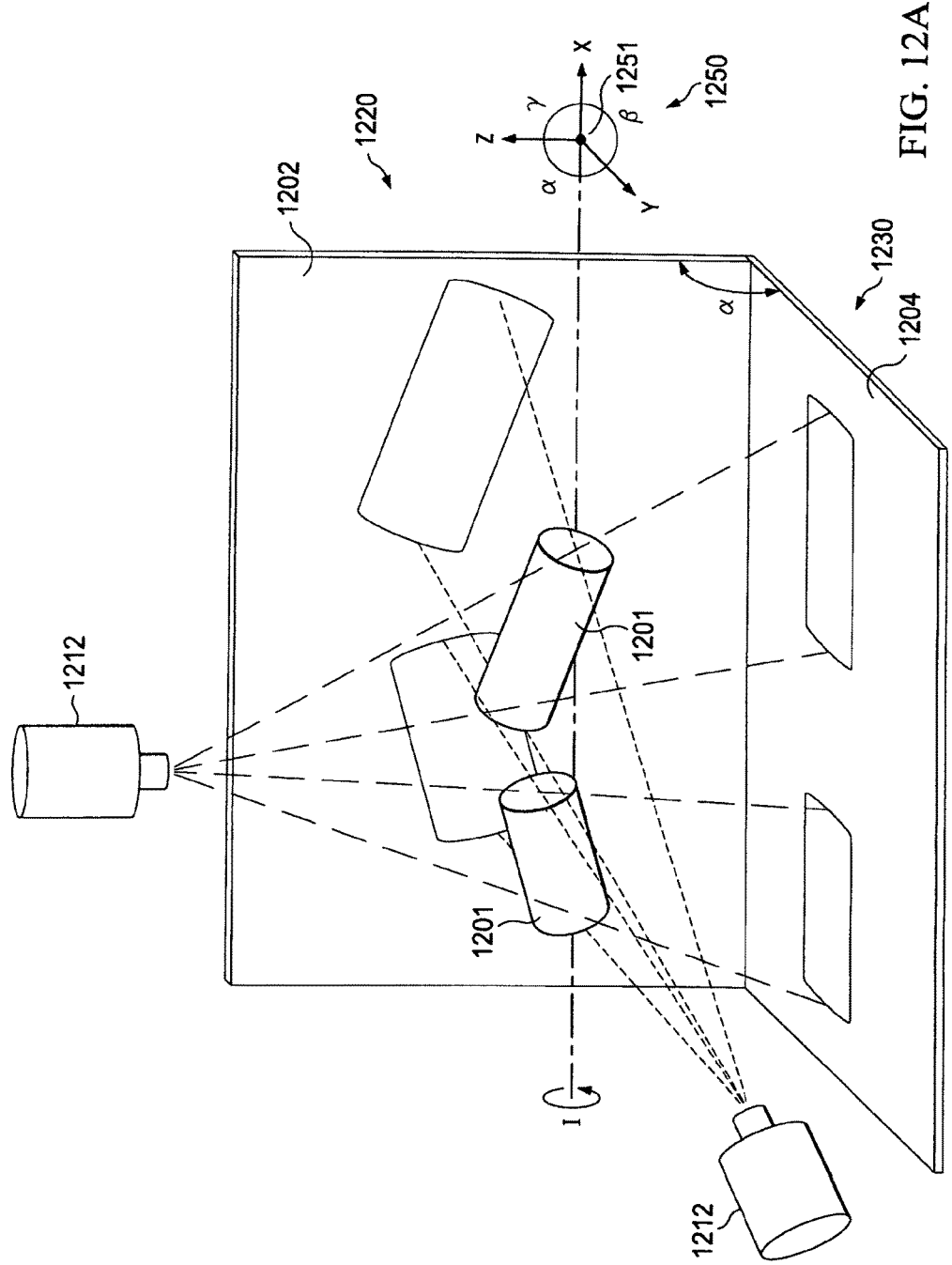
FIG. 12A is a schematic diagram illustrating first and second roentgenograms of an object, in accordance with the present disclosure.

Once the 3-D location of the x-ray source 202 in the first and second imaging orientations (220, 230) has been identified, a variety of different techniques can be used to create a 3-D model of the imaged object. According to one embodiment, the amount of angular displacement about the imaging axis I between the first imaging orientation 220 and the second imaging orientation 230 is known. Illustrations corresponding to this embodiment are depicted in FIGS. 12A-12G. FIG. 12A depicts objects 1201 that are being imaged at two orientations (1220, 1230). The images at the two relative orientations (1220, 1230) can be prepared by either rotating the imaged object 1201 about an imaging axis I by angular displacement α, or by rotating the x-ray source and the imager about the imaging axis I by an angular displacement α. Preferably but not required, the imaging axis I is parallel to the plane of the x-ray imager (not shown) in the first orientation 1220 and to the plane of the x-ray imager in the second orientation 1230. Creating these images at two orientations will result in two roentgenograms (1202, 1204) that correspond to orientations 1220, 1230, respectively. Also shown in FIG. 12A are the relative positions of the x-ray sources 1212 with respect to the roentgenograms (1202, 1204). The 3-D positions of these x-ray sources 1212 may be determined based upon the shadows created by the reference markers on the roentgenograms (1202, 1204), as described above, or by any other techniques known in the art, such as physically measuring the position of the x-ray source 1212 with respect to the imager 104.

Figure 12B:
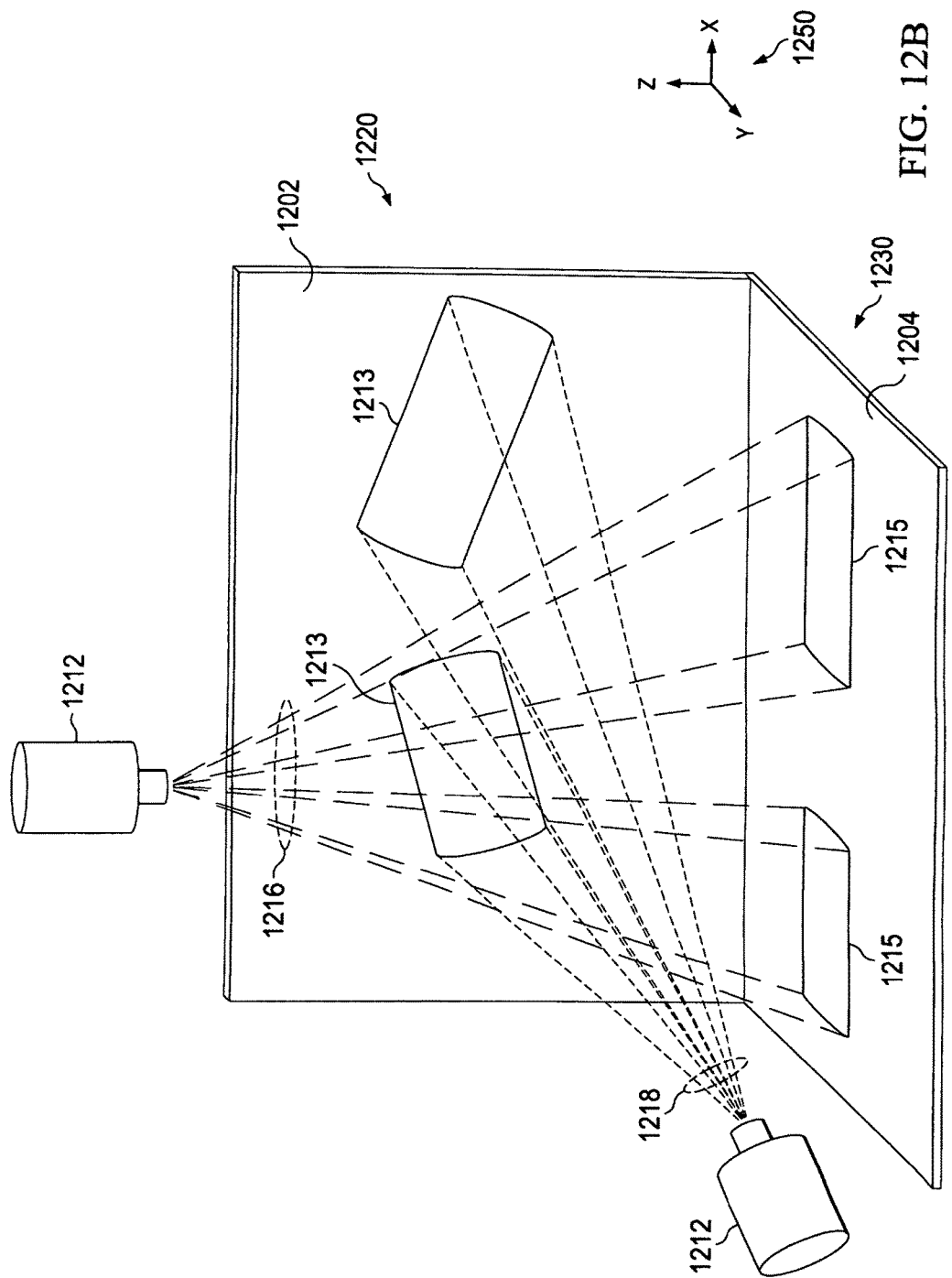
FIG. 12B is a schematic diagram illustrating the orientations of a light source and the corresponding roentgenograms shown in FIG. 12A, in accordance with the present disclosure.

Another step in the creation of a 3-D model of the objects 1201 is to determine the outline of the imaged objects 1201 in the roentgenograms. This concept is depicted in FIG. 12B, in which the outlines of the imaged object in the first roentgenogram 1202 have been identified as outlines 1213. Similarly, the outlines of the imaged object in the second roentgenogram 1204 have been identified as outlines 1215. Where the roentgenograms are digital images stored in a computer system, this process can be performed automatically by using image-processing software. According to another embodiment, this process can be performed manually by tracing the outline of the imaged object in the roentgenograms with a mouse, a stylus, or any other tracing device. After determining the outline of the imaged object and the 3-D position of the x-ray source 1212, a projection of the outline of the imaged object can be created. The projection of the object outline 1213 in the first orientation 120 is depicted in FIG. 12B by projection lines 308, which pass from the outline 1213 in the first roentgenogram 1202 to the 3-D position of the x-ray source 1212 in the first orientation 1220. Similarly, the projection of the object outline 1215 in the second orientation 1230 is depicted in FIG. 12B by projection lines 1216, which pass from the outline 1215 in the second roentgenogram 1204 to the 3-D position of the x-ray source 1212 in the second orientation 1230.

Once the projections of the imaged objects have been created for the first and second orientations (1220, 1230), the relative position of the orientations (1220, 1230) with respect to each other may be used to determine how those projections intersect with each other. This can be done in a variety of ways. According to one embodiment, the 3-D projections may be combined into a single 3-D reference frame corresponding to the x, y, z reference frame 1250 depicted in FIGS. 12A-12E. The origin for the x, y, z reference frame 1250 may be located along the imaging axis I at point 1251 where the x-rays from the x-ray source 1212 in the first orientation 1220 intersect the imaging axis orthogonally and the x-rays from the x-ray source 1212 in the second orientation 1230 intersect the imaging axis orthogonally. As discussed above, in this reference frame 1250, angle α corresponds to angular displacement between the two orientations (1220, 1230) about the x axis, or the imaging axis I. This angle α can be determined in a variety of ways. In the embodiment where x-ray source 1212 and the imager are stationary and the object is rotated, the angle α corresponds to the amount of rotation of the object about the x-axis or imaging axis I, as shown in FIGS. 2A and 2B. In an alternative embodiment where the object remains stationary, but the x-ray source 1212 and the imager are rotated about the object, the angle α corresponds to the amount of rotation of the x-ray source 1212 and the imager about the imaging axis I shown in FIGS. 2A and 2B. When rotating the x-ray source 1212 and the imager about the imaged objects 1201, it may be preferred, but not required, that the position of the x-ray source 1212 be fixed with respect to the position of the imager. Further, it may be preferred, but not required, that the roentgenograms (1202, 1204) be taken at orientations (1220, 1230) that are substantially orthogonal with respect to each other. Using the angular displacement α and the projections of the outlines described above, the relative positions of the roentgenograms (1202, 1204) and their corresponding projections can be aligned with each other.

The angles β and γ correspond to the angular displacement of the first roentgenogram 1202 with respect to the second roentgenograms 1204 about the z- and y-axes, respectively. As discussed above, in some embodiments, the first and second relative orientations 1220 and 1230 are substantially orthogonal with respect to each other, and in these embodiments, the angles β and γ may be substantially zero. In embodiments in which first and second relative orientations 1220 and 1230 are not substantially orthogonal, first and second roentgenograms (1202, 1204) may be further aligned at angles β and γ using a variety of approaches, including the iterative approaches to be described in the present disclosure. It is to be appreciated that while it is optional to align the roentgenograms (1202, 1204) at angles β and γ, doing so may allow for a more accurate 3-D model of the object 1201.

Figure 12C:
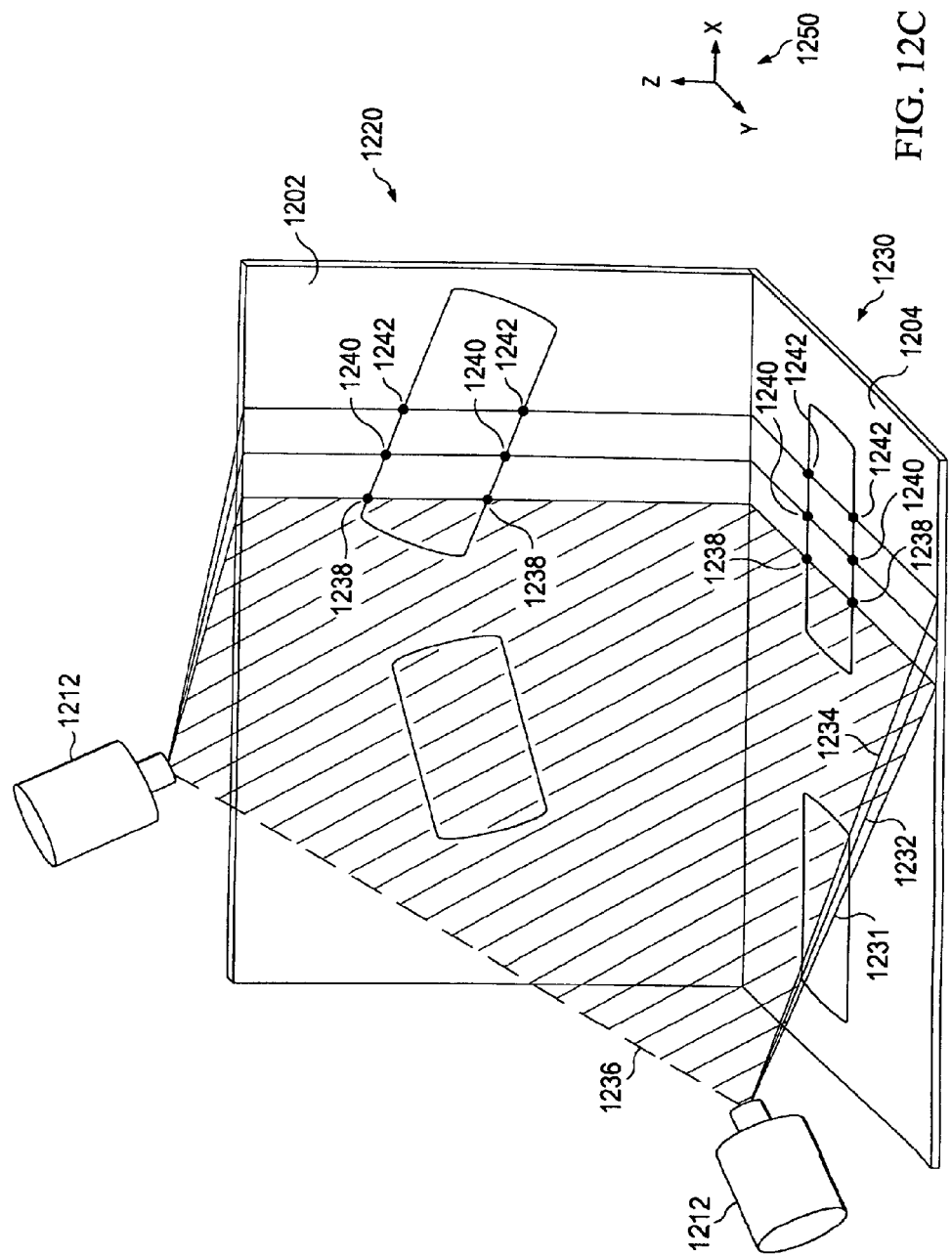
FIG. 12C is a schematic diagram illustrating a plurality of intersection planes each passing through a tilt axis and the first and second roentgenograms shown in FIG. 12A, in accordance with the present disclosure.

FIG. 12C illustrates that the roentgenograms (1202, 1204) of the imaged objects 1201, as well as the 3-D object projections of the imaged objects 1201, may be intersected by a plurality of planes, including planes 1231, 1232, and 1234. Each of these planes pass through a first 3-D position in the 3-D reference frame that corresponds to the location of the x-ray source 1212 in the first orientation 1220, and a second 3-D position in the 3-D reference frame that corresponds to the location of the x-ray source 1212 in the second orientation 1230. FIG. 12C also depicts a tilt axis 1236 that passes between the first and second 3-D positions in the 3-D reference frame. Each of the planes 1231, 1232, and 1234 has a different tilt about the tilt axis 1236, such that they intersect the outlines of the imaged object 1201 in the first and second roentgenograms (1202, 1204). The location of the intersections between plane 1231 and the image outlines in the first and second roentgenograms (1202, 1204) is marked with points 318. The location of the intersections between plane 1232 and the image outlines in the first and second roentgenograms (1202, 1204) is marked with points 1240. The location of the intersections between plane 1234 and the image outlines in the first and second roentgenograms (1202, 1204) is marked with points 1244.

Figure 12D:
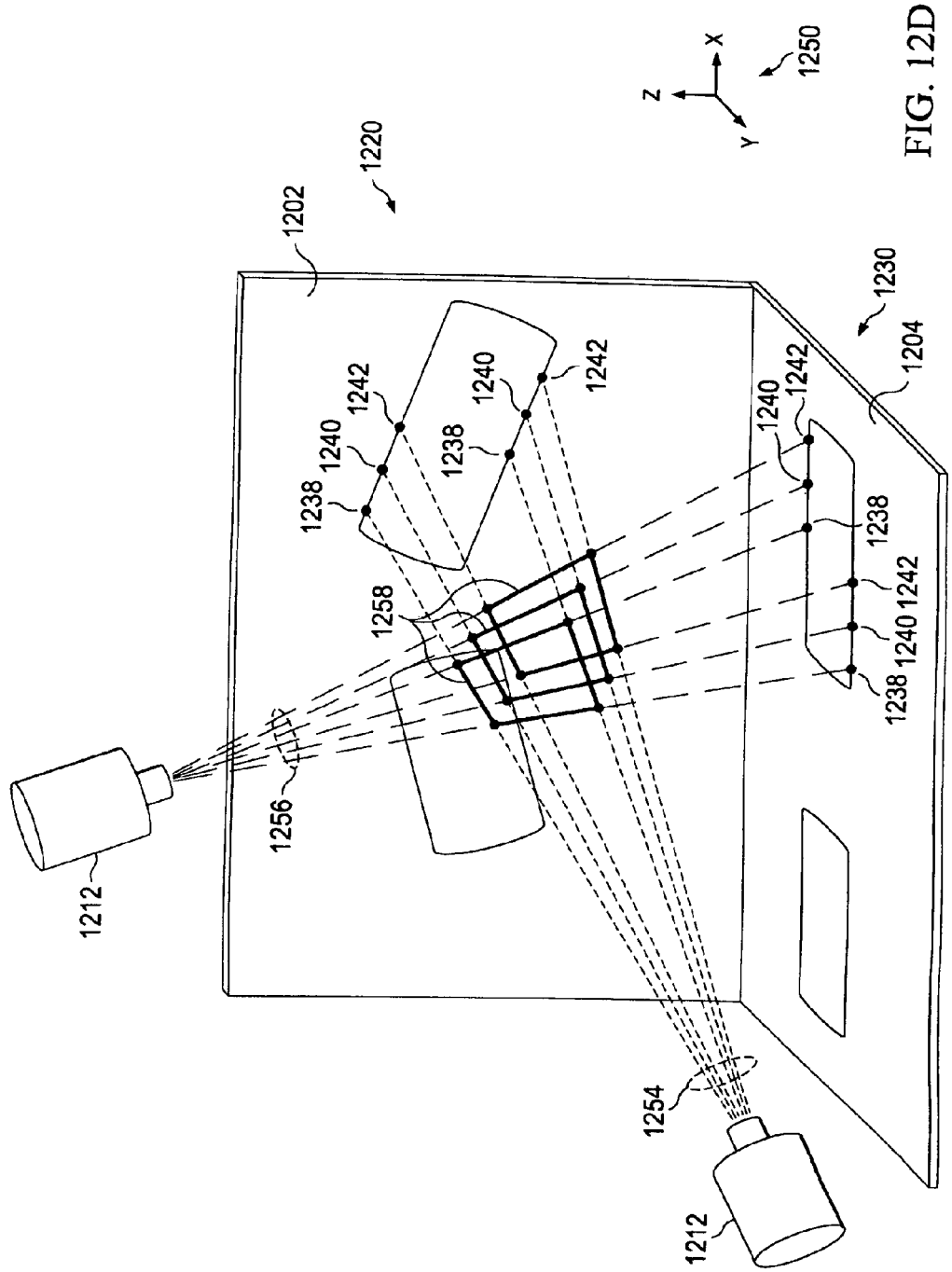
FIG. 12D is a schematic diagram illustrating a plurality of intersection points between the 3 D object projections from the first and second roentgenograms shown in FIG. 12A, in accordance with the present disclosure.

In FIG. 12D, each of the intersection points 1238, 1240, and 1242 is connected to the location of the x-ray source 1212 in the 3-D reference frame 1250 at the corresponding orientations (120, 150). Accordingly, intersection points 1238, 1240, and 1242 in roentgenogram 1202 are connected by lines 324 to the first 3-D location in the 3-D reference frame 1250, which corresponds to the location of the x-ray source 1212 in the first orientation 1220. Similarly, intersection points 1238, 1240, and 1242 in roentgenogram 1204 are connected by lines 1256 to the second 3-D location in the 3-D reference frame 1250, which corresponds to the location of the x-ray source 1212 in the second orientation 1230. The four lines intersecting the set of points 1238 in the first and second roentgenograms (1202, 1204) also intersect with each other to form a polygon 1258 in 3-D reference frame 1250. Similarly, the four lines intersecting the set of points 1240 in the first and second roentgenograms (1202, 1204) also intersect with each other to form a polygon 1258 in 3-D reference frame 1250. Further, the four lines intersecting the set of points 1242 in the first and second roentgenograms (1202, 1204) also intersect with each other to form a polygon 1258 in 3-D reference frame 1250.

In FIG. 12E, the process of defining the polygons 1258 may repeated for one or more planes aligned with the tilt axis 1236 until a sufficient resolution is reached, or no further intersections with the imaged objects 1201 are identified. Each of these polygons 1258 corresponds to the intersection between the 3-D object projections in the first and second orientations (1202, 1204) in the 3-D reference frame 1250.

Figure 12F:
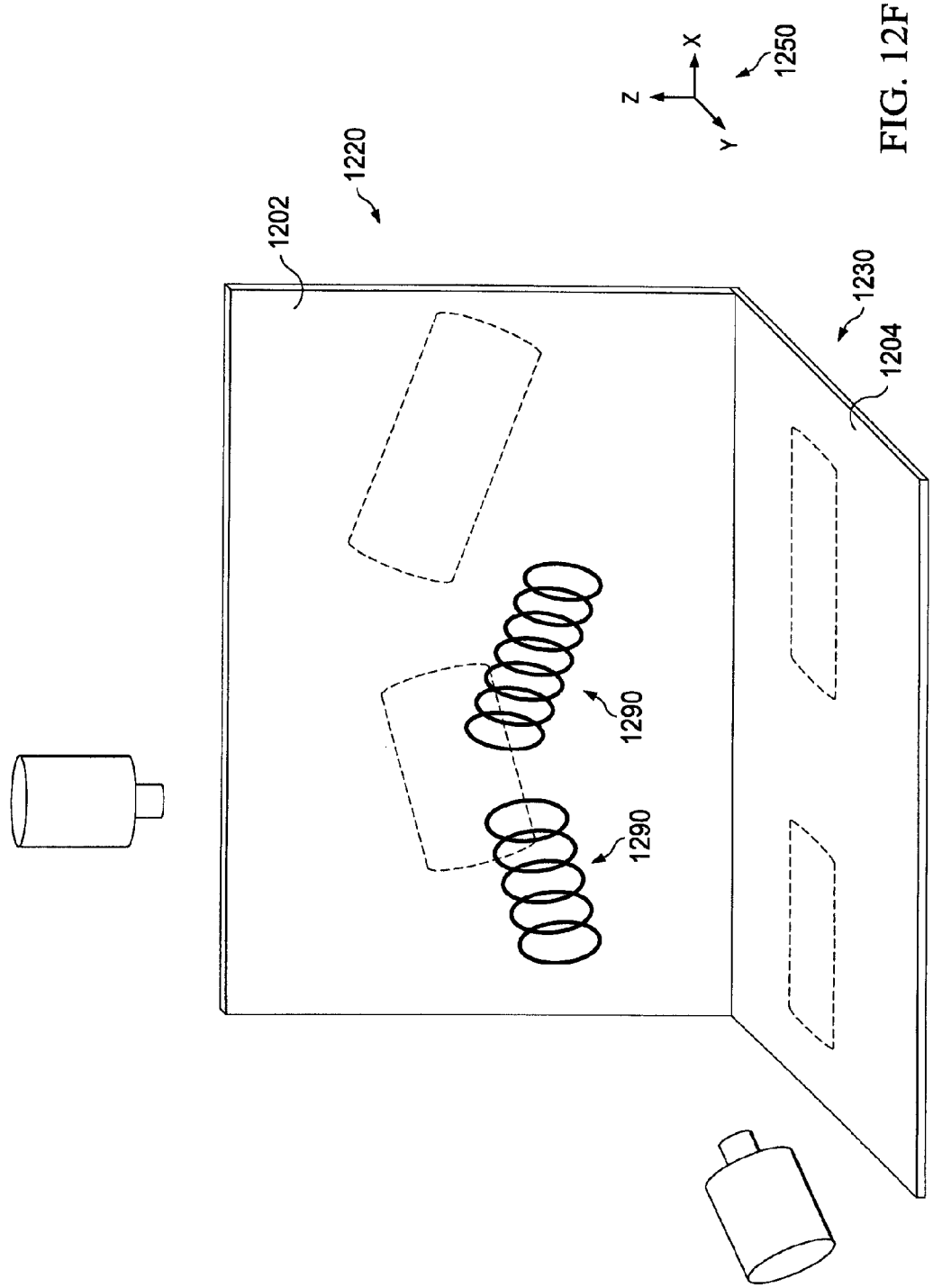
FIG. 12F is a schematic diagram illustrating a plurality of one or more closed curves within the each of the one or more polygons shown in FIG. 12E, in accordance with the present disclosure.

After creating a series of polygons 1258 corresponding to the intersections of the 3-D projections, the polygons 1258 may be converted into closed curves (e.g., ellipses) 1290 that correspond to the cross section shape of the imaged objects 1201 depicted in FIG. 12F. It is preferred, but not required, that the general shape and orientation of the imaged objects 1201 be known before converting the series of polygons 1258 into closed curves 1290. For example, if the imaged object, such a bone, has a generally elliptical cross-sectional shape, then the polygons 1258 can be replaced with closed curves 1290, such as ellipses, that are located within each of the polygons. On the other hand, if the imaged object has a non-symmetrical shape, then other information about the imaged object (e.g., its shape, cross-section, orientation, etc.) can be used to create an accurate 3-D model of the object. Once the polygons 1258 have been replaced with corresponding shapes (e.g., closed curves or ellipses) 1290, a surface connecting these shapes can be prepared. This surface may represent an accurate 3-D model 1292 of the imaged object, as shown in FIG. 12G. In some embodiments, the accuracy of the 3-D model 332 may be enhanced by modifying the model 1292 according to known shapes stored in an image library.

As discussed above, if the first and second relative orientations 1220 and 1230 are not substantially orthogonal, angles β and γ may be determined using iterative approach in accordance to the principles of the present disclosure. In an exemplary embodiment, roentgenograms (1202, 1204) may be orientated at angles β and γ by first aligning roentgenograms (1202, 1204) at a known α, and then creating various test 3-D models of the imaged objects 1201 by aligning roentgenograms (1202, 1204) at various angle β and γ, and finally identifying a 3-D model that would produce 2-D projections that substantially match the outlines of the imaged object 1201 in the first and second roentgenogram 1202 and 1204. The test models of the objects 1201 may be created according to the approach described above with respect to FIGS. 12C-12G to provide better accuracy. It is to be appreciated, however, that the various test models may be generated according to any suitable modeling technique known in the art.

According to another embodiment, a 3-D model of an object can be created in a fixed reference frame even when the angular displacement α between two imaging orientations (1220, 1230) is not known. Illustrations corresponding to this embodiment are depicted in FIGS. 13A-13E. Much like the previously described process in which the angular displacement α is known, two roentgenograms are prepared of the object at different orientations. Each of these roentgenograms includes an image of the object 1301 with object markers attached thereto. The at least one object marker 1342 may be attached to the object 1301 directly or indirectly, and the number of object markers 1342 may vary depending on the number fiducials each contains. In an exemplary embodiment, a total of at least three fiducials are included in the at least one object marker 1342. The at least three fiducials may be enclosed in one object marker 1342, or distributed among a plurality of object markers 1342, such as two or three object markers 1342. In another exemplary embodiment, a total of four or more fiducials are included in the least one object marker 1342, and the four or more fiducials may be enclosed in one marker 1342 or distributed among a plurality of object markers 1342, such as, two, three, four, or more, depending on the specific number of fiducials.

Figure 13A:
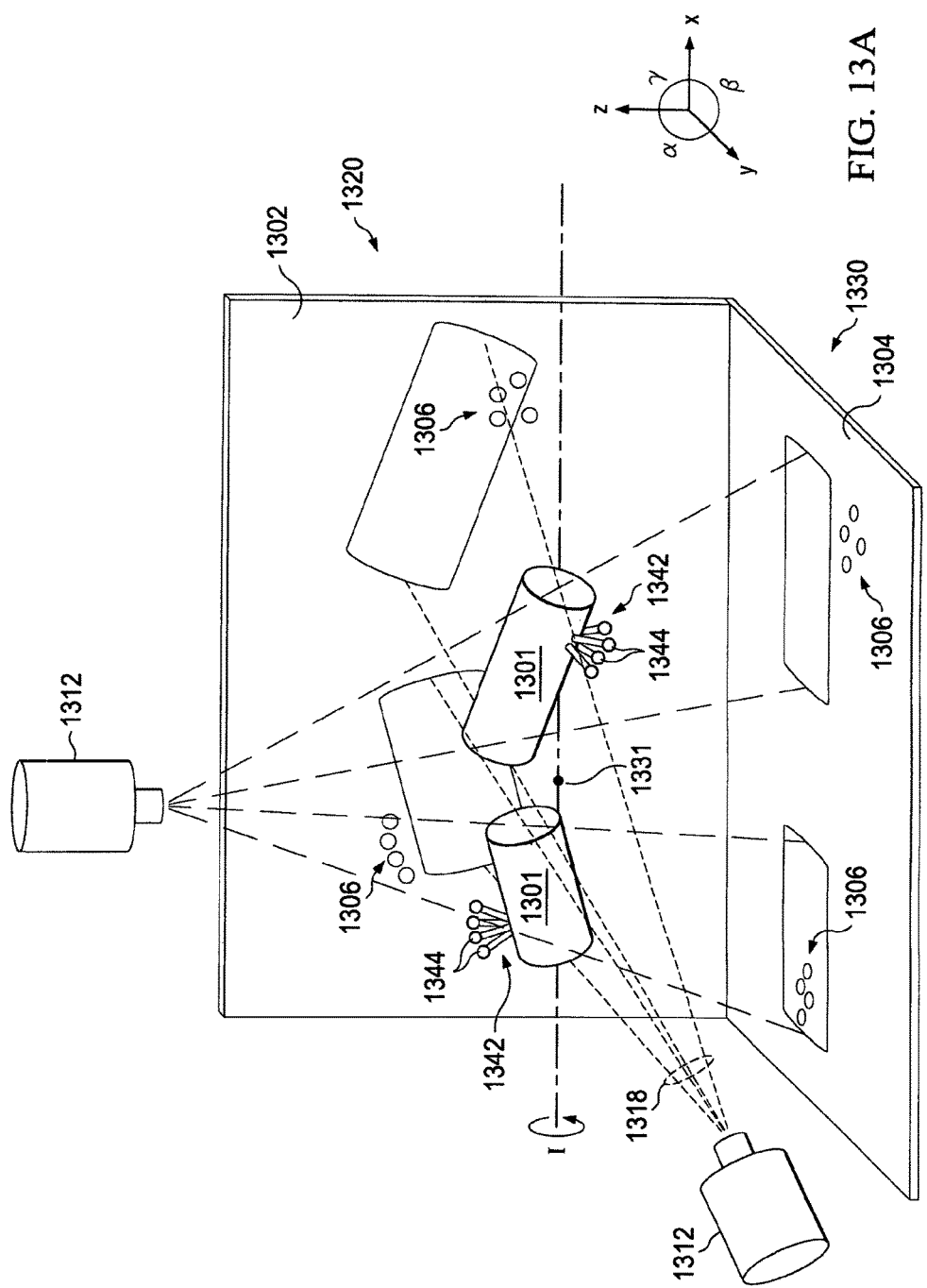
FIG. 13A is a schematic diagram illustrating a plurality of object markers being attached to an object, in accordance with the present disclosure.

An illustration of objects 1301 with representative object markers 1342 attached thereto is depicted in FIG. 13A. In FIG. 13A, imaged objects 1301 each include four object markers 1342 attached thereto, and each of these object markers 1342 includes a fiducial 1344. According to a first approach of using the object marker 1342 to create a model of objects 1301 in a fixed reference frame, the number and type of the object marker 1342 may vary as long as there are at least three fiducials 1344 directly or indirectly attached to at least one of the imaged objects 1301. For example, in an embodiment, one object marker 1342 may comprise three fiducials 1344. In another exemplary embodiment, two object markers 1342 may be used, each comprising two fiducials 1344. In yet another exemplary embodiment, three object markers 1342 may be used, each comprising one fiducial 1344. While three fiducials 1344 may be used in some embodiments, it is to be appreciated that embodiments using four or more fiducials 1344 may be more desirable for reasons to be discussed below. It is to be further appreciated that according to the first approach of using the object marker 1342 to create a model of objects 1301 in a fixed reference frame, the positions of the fiducials 1344 relative to each other are predetermined. In an exemplary embodiment, measurements may be taken to determine the length and orientation of the segments between fiducials 1344. In another embodiment, the object markers 1342 may be placed at predetermined orientations such that the positions of the fiducials 1344 relative to each other can be predetermined. As such, the segments between the fiducials 1344 can be mathematically determined.

In the embodiment depicted in FIG. 13A, the images of the object markers 1342 are depicted in the corresponding roentgenograms 1302 and 1304. Upon receiving the two roentgenograms, the 3-D position of the x-ray source 1312 with respect to the x-ray imager may be determined for each imaging orientation (1320, 1330) in accordance with the principles disclosed in the present disclosure. In particular, these determinations may be based on the use of reference markers and fiducials in the same way as is described with respect to the previous embodiments. Similarly, outlines of the imaged objects 1301 and shadow points 1306 of fiducials 1344 in the first and second roentgenograms (1302, 1304) may be identified using the same techniques described in the previous embodiment. At this point, different steps may be utilized to prepare a 3-D model of the imaged objects 1301 using the object markers 1342 and the fiducials 1344.

Figure 13B:
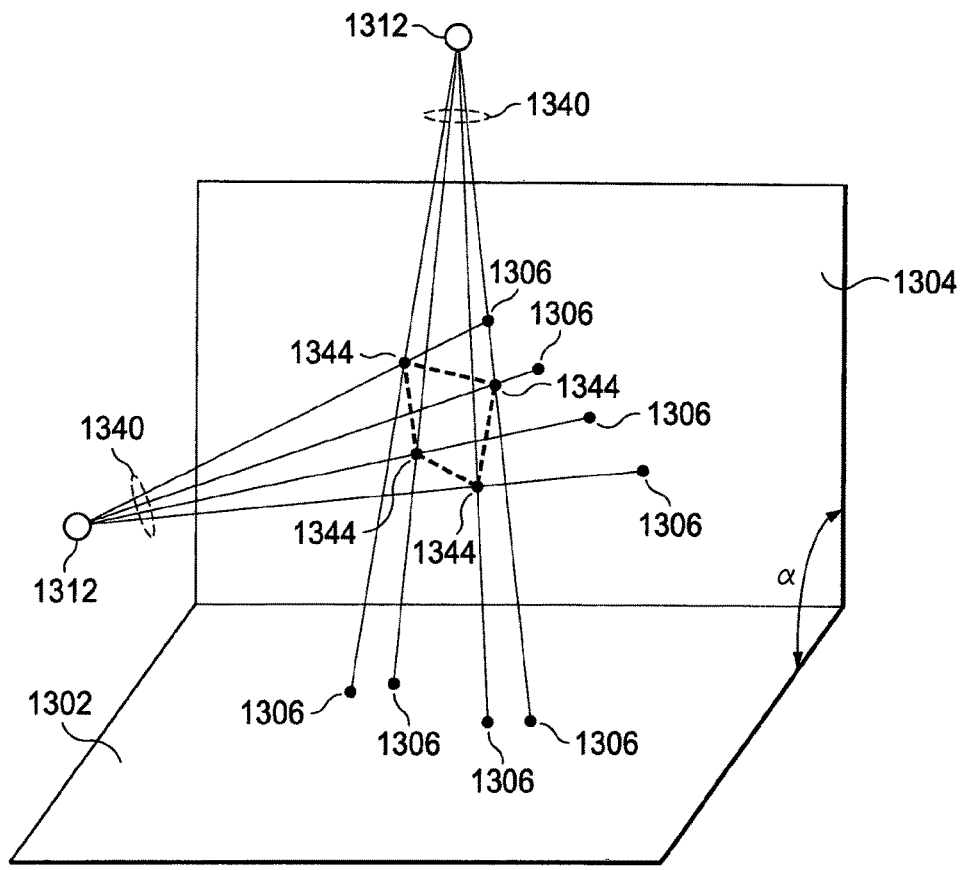
FIG. 13B is a schematic diagram illustrating projections of a plurality of fiducials from first and second roentgenograms to different light source locations, in accordance with the present disclosure.

Generally, the first approach of using the object marker 1342 to create a model of objects 1301 in a fixed reference frame includes constructing projection lines 1340 connecting the shadow points 1306 in roentgenograms (1302, 1304) and the location of the x-ray source 1312 in their respective imaging orientations (1320, 1330), as depicted in FIG. 13B. The 3-D positions of the fiducials 1344 relative to each roentgenogram (1302, 1304) may be mathematically determined based on the orientations of the projection lines 410 and the predetermined segments between the fiducials 1344. In turn, the angular displacement α between the two imaging orientations 220, 230 may be determined by aligning the 3-D positions of the fiducials 1344 in a fixed reference frame. Once the displacement angle α has been identified, the process of creating a 3-D model of the imaged object may proceed in the same manner as was described with respect to FIGS. 12C-12G.

Figure 13C:
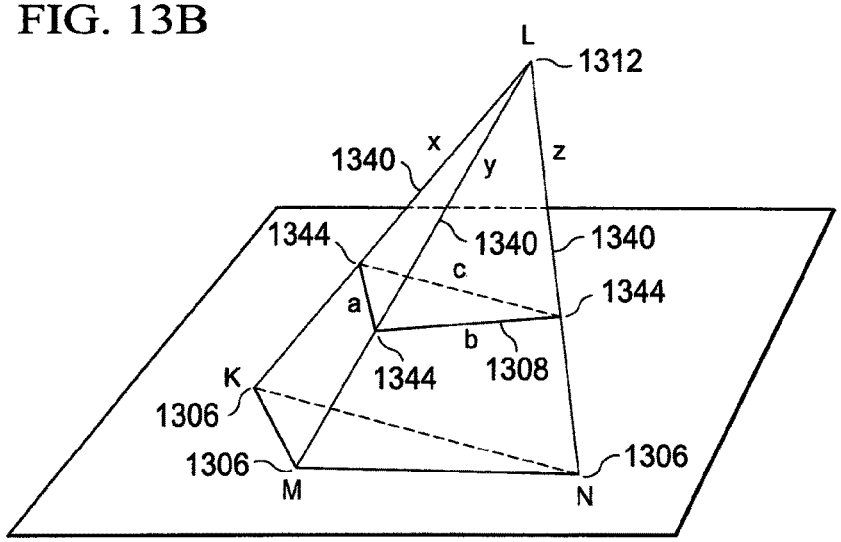
FIG. 13C is a schematic diagram illustrating a 3D model of projections of the markers in accordance with the present disclosure.

It is to be appreciated that the determination of the 3-D positions of the fiducials 1344 relative to each roentgenogram (1302, 1304) may be accomplished according to a variety of mathematical approaches. An exemplary mathematical approach is explored with reference to FIG. 13C. As discussed above, marker(s) (not shown) may be fixed to an object (not shown) in such a manner that positions of three fiducials 1344 relative to each other may be predetermined. In the embodiment illustrated in FIG. 13C, shadow points 1306 of the fiducials 1344 in the roentgenogram 304 may be used to construct projection lines 1340, which geometrically, may cooperate to form a three-sided pyramid. Additionally, since the positions of the corresponding fiducials 1344 relative to each other have been predetermined, the dimensions of a triangle 1308 formed by connecting the 3-D positions of the fiducials 1344 may also be mathematically determined. As such, the following geometric elements may be established as shown in FIG. 13C: coordinates (L) of light source 1312, coordinates (K, M, N) of shadow points 406, and the lengths of the legs (a, b, c) of triangle 1308. To determine the 3-D position and orientation of the triangle 1308, the exemplary approach of FIG. 13C may include rotating and "moving" the triangle 1308 within the pyramid until it reaches a position where dimensions of the triangle 1308 and the outer contour of the pyramid match. Based on known triangulation and trigonometric techniques, the position of the triangle 1308 may correspond to the solution to the following equation system:

$$\begin{cases} a^2 = x^2 + y^2 - 2xy\cos\alpha \\ b^2 = y^2 + z^2 - 2yz\cos\beta \\ c^2 = z^2 + x^2 - 2zx\cos\gamma \end{cases}$$

in which, angles KLM, MLN, KLN correspond to α, β, and γ, respectively, and x, y, z correspond to the distance between the light source 1312 and the fiducials 1344. Mathematically, this system of equations has eight different solutions, but some of them may include complex and negative numbers, and thus may be eliminated. As such, there may be two solutions remaining that may correctly reflect the position of the fiducials 1344. It is, however, difficult to mathematically determine which one out of remaining two solutions is correct. In an embodiment, 3-D models of the image object based on both solutions may be presented to a person, who may then visually determine and select the model that matches the orientation of the imaged object. In orthopedic application, the person selecting the matching model may be a physician.

Figure 13D:
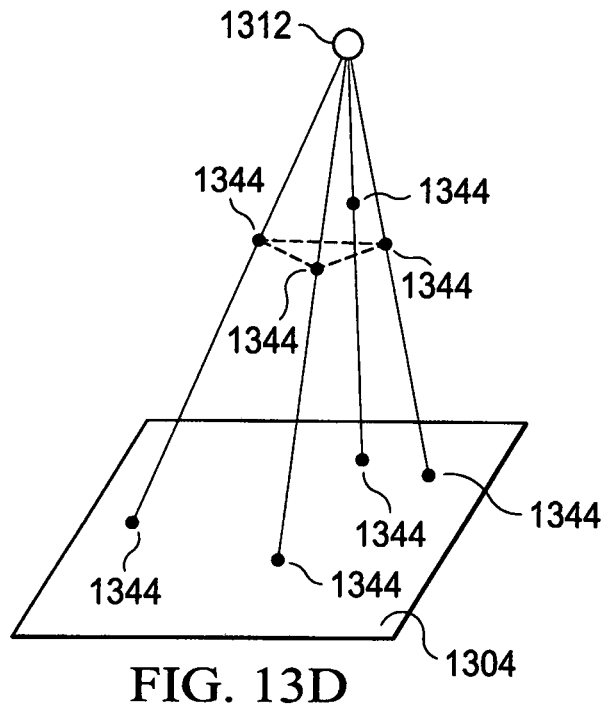
FIG. 13D is another schematic diagram illustrating a 3D model of projections of the markers shown in FIG. 13C, in accordance with the present disclosure.
Figure 13E:
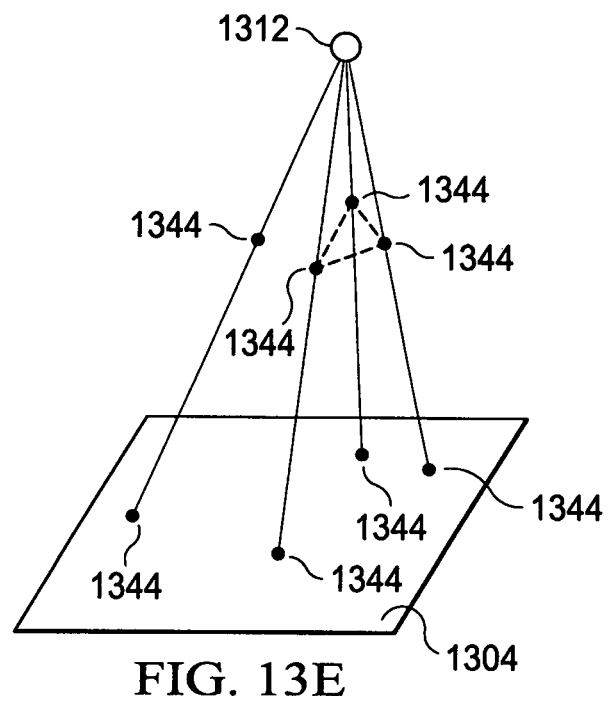
FIG. 13E is a schematic diagram illustrating another model of the markers in 3 D space, in accordance with the present disclosure.

To better expedite the modeling process, the involvement of a person to select a correct model as discussed above may be reduced or eliminated according the approaches disclosed with respect to FIGS. 13D and 13E. Generally, the above discussed mathematical model may be modified to include the consideration of additional fiducials. According to the illustrated approach, an extra fiducial 1344 is used such that there are four fiducials 1344 used instead of three, and as a result, four different three-sided pyramids may be constructed based on four different sets of triplet shadow points 1306. For each three-sided pyramid, several solutions may be available. In one embodiment, the different solutions may be compared to each other, and a final solution may be chosen according to a mathematical measure known in the art. For example, the solution that has the smallest deviation from other solutions may be chosen to determine the 3-D positions of the fiducials 1344 with respect to the roentgenogram 1304. In another example, an average of all the solutions may be chosen to determine the 3-D positions of the fiducials 1344.

The above discussed approaches may be repeated for determining 3-D positions of the fiducials 1344 with respect to the other roentgenogram 1302. By do so, the 3-D positions of the fiducials 1344 may be determined with respect to two different coordinate systems according to the above approach. Moreover, by aligning the fiducials in the two coordinate systems, the translation and rotational orientation (x, y, z, α, β, γ) of the first and second roentgenograms may be determined in a single, fixed reference frame as illustrated in FIG. 13B. In some embodiments, by determining the 3-D positions of the fiducials 1344 in a fixed reference frame, and given the predetermined relative orientation of the fiducials 1344 to the object in 3-D space, the 3-D position of the object may now be determined in the fixed reference frame.

It is to be appreciated that while the above exemplary approaches may be implemented using three or four fiducials 1344 to provide an efficient and precise method of accounting for the translation and rotational orientation (x, y, z, α, β, γ) of the first roentgenogram 1302 relative to the second roentgenogram 1304, other numbers of the fiducials 1344 may be used in other approaches in accordance with the principle of the present disclosure. To allow for greater accuracy and/or precision, five or more fiducials may be used. For example, eight fiducials may be used in an embodiment as shown in FIG. 13A. In such a case, there may be 56 combinations of fiducial triplets. With at least two possible solutions for each combination, there may be at least 112 different possible solutions for the positions of the fiducials 1344. A final solution may be chosen according to the following exemplary algorithm, which is based on a mathematical analysis of all the possible positions of the fiducials 1344:

1) Determine all the potential 3-D positions of each fiducial 1344 based on all the possible solutions obtained as discussed above.

2) Determine the mean 3-D positions of each fiducial 1344.

3) Determine the deviations of all potential 3-D positions of each fiducial 1344 from the respective mean 3-D position determined in step 2.

4) Identify a least likely 3-D position corresponding to the 3-D position that deviates the most from the respective mean 3-D position determined in step 2.

5) Eliminate the solution that resulted the least likely 3-D position.

6) Repeat steps 1 5 until the deviation of each remaining potential 3-D position of the fiducials 1344 has a deviation from the respective mean 3-D position is less than a criterion (e.g., 2 mm, 5 mm, 10 mm, etc.).

7) Approximate the 3-D position of each fiducial 1344 to be the mean of each remaining potential 3-D position of the fiducials 1344.

It is to be appreciated that the above algorithm allows an accurate approximation for the positions of the fiducials 1344, and it may be modified in accordance to the principles discussed herein and any mathematical technique known in the art. For example, in an exemplary embodiment, the algorithm may be modified to further include determining the variance between the possible positions of each fiducial 1344 and eliminate potential solutions based on deviations from both the mean and variance.

Practical Considerations

After the orthopedic device is imaged in the roentgenograms together with an object, the outline of the orthopedic device may be determined manually or using a suitable graphic software. For example, a physician may manually outline the orthopedic device and input such information into a computer. In another embodiment, the outline of the orthopedic device may be automatically generated by pattern recognition software. The outline of the orthopedic device may, in turn, be used to for determining a 3-D model of the object in accordance with the present disclosure.

Figure 7:
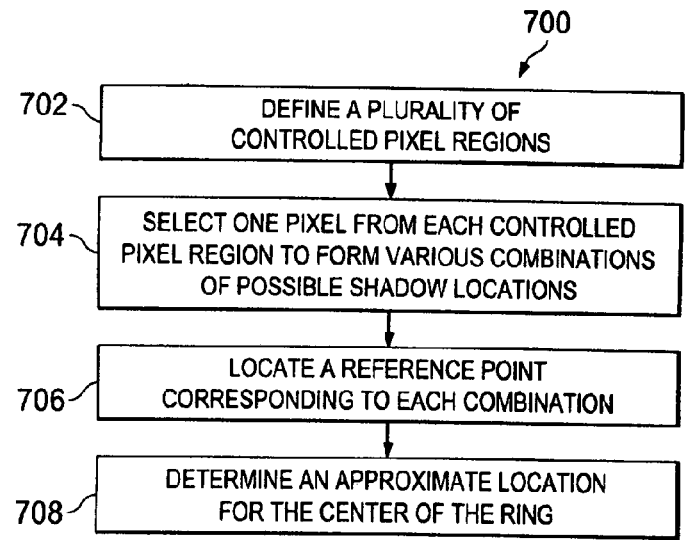
FIG. 7 is a flow diagram illustrating an exemplary algorithm, in accordance with the present disclosure.

It is to be appreciated that in some embodiments, a visible shadow may span across more than one pixel on a digital roentgenogram. Accordingly, the precise location of the visible shadow may be approximated using an approximation model. FIG. 7 is a flow chart illustrating the approach of one exemplary approximation model 700. The approximation model 700 includes a step 702 for defining a plurality of controlled pixel regions each comprising a plurality of pixels. The plurality of pixels of each controlled pixel region may correspond to the locations at which each visible shadow is most likely to be located. For example, a defined controlled pixel region may include a 3×3 grid of nine pixels around a visible shadow. In another example, a defined controlled pixel region may include a 4×4 grid of 16 pixels around a visible shadow. The exemplary model 700 may include a step 704 for arbitrarily assigning multiple combinations of possible shadow locations based on different sets of pixels, each set of pixels comprising one pixel from each defined controlled pixel region. The exemplary model 700 may include a step 706 for determining a location for a desired reference point for each assigned combination of shadow locations. For example, the desired reference point may be a center of a ring. In an embodiment, all combinations of shadow locations are assigned and used to determine a location for the desired reference point. In another embodiment, only selected combinations of shadow locations are assigned and used to determine a location for the desired reference point. The exemplary model 700 may further include a step 708 for processing the first and second locations of the desired reference point using an objective criterion to determine an approximated location for the center of the ring. In an exemplary embodiment, the objective criterion of step 708 may include one or more mathematics measurement known in the art, such mean, median, variance, standard deviation, or any combination thereof. In an exemplary embodiment, locations with differences of more than 0.01 mm may all be filtered out. In cases when none of the combinations of chosen regions provides that precision, the combination with the least difference in ring center positioning may be used.

Figure 8:
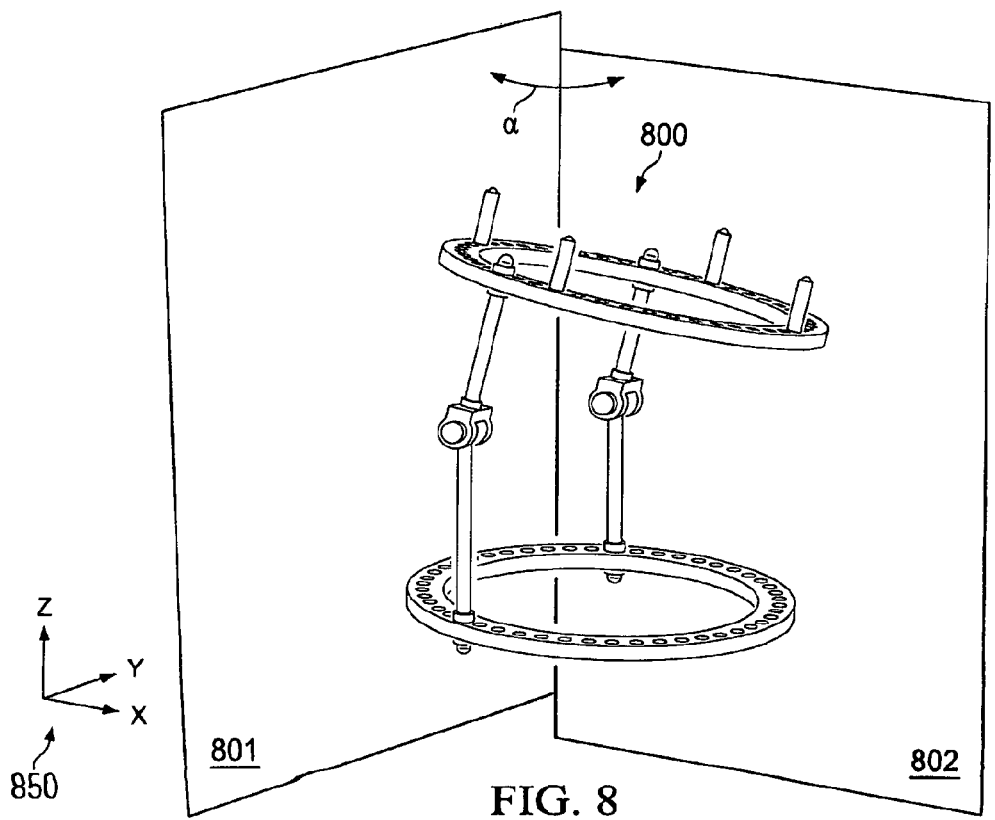
FIG. 8 is a schematic diagram illustrating an imaged object in a 3-D framework, in accordance with the present disclosure.

FIG. 8 is a schematic diagram showing a model of a fixture in a combined 3-D coordinate system 850. As discussed above with respect to FIGS. 2A-B, first and second 3-D coordinate systems are individually created based on two roentgenograms and comprise first and second planes 801 and 802, respectively. The first and second 3-D coordinate systems are combined to create the combined 3-D coordinate system 850. The first and second planes 801 and 802 are aligned at an angle such that the coordinates of the first and second reference points in the first and second 3-D coordinate systems coincide.

Figure 9:
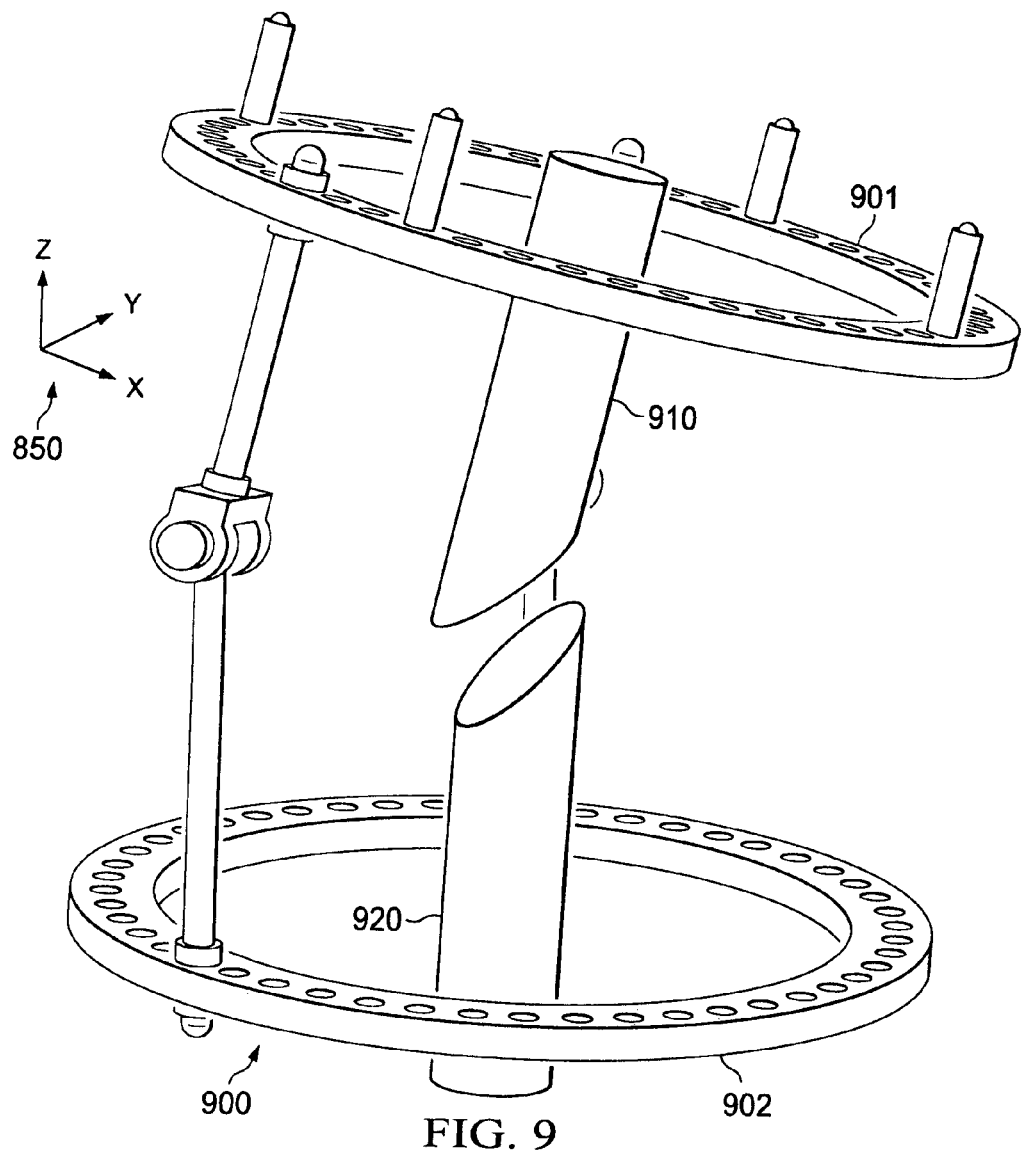
FIG. 9 is a schematic diagram illustrating an exemplary 3-D model of an object.

FIG. 9 is a model of a first object segment 910 coupled to the first ring 901 of a fixture 900 and a second object segment 920 coupled to the second ring 902 of the fixture 900. The model is based on the combined 3-D coordinate system 850 generated using the method discussed above. In some embodiments, the model of FIG. 8 allows for the determination of the orientation of the first bone segment 910 relative to the orientation of the second segment 920. In particular, the model allows for mathematically determining the relative orientation of the first and second bone segments 910 and 920 based on various orientations of the first ring 901 relative to the second ring 902.

This disclosure has described using two imaging orientations that are substantially orthogonal with respect to each other or non-orthogonal orientations. The choice between these two embodiments may depend upon a variety of factors, including equipment limitations and interest or lack of interest in the imaging certain orientations. Furthermore, more than two imaging orientations may be utilized consistent with the scope of the present disclosure. By using more than two imaging orientations, the accuracy of the 3-D model of the frame and the tissue can be improved.

Once a 3-D model of the frame and the tissue segments has been created, a physician or surgeon can more readily understand the nature of the fracture and the degree of fixation, compression, or distraction (or other force) that should be applied to the tissue segments in order to achieve the desired result. It is contemplated that the 3-D model of a hexapod ring fixator can be coupled with an automated frame controller such that the desired fixation, compression, or distraction commands can be automatically implemented.

Figure 10:
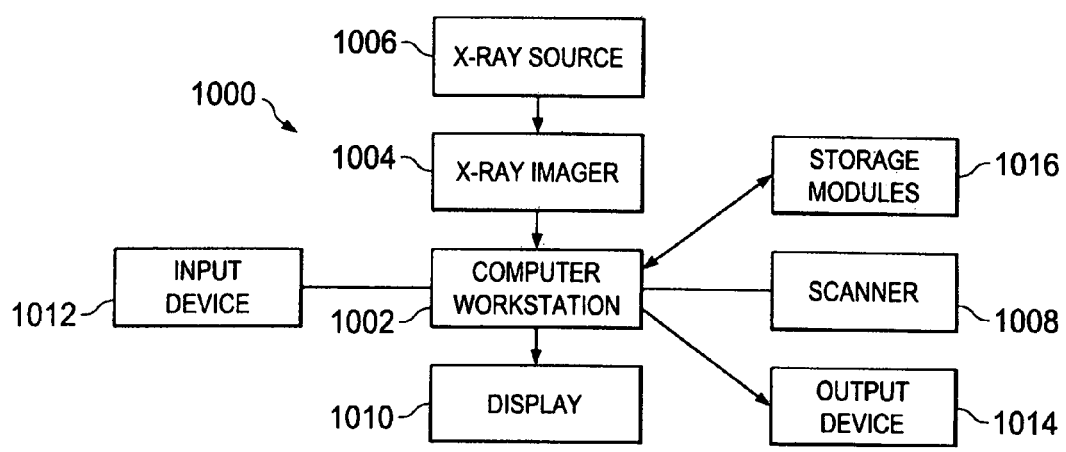
FIG. 10 is a schematic block diagram illustrating an exemplary system for creating 3-D model of an object.

As discussed above, a 3-D model of an object may be generated from roentgenograms of the object. FIG. 10 is a schematic diagram of a system 1000 operable to digitally generate a 3-D model of an imaged object (not shown) in accordance with the principles of the present disclosure. The system 1000 may include a computer workstation 1002 operable to receive roentgenograms of the imaged object, and the computer workstation 1002 may include one or more microprocessors/controllers in communication with a variety of auxiliary devices. In an embodiment, the system 1000 may include an x-ray imager 1004 in communication with the computer workstation 1002, and the x-ray imager 1004 is operable to receive x-ray light from an x-ray source 1006 passing through the imaged object. The x-ray imager 1004 may be operable to generate a roentgenogram directly, or it may be operable to transmit image data to the computer workstation 1002, which may then generate the x-ray image. In another embodiment, the system 1000 may include a scanner 1008 in communication with the workstation 1002, and the scanner 1008 may be operable to scan an x-ray film into digitized roentgenogram. In some embodiments, the system 1000 may further include a display 1010 in communication with the workstation 1002, and the display 1010 may be a LCD display, a CRT display, or any other displaying device known in the art. The workstation 1002 may be configured to display the digitized roentgenogram to a user on the display 1010, and the user may input a variety of data pertaining to the displayed roentgenogram as in the present disclosure, such as the location of markers or struts, the predetermined position of the markers or struts relative to each other. In an exemplary embodiment, the system 1000 includes one or more input device 1012, such as a mouse, light pen and/or keyboard, in communication with the workstation 1002, and the user may input the data using the input device 1012. Based on the user-input data and image data, the microprocessor or controller of the workstation 1002 may generate a 3-D model of the imaged object in accordance with the present disclosure. In some embodiments, the system 1000 may further include an output device 1014, such as a printer, operable to provide various model data, calculation results, images, or graphics to the user. The system 1000 may further include a storage module 1016 for storing various model data, calculation results, images, or graphics for later use.

Figure 11:
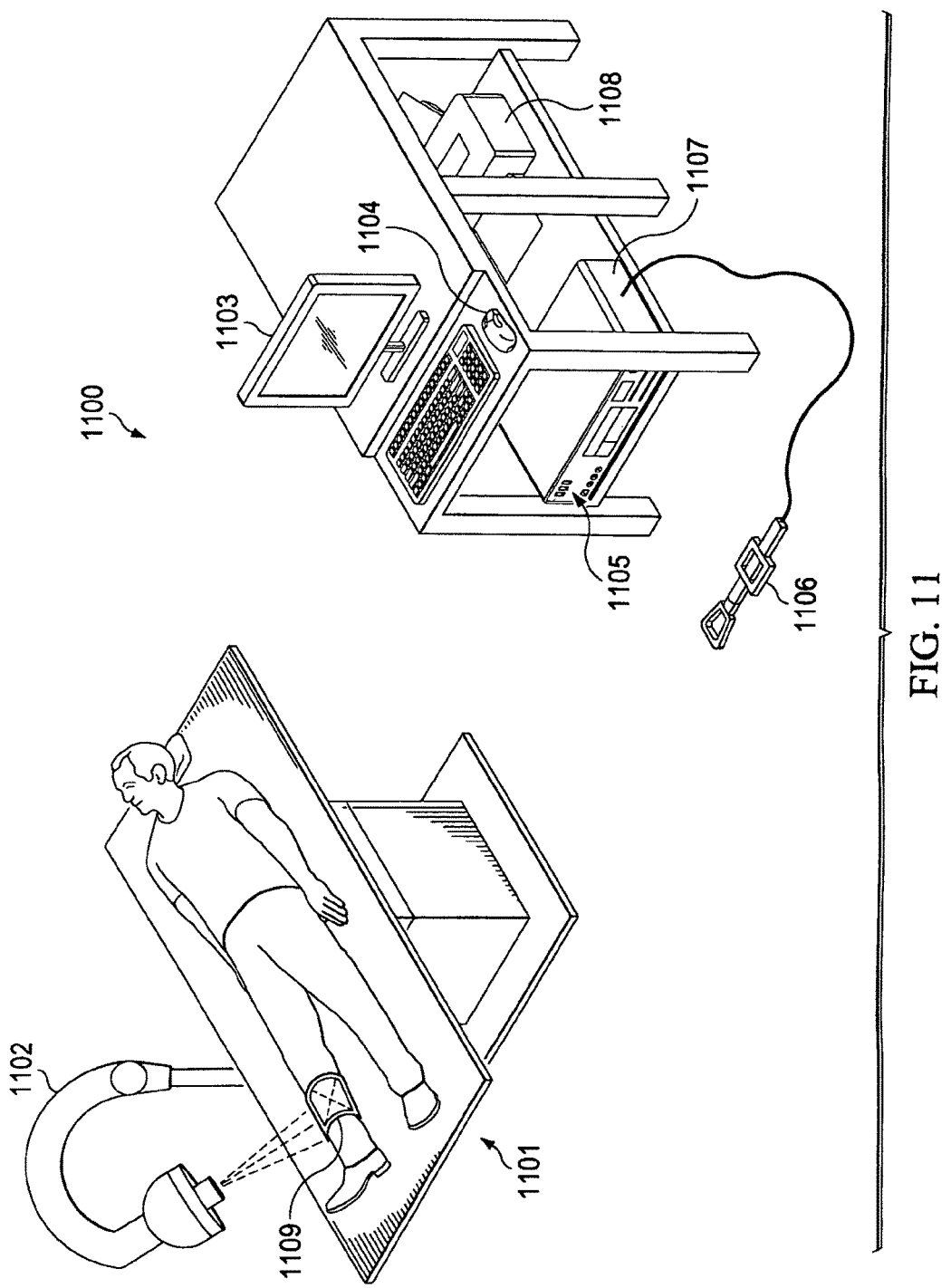
FIG. 11 is a schematic diagram illustrating an exemplary setup for determining 3-D model of an object and adjusting an external fixator accordingly.

FIG. 11 is a schematic diagram of an application of the system illustrated in FIG. 10. The present embodiment digitally generates a 3-D model of an imaged object in accordance with the principles of the present disclosure. A patient may be sitting or laying on a table 1101. In other embodiments, the patient may be sitting on a chair instead of the table 1101. The surface of the table 1101 may be of same material as an imager. Alternatively, an imager may be placed on the surface of the table 1101 and below the patient. An area to be examined with an x-ray and roentgenograms, a leg in the present embodiment, is surrounded with an orthopedic fixator 1109. The leg surrounded with the orthopedic fixator 1109 is x-rayed with an x-ray device 1102 according to the principles of the present disclosure. The leg surrounded with the orthopedic fixator 1109 may be x-rayed from different orientations with the x-ray device 1102, which can rotate in x, y, and z directions.

The x-rayed data is transmitted to a user's local machine 1107 via cables (not shown) or wirelessly via the internet or any other suitable network. The user's local machine 1107 is a regular desktop computer in the present embodiment, but may be any computing device as illustrated as the computer workstation 1002 of FIG. 10. The user's local machine 1107 may be equipped with a processor and a memory for receiving, processing, and storing the x-ray data. The user's local machine 1107 may be connected to a display 1103 that displays the x-ray data as images. The user's local machine 1107 may be connected to a mouse 1104, a keyboard (not shown), and a scanner/printer 1108. The scanner/printer 1108 is operable to scan x-ray images or print transmitted x-ray data. X-ray data may also be fed into the user's local machine 1107 with a CD, a universal serial bus (USB) drive 1105, or any other memory device such as floppy disks.

The 3-D position of the patient's leg and fixator will be determined according to the disclosed methods. The user may then process the transmitted x-ray data and determine the necessary adjustments that must be made to the orthopedic fixator 1109. Based on these determinations, the user may use a programmable wrench 1106 that is connected to the user's local machine 1107 to automatically adjust the orthopedic fixator 1109 by tightening or loosening its connection points. Alternatively, the user, most likely a physician or a medical staff member, may manually adjust the orthopedic fixator 1109 based on the transmitted x-ray data.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

While the methods and systems of this invention have been described in terms of preferred embodiments, it will be apparent to those of skill in the art that variations may be applied to the methods and systems and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A method of creating a 3-D model of a body part, the body part being coupled to an object, the object comprising a plurality of markers at predetermined distances along the object, the method comprising:

receiving a first roentgenogram of the body part and the object disposed between an x-ray source and an x-ray imager in a first orientation, wherein the first roentgenogram includes an image of:
the body part,
the object, and
the plurality of markers;

receiving a second roentgenogram of the body part and the object disposed between the x-ray source and the x-ray imager in a second orientation, wherein the second roentgenogram includes an image of:
the body part,
the object, and
the plurality of markers;

determining a first set of projections of the plurality of markers on the first roentgenogram;

determining a first 3-D position of the x-ray source and a first 3-D position of the object with respect to the x-ray imager in the first orientation by satisfying following mathematical equations:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z2-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein (x,y,z) are coordinates of the x-ray source, (x0, y0,z0) through (x3,y3,z3) are coordinates of the plurality of markers, (X0,Y0,Z0) through (X3,Y3,Z3) are coordinates of the first set of projections of the plurality of markers on the first roentgenogram, and l01, l02, l03, l04, l12, l13, l14, l23, l24, l34 are the predetermined distances between the plurality of markers to determine the distances between the plurality of markers, distances between the first set of the projections of the plurality of markers on the first roentgenogram and the plurality of markers, and distances between the plurality of markers and the x-ray source;

determining a second set of projections of the plurality of markers on the second roentgenogram;

determining a second 3-D position of the x-ray source and a second 3-D position of the object with respect to the x-ray imager in the second orientation by satisfying following mathematical equations:

$$\begin{cases} ('x-x0)*('Y0-y0)-('y-y0)*('X0-x0)=0 \\ ('x-x0)*('Z0-z0)-('z-z0)*('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-y2)-('y-y2)*('X2-x2)=0 \\ ('x-x2)*('Z2-z2)-('z-z2)*('X2-x2)=0 \\ ('x-x3)*('Y3-y3)-('y-y3)*('X3-x3)=0 \\ ('x-x3)*('Z3-z3)-('z-z3)*('X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein ('x,'y,'z) are coordinates of the x-ray source, (x0, y0,z0) through (x3,y3,z3) are coordinates of the plurality of markers, ('X0,'Y0,'Z0) through ('X3,'Y3,'Z3) are coordinates of the second set of projections of the plurality of markers on the second roentgenogram, and l01, l02, l03, l04, l12, l13, l14, l23, l24, l34 are the predetermined distances between the plurality of markers to determine the distances between the plurality of markers, and distances between the second set of projections of the plurality of markers on the second roentgenogram and the x-ray source, and distances between the second set of projections of the plurality of markers on the second roentgenogram and the plurality of markers;

aligning the first and second 3-D object projections in a 3-D reference frame using the 3-D positions of the plurality of markers with respect to the x-ray imager in the first and second orientations; and creating a 3-D model of the imaged body part in the 3-D reference frame based on the first and second 3-D object projections.

2. The method of claim 1, wherein the plurality of markers comprises a plurality of joints where a plurality of struts are connected to at least one fixation member.

3. The method of claim 1, wherein the object is an orthopedic fixator.

4. The method of claim 1, wherein the plurality of markers comprises four markers, and further wherein the first 3-D positions of the x-ray source and of the object are determined by satisfying following mathematical equations:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z2-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein (x,y,z) are coordinates of the x-ray source, (x0,y0,z0) through (x3,y3,z3) are coordinates of the four markers, (X0,Y0,Z0) through (X3,Y3,Z3) are coordinates of the first set of the projections of the four markers on the first roentgenogram, and l01, l02, l03, l04, l12, l13, l14, l23, l24, l34 are the predetermined distances between the four markers; and further wherein the second 3-D positions of the x-ray source and of the object are determined by satisfying following mathematical equations:

$$\begin{cases} ('x-x0)*('Y0-y0)-('y-y0)*('X0-x0)=0 \\ ('x-x0)*('Z0-z0)-('z-z0)*('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-y2)-('y-y2)*('X2-x2)=0 \\ ('x-x2)*('Z2-z2)-('z-z2)*('X2-x2)=0 \\ ('x-x3)*('Y3-y3)-('y-y3)*('X3-x3)=0 \\ ('x-x3)*('Z3-z3)-('z-z3)*('X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein ('x,'y,'z) are the coordinates of the x-ray source, (x0,y0,z0) through (x3,y3,z3) are the coordinates of the four markers, ('X0,'Y0,'Z0) through ('X3,'Y3,'Z3) are coordinates of the second set of the projections of the four markers on the second roentgenogram, and l01, l02, l03, l04, l12, l13, l14, l23, l24, l34 are the predetermined distances between the four markers.

5. The method of claim 1, wherein the plurality of markers comprises four markers, and further wherein the first 3-D positions of the x-ray source and of the object are determined by satisfying following mathematical equations:

$$\begin{cases} (x0-x1)^2-(y0-y1)^2-(z-z1)^2-l01^2=0 \\ (x0-x2)^2-(y0-z2)^2-(z-z2)^2-l02^2=0 \\ (x0-x3)^2-(y0-y3)^2-(z-z3)^2-l03^2=0 \\ (x1-x2)^2-(y1-z2)^2-(z1-z2)^2-l12^2=0 \\ (x1-x3)^2-(y1-y3)^2-(y1-y3)^2-l13^2=0 \\ (x2-x3)^2-(y2-z3)^2-(z2-z3)^2-l23^2=0 \end{cases}$$

wherein (x0,y0,z0) through (x3,y3,z3) are coordinates of the four markers and l01, l02, l03, l12, l13, l23 are the predetermined distances between the four markers; and further wherein the second 3-D positions of the x-ray source and of the object are determined satisfying following mathematical equations:

$$\begin{cases} (x0-x1)^2-(y0-y1)^2-(z0-z1)^2-l01^2=0 \\ (x0-x2)^2-(y0-z2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z2)^2-l13^2=0 \\ (x2-x3)^2-(y2-z3)^2-(z2-z3)^2-l23^2=0 \end{cases}$$

wherein (x0,y0,z0) through (x3,y3,z3) are the coordinates of the four markers and l01, l02, l03, l12, l13, l23 are the predetermined distances between the four markers.

6. The method of claim 1, wherein the plurality of markers comprises four markers, and further wherein the first 3-D positions of the x-ray source and of the object are determined by satisfying following mathematical equations:

$$\begin{cases} \begin{vmatrix} x0-x & y0-y & z0-z \\ X0-x & Y0-x & Z0-z \\ X1-x & Y1-y & Z1-z \end{vmatrix} = 0 \\ \begin{vmatrix} x1-x & y1-y & z1-z \\ X0-x & Y0-x & Z0-z \\ X1-x & Y1-y & Z1-z \end{vmatrix} = 0 \\ \begin{vmatrix} x1-x & y1-y & z1-z \\ X1-x & Y1-x & Z1-z \\ X2-x & Y2-y & Z2-z \end{vmatrix} = 0 \\ \begin{vmatrix} x2-x & y2-y & z2-z \\ X1-x & Y1-x & Z1-z \\ X2-x & Y2-y & Z2-z \end{vmatrix} = 0 \\ \begin{vmatrix} x2-x & y2-y & z2-z \\ X2-x & Y2-x & Z2-z \\ X3-x & Y3-y & Z3-z \end{vmatrix} = 0 \\ \begin{vmatrix} x3-x & y3-y & z3-z \\ X2-x & Y2-x & Z2-z \\ X3-x & Y3-y & Z3-z \end{vmatrix} = 0 \\ \begin{vmatrix} x3-x & y3-y & z3-z \\ X3-x & Y3-x & Z3-z \\ X0-x & Y0-y & Z0-z \end{vmatrix} = 0 \\ \begin{vmatrix} x0-x & y0-y & z0-z \\ X3-x & Y3-x & Z3-z \\ X0-x & Y0-y & Z0-z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z2)^2 - l13^2 = 0 \\ (x2-x3)^2 - (y2-y3)^2 - (z2-z3)^2 - l23^2 = 0 \end{cases}$$

wherein (x,y,z) are coordinates of the x-ray source, (x0,y0,z0) through (x3,y3,z3) are coordinates of the four markers, (X0,Y0,Z0) through (X3,Y3,Z3) are coordinates of the first set of the projections of the four markers on the first roentgenogram, and l01, l02, l03, l12, l13, l23 are the predetermined distances between the four markers; and further wherein the second 3-D positions of the x-ray source and of the object are determined by satisfying following mathematical equations:

$$\begin{cases} \begin{vmatrix} x0-'x & y0-'y & z0-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X1-'x & 'Y1-'x & 'Z1-'z \\ 'X2-'x & 'Y2-'y & 'Z2-'z \end{vmatrix} = 0 \\ \begin{vmatrix} x2-'x & y2-'y & z2-'z \\ 'X1-'x & 'Y1-'x & 'Z1-'z \\ 'X2-'x & 'Y2-'y & 'Z2-'z \end{vmatrix} = 0 \\ \begin{vmatrix} x2-'x & y2-'y & z2-'z \\ 'X2-'x & 'Y2-'x & 'Z2-'z \\ 'X3-'x & 'Y3-'y & 'Z3-'z \end{vmatrix} = 0 \\ \begin{vmatrix} x3-'x & y3-'y & z3-'z \\ 'X2-'x & 'Y2-'x & 'Z2-'z \\ 'X3-'x & 'Y3-'y & 'Z3-'z \end{vmatrix} = 0 \\ \begin{vmatrix} x3-'x & y3-'y & z3-'z \\ 'X3-'x & 'Y3-'x & 'Z3-'z \\ 'X0-'x & 'Y0-'y & 'Z0-'z \end{vmatrix} = 0 \\ \begin{vmatrix} x0-'x & y0-'y & z0-'z \\ 'X3-'x & 'Y3-'x & 'Z3-'z \\ 'X0-'x & 'Y0-'y & 'Z0-'z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x2-x3)^2 - (y2-y3)^2 - (z2-z3)^2 - l23^2 = 0 \end{cases}$$

wherein, ('x,'y,'z) are the coordinates of the x-ray source, (x0,y0,z0) through (x3,y3,z3) are the coordinates of the four markers, ('X0,'Y0,'Z0) through ('X3,'Y3,'Z3) are coordinates of the second set of the projections of the four markers on the second roentgenogram, and l01, l02, l03, l12, l13, l23 are the predetermined distances between the four markers.

7. The method of claim 1, further comprising:
identifying a first body part outline of the imaged body part in the first roentgenogram;
identifying a second body part outline of the imaged body part in the second roentgenogram;
preparing a first 3-D body part projection from the first body part outline to the first 3-D position of the x-ray source;
preparing a second 3-D body part projection from the second body part outline to the second 3-D position of the x-ray source;
creating a 3-D model of the imaged body part in the 3-D reference frame based on the first and second body part projections.

8. The method of claim 7, further comprising:
identifying a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation;

identifying one or more intersection planes passing through the tilt axis and through the first and second 3-D projections of the imaged body part in the 3-D reference frame;

for each of the one or more intersection planes, performing the following steps, a) through c):

a) identifying one or more intersection points between the first and second 3-D body part projections, and said intersection plane in the 3-D reference frame;

b) preparing one or more polygons connecting the intersection points in said intersection plane;

c) preparing one or more closed curves within the each of the one or more polygons, wherein the one or more closed curves corresponds to a cross-sectional view of the imaged body part in said intersection plane; and preparing a surface in the 3-D reference frame that connects each of the closed curves to form a 3-D model of the imaged body part.

9. A method of creating a 3-D model of a body part, the body part being coupled to an object, the object comprising a plurality of struts with predetermined lengths that are each connected to at least two fixation members with predetermined dimensions, the method comprising:

receiving a first roentgenogram of the body part and the object disposed between an x-ray source and an x-ray imager in a first orientation, wherein the first roentgenogram includes an image of:

the body part, the object, and the plurality of struts with predetermined lengths that are each connected to the at least two fixation members at two connection points, wherein the distances between the two connection points are predetermined;

receiving a second roentgenogram of the body part and the object disposed between the x-ray source and the x-ray imager in a second orientation, wherein the second roentgenogram includes an image of:

the body part, the object, and the plurality of struts with predetermined lengths that are each connected to the at least two fixation members at two connection points, wherein the distances between the two connection points are predetermined;

determining a first set of projections of longitudinal axes of the plurality of struts on the first roentgenogram;

determining a first 3-D position of the x-ray source and a first 3-D position of the object with respect to the x-ray imager by satisfying following mathematical equations:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z1-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x-x4)*(Y4-y4)-(y-y4)*(X4-x4)=0 \\ (x-x4)*(Z4-z4)-(z-z4)*(X4-x4)=0 \\ (x-x5)*(Y5-y5)-(y-y5)*(X5-x5)=0 \\ (x-x5)*(Z5-z5)-(z-z5)*(X5-x5)=0 \\ (x-x6)*(Y6-y6)-(y-y6)*(X6-x6)=0 \\ (x-x6)*(Z6-z6)-(z-z6)*(X6-x6)=0 \\ (x-x7)*(Y7-y7)-(y-y7)*(X7-x7)=0 \\ (x-x7)*(Z7-z7)-(z-z7)*(X7-x7)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \end{cases}$$

$$\begin{cases} (x0-x4)^2-(y0-y4)^2-(z0-z4)^2-l04^2=0 \\ (x0-x5)^2-(y0-y5)^2-(z0-z5)^2-l05^2=0 \\ (x0-x6)^2-(y0-y6)^2-(z0-z6)^2-l06^2=0 \\ (x0-x7)^2-(y0-y7)^2-(z0-z7)^2-l07^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x1-x5)^2-(y1-y5)^2-(z1-z5)^2-l15^2=0 \\ (x1-x6)^2-(y1-y6)^2-(z1-z6)^2-l16^2=0 \\ (x1-x7)^2-(y1-y7)^2-(z1-z7)^2-l17^2=0 \\ (x2-x3)^2-(y2-y3)^2-(z2-z3)^2-l23^2=0 \\ (x2-x4)^2-(y2-y4)^2-(z2-z4)^2-l24^2=0 \\ (x2-x5)^2-(y2-y5)^2-(z2-z5)^2-l25^2=0 \\ (x2-x6)^2-(y2-y6)^2-(z2-z6)^2-l26^2=0 \\ (x2-x7)^2-(y2-y7)^2-(z2-z7)^2-l27^2=0 \end{cases}$$

wherein (x,y,z) are coordinates of the x-ray source, (x0, y0,z0) through (x7,y7,z7) are coordinates of the eight strut connection points to the fixation members, (X0, Y0,Z0) to (X1,Y1,Z1), . . . (X6,Y6,Z6) to (X7,Y7,Z7) are coordinates of a first set of projections of longitudinal axes of the struts on the first roentgenogram, (X'0,Y'0,Z'0) through (X'7,Y'7,Z'7) are coordinates of a first set of projections of the eight strut connection points on the first roentgenogram, and l01, l02, l03, l04, l06, l07, l12, l13, l14, l15, l16, l17, l23, l24, l25, l26, l27 are the predetermined distances between the strut connection points of the four struts, si are unknown ratios, and v(i−1)ix, v(i−1)iy, v(i−1)iz are vectors of projections of the longitudinal axes of the struts, wherein v(i−1)ix=Xi−X(i−1), v(i−1)iy=Yi−Y(i−1), v0iz=Zi−Z(i−1);

determining a second set of projections of longitudinal axes of the plurality of struts on the second roentgenogram;

determining a second 3-D position of the x-ray source and a second 3-D position of the object with respect to the x-ray imager by satisfying following mathematical equations:

$$\begin{cases} ('x-x0)*(Y'0-y0)-('y-y0)*(X'0-x0)=0 \\ ('x-x0)*(Z'0-z0)-('z-z0)*(X'0-x0)=0 \\ ('x-x1)*(Y'1-y1)-('y-y1)*(X'1-x1)=0 \\ ('x-x1)*(Z'1-z1)-('z-z1)*(X'1-x1)=0 \\ ('x-x2)*(Y'2-y2)-('y-y2)*(X'2-x2)=0 \\ ('x-x2)*(Z'1-z2)-('z-z2)*(X'2-x2)=0 \\ ('x-x3)*(Y'3-y3)-('y-y3)*(X'3-x3)=0 \\ ('x-x3)*(Z'3-z3)-('z-z3)*(X'3-x3)=0 \\ ('x-x4)*(Y'4-y4)-('y-y4)*(X'4-x4)=0 \\ ('x-x4)*(Z'4-z4)-('z-z4)*(X'4-x4)=0 \\ ('x-x5)*(Y'5-y5)-('y-y5)*(X'5-x5)=0 \\ ('x-x5)*(Z'5-z5)-('z-z5)*(X'5-x5)=0 \\ ('x-x6)*(Y'6-y6)-('y-y6)*(X'6-x6)=0 \\ ('x-x6)*(Z'6-z6)-('z-z6)*(X'6-x6)=0 \\ ('x-x7)*(Y'7-y7)-('y-y7)*(X'7-x7)=0 \\ ('x-x7)*(Z'7-z7)-('z-z7)*(X'7-x7)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \end{cases}$$

-continued
$$\begin{cases} (x0-x4)^2-(y0-y4)^2-(z0-z4)^2-l04^2=0 \\ (x0-x5)^2-(y0-y5)^2-(z0-z5)^2-l05^2=0 \\ (x0-x6)^2-(y0-y6)^2-(z0-z6)^2-l06^2=0 \\ (x0-x7)^2-(y0-y7)^2-(z0-z7)^2-l07^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x1-x5)^2-(y1-y5)^2-(z1-z5)^2-l15^2=0 \\ (x1-x6)^2-(y1-y6)^2-(z1-z6)^2-l16^2=0 \\ (x1-x7)^2-(y1-y7)^2-(z1-z7)^2-l17^2=0 \\ (x2-x3)^2-(y2-y3)^2-(z2-z3)^2-l23^2=0 \\ (x2-x4)^2-(y2-y4)^2-(z2-z4)^2-l24^2=0 \\ (x2-x5)^2-(y2-y5)^2-(z2-z5)^2-l25^2=0 \\ (x2-x6)^2-(y2-y6)^2-(z2-z6)^2-l26^2=0 \\ (x2-x7)^2-(y2-y7)^2-(z2-z7)^2-l27^2=0 \end{cases}$$

wherein ('x,'y,'z) are the coordinates of the x-ray source, (x0,y0,z0) through (x7,y7,z7) are the coordinates of the eight strut connection points to the fixation members, ('X0,'Y0,'Z0) to ('X1,'Y1,'Z1), . . . ('X6,'Y6,'Z6) to ('X7,'Y7,'Z7) are coordinates of a second set of projections of longitudinal axes of the struts on the second roentgenogram, ('X'0,'Y'0,'Z'0) through ('X'7,'Y'7,'Z'7) are coordinates of a second set of projections of the eight strut connection points on the second roentgenogram, and l01, l02, l03, l04, l06, l07, l12, l13, l14, l15, l16, l17, l23, l24, l25, l26, l27 are the predetermined distances between the strut connection points of the four struts, si are unknown ratios, and 'v(i−1)ix, 'v(i−1)iy, 'v(i−1)iz are vectors of projections of the longitudinal axes of the struts, wherein 'v(i−1)ix, 'Xi−'X(i−1), 'v(i−1)iy, 'Yi−'Y(i−1), 'v0iz, 'Zi−'Z(i−1);

aligning the first and second 3-D object projections in a 3-D reference frame using the 3-D positions of the plurality of struts with respect to the x-ray imager in the first and second orientations; and creating a 3-D model of the imaged body part in the 3-D reference frame based on the first and second 3-D object projections.

10. The method of claim 9, wherein the object is an orthopedic fixator.

11. The method of claim 9, wherein the plurality of struts comprises five struts, and further wherein the first 3-D positions of the x-ray source and of the object are determined by satisfying following mathematical equations:

$$\begin{cases}
(x-x0)*(Y0+v01y*s0-y0)-(y-y0)*(X0+v01x*s0-x0)=0\\
(x-x0)*(Z0+v01z*s0-z0)-(z-z0)*(X0+v01x*s0-x0)=0\\
(x-x1)*(Y1+v01y*s1-y1)-(y-y1)*(X1+v01x*s1-x1)=0\\
(x-x1)*(Z1+v01z*s1-z1)-(z-z1)*(X1+v01x*s1-x1)=0\\
(x-x2)*(Y2+v23y*s2-y2)-(y-y2)*(X2+v23x*s2-x2)=0\\
(x-x2)*(Z2+v23z*s2-z2)-(z-z2)*(X2+v23x*s2-x2)=0\\
(x-x3)*(Y3+v23y*s3-y3)-(y-y3)*(X3+v23x*s3-x3)=0\\
(x-x3)*(Z3+v23z*s3-z3)-(z-z3)*(X3+v23x*s3-x3)=0\\
(x-x4)*(Y4+v45y*s4-y4)-(y-y4)*(X4+v45x*s4-x4)=0\\
(x-x4)*(Z4+v45z*s4-z4)-(z-z4)*(X4+v45x*s4-x4)=0\\
(x-x5)*(Y5+v45y*s5-y5)-(y-y5)*(X5+v45x*s5-x5)=0\\
(x-x5)*(Z5+v45z*s5-z5)-(z-z5)*(X5+v45x*s5-x5)=0\\
(x-x6)*(Y6+v67y*s6-y6)-(y-y6)*(X6+v67x*s6-x6)=0\\
(x-x6)*(Z6+v67z*s6-z6)-(z-z6)*(X6+v67x*s6-x6)=0\\
(x-x7)*(Y7+v67y*s7-y7)-(y-y7)*(X7+v67x*s7-x7)=0\\
(x-x7)*(Z7+v67z*s7-z7)-(z-z7)*(X7+v67x*s7-x7)=0\\
(x-x8)*(Y8+v89y*s8-y8)-(y-y8)*(X8+v89x*s8-x8)=0\\
(x-x8)*(Z8+v89z*s8-z8)-(z-z8)*(X8+v89x*s8-x8)=0\\
(x-x9)*(Y9+v89y*s9-y9)-(y-y9)*(X9+v89x*s9-x9)=0\\
(x-x9)*(Z9+v89z*s9-z9)-(z-z9)*(X9+v89x*s9-x9)=0\\
(x0-x1)^2-(y0-y1)^2-(z0-z1)^2-l01^2=0\\
(x0-x2)^2-(y0-y2)^2-(z0-z2)^2-l02^2=0\\
(x0-x3)^2-(y0-y3)^2-(z0-z3)^2-l03^2=0\\
(x0-x4)^2-(y0-y4)^2-(z0-z4)^2-l04^2=0\\
(x0-x5)^2-(y0-y5)^2-(z0-z5)^2-l05^2=0\\
(x0-x6)^2-(y0-y6)^2-(z0-z6)^2-l06^2=0\\
(x0-x7)^2-(y0-y7)^2-(z0-z7)^2-l07^2=0\\
(x0-x8)^2-(y0-y8)^2-(z0-z8)^2-l08^2=0\\
(x0-x9)^2-(y0-y9)^2-(z0-z9)^2-l09^2=0\\
(x1-x2)^2-(y1-y2)^2-(z1-z2)^2-l12^2=0\\
(x1-x3)^2-(y1-y3)^2-(z1-z3)^2-l13^2=0\\
(x1-x4)^2-(y1-y4)^2-(z1-z4)^2-l14^2=0\\
(x1-x5)^2-(y1-y5)^2-(z1-z5)^2-l15^2=0\\
(x1-x6)^2-(y1-y6)^2-(z1-z6)^2-l16^2=0\\
(x1-x7)^2-(y1-y7)^2-(z1-z7)^2-l17^2=0\\
(x1-x8)^2-(y1-y8)^2-(z1-z8)^2-l18^2=0\\
(x1-x9)^2-(y1-y9)^2-(z1-z9)^2-l19^2=0\\
(x2-x3)^2-(y2-y3)^2-(z2-z3)^2-l23^2=0\\
(x2-x4)^2-(y2-y4)^2-(z2-z4)^2-l24^2=0\\
(x2-x5)^2-(y2-y5)^2-(z2-z5)^2-l25^2=0\\
(x2-x6)^2-(y2-y6)^2-(z2-z6)^2-l26^2=0\\
(x2-x7)^2-(y2-y7)^2-(z2-z7)^2-l27^2=0
\end{cases}$$

further satisfying one of following mathematical equations:

$$\begin{cases}(x2-x8)^2-(y2-y8)^2-(z2-z8)^2-l28^2=0\\(x2-x9)^2-(y2-y9)^2-(z2-z9)^2-l29^2=0\end{cases}$$

wherein (x,y,z) are coordinates of the x-ray source, (x0, y0,z0) through (x9,y9,z9) are coordinates of the ten strut connection points to the fixation members, (X0, Y0,Z0) to (X1,Y1,Z1), . . . (X8,Y8,Z8) to (X9,Y9,Z9) are coordinates of the first set of the projections of the longitudinal axes of the struts on the first roentgenogram, and l01, l02, l03, l04, l06, l07, l08, l09, l12, l13, l14, l15, l16, l17, l18, l19, l23, l24, l25, l26, l27, l28, l29 are the predetermined distances between the strut connection points of the five struts, si are unknown ratios, and v(i−1)ix, v(i−1)iy, v(i−1)iz are vectors of projections of longitudinal axes of the struts, wherein v(i−1)ix, Xi−X(i−1), v(i−1)iy, Yi−Y(i−1), v0iz=Zi−Z(i−1); and further wherein the second 3-D positions of the x-ray source and of the object are determined by satisfying following mathematical equations:

$$\begin{cases} ('x-x0)*('Y0 + 'v01y * 's0 - y0) - ('y-y0)*('X0 + 'v01x * 's0 - x0) = 0 \\ ('x-x0)*('Z0 + 'v01z * 's0 - z0) - ('z-z0)*('X0 + 'v01x * 's0 - x0) = 0 \\ ('x-x1)*('Y1 + 'v01y * 's1 - y1) - ('y-y1)*('X1 + 'v01x * 's1 - x1) = 0 \\ ('x-x1)*('Z1 + 'v01z * 's1 - z1) - ('z-z1)*('X1 + 'v01x * 's1 - x1) = 0 \\ ('x-x2)*('Y2 + 'v23y * 's2 - y2) - ('y-y2)*('X2 + 'v23x * 's2 - x2) = 0 \\ ('x-x2)*('Z2 + 'v23z * 's2 - z2) - ('z-z2)*('X2 + 'v23x * 's2 - x2) = 0 \\ ('x-x3)*('Y3 + 'v23y * 's3 - y3) - ('y-y3)*('X3 + 'v23x * 's3 - x3) = 0 \\ ('x-x3)*('Z3 + 'v23z * 's3 - z3) - ('z-z3)*('X3 + 'v23x * 's3 - x3) = 0 \\ ('x-x4)*('Y4 + 'v45y * 's4 - y4) - ('y-y4)*('X4 + 'v45x * 's4 - x4) = 0 \\ ('x-x4)*('Z4 + 'v45z * 's4 - z4) - ('z-z4)*('X4 + 'v45x * 's4 - x4) = 0 \\ ('x-x5)*('Y5 + 'v45y * 's5 - y5) - ('y-y5)*('X5 + 'v45x * 's5 - x5) = 0 \\ ('x-x5)*('Z5 + 'v45z * 's5 - z5) - ('z-z5)*('X5 + 'v45x * 's5 - x5) = 0 \\ ('x-x6)*('Y6 + 'v67y * 's6 - y6) - ('y-y6)*('X6 + 'v67x * 's6 - x6) = 0 \\ ('x-x6)*('Z6 + 'v67z * 's6 - z6) - ('z-z6)*('X6 + 'v67x * 's6 - x6) = 0 \\ ('x-x7)*('Y7 + 'v67y * 's7 - y7) - ('y-y7)*('X7 + 'v67x * 's7 - x7) = 0 \\ ('x-x7)*('Z7 + 'v67z * 's7 - z7) - ('z-z7)*('X7 + 'v67x * 's7 - x7) = 0 \\ ('x-x8)*('Y8 + 'v89y * 's8 - y8) - ('y-y8)*('X8 + 'v89x * 's8 - x8) = 0 \\ ('x-x8)*('Z8 + 'v89z * 's8 - z8) - ('z-z8)*('X8 + 'v89x * 's8 - x8) = 0 \\ ('x-x9)*('Y9 + 'v89y * 's9 - y9) - ('y-y9)*('X9 + 'v89x * 's9 - x9) = 0 \\ ('x-x9)*('Z9 + 'v89z * 's9 - z9) - ('z-z9)*('X9 + 'v89x * 's9 - x9) = 0 \end{cases}$$

$$\begin{cases} (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x0-x8)^2 - (y0-y8)^2 - (z0-z8)^2 - l08^2 = 0 \\ (x0-x9)^2 - (y0-y9)^2 - (z0-z9)^2 - l09^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x1-x8)^2 - (y1-y8)^2 - (z1-z8)^2 - l18^2 = 0 \\ (x1-x9)^2 - (y1-y9)^2 - (z1-z9)^2 - l19^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

further satisfying one of following mathematical equations:

$$\begin{cases} (x2-x8)^2 - (y2-y8)^2 - (z2-z8)^2 - l28^2 = 0 \\ (x2-x9)^2 - (y2-y9)^2 - (z2-z9)^2 - l29^2 = 0 \end{cases}$$

wherein ('x,'y,'z) are the coordinates of the x-ray source, (x0,y0,z0) through (x9,y9,z9) are the coordinates of the ten strut connection points to the fixation members, ('X0,'Y0,'Z0) to ('X1,'Y1,'Z1), . . . ('X8,'Y8,'Z8) to ('X9,'Y9,'Z9) are coordinates of the second set of the projections of the longitudinal axes of the struts on the second roentgenogram, and l01, l02, l03, l04, l06, l07, l08, l09, l12, l13, l14, l15, l16, l17, l18, l19, l23, l24, l25, l26, l27, l28, l29 are the predetermined distances between the strut connection points of the five struts, si are unknown ratios, and 'v(i−1)ix, 'v(i−1)iy, 'v(i−1)iz are the vectors of projections of the longitudinal axes of the struts, wherein 'v(i−1)ix, 'Xi−'X(i−1), 'v(i−1)iy, 'Yi−'Y(i−1), 'v0iz='Zi−'Z(i−1).

12. The method of claim 9, wherein the plurality of struts comprises four struts, and further wherein the first 3-D positions of the x-ray source and of the object are determined by satisfying following mathematical equations:

$$\begin{cases} (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

wherein (x0,y0,z0) through (x7,y7,z7) are coordinates of the eight strut connection points to the fixation members and l01, l02, l03, l04, l06, l07, l12, l13, l14, l15, l16, l17, l23, l24, l25, l26, l27 are the predetermined distances between the strut connection points of the four struts; and further wherein the second 3-D positions of the x-ray source and of the object are determined by satisfying following mathematical equations:

$$\begin{cases} (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

wherein (x0,y0,z0) through (x7,y7,z7) are the coordinates of the eight strut connection points to the fixation members and l01, l02, l03, l04, l06, l07, l12, l13, l14, l15, l16, l17, l23, l24, l25, l26, l27 are the predetermined distances between the strut connection points of the four struts.

13. The method of claim 9, wherein the plurality of struts comprises four struts, and further wherein the first 3-D positions of the x-ray source and of the object are determined by satisfying following mathematical equations:

$$\begin{cases} \begin{vmatrix} x0-x & y0-y & z0-z \\ X0-x & Y0-x & Z0-z \\ X1-x & Y1-y & Z1-z \end{vmatrix} = 0 \\[4pt] \begin{vmatrix} x1-x & y1-y & z1-z \\ X0-x & Y0-x & Z0-z \\ X1-x & Y1-y & Z1-z \end{vmatrix} = 0 \\[4pt] \begin{vmatrix} x2-x & y2-y & z2-z \\ X2-x & Y2-x & Z2-z \\ X3-x & Y3-y & Z3-z \end{vmatrix} = 0 \\[4pt] \begin{vmatrix} x3-x & y3-y & z3-z \\ X2-x & Y2-x & Z2-z \\ X3-x & Y3-y & Z3-z \end{vmatrix} = 0 \\[4pt] \begin{vmatrix} x4-x & y4-y & z4-z \\ X4-x & Y4-x & Z4-z \\ X5-x & Y5-y & Z5-z \end{vmatrix} = 0 \\[4pt] \begin{vmatrix} x5-x & y5-y & z5-z \\ X4-x & Y4-x & Z4-z \\ X5-x & Y5-y & Z5-z \end{vmatrix} = 0 \\[4pt] \begin{vmatrix} x6-x & y6-y & z6-z \\ X6-x & Y6-x & Z6-z \\ X7-x & Y7-y & Z7-z \end{vmatrix} = 0 \end{cases}$$

$$\left\{ \begin{array}{l} \left| \begin{array}{ccc} x7-x & y7-y & z7-z \\ X6-x & Y6-x & Z6-z \\ X7-x & Y7-y & Z7-z \end{array} \right| = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{array} \right.$$

wherein (x,y,z) are coordinates of the x-ray source, (x0,y0,z0) through (x7,y7,z7) are coordinates of the eight strut connection points to the fixation members, (X0,Y0,Z0) to (X1,Y1,Z1), . . . (X6,Y6,Z6) to (X7,Y7,Z7) are coordinates of a first set of projections of longitudinal axes of the struts on the first roentgenogram, and l01, l02, l03, l04, l06, l07, l12, l13, l14, l15, l16, l17, l23, l24, l25, l26, l27 are the predetermined distances between the strut connection points of the four struts; and further wherein the second 3-D positions of the x-ray source and of the object are determined by satisfying following mathematical equations:

$$\left\{ \begin{array}{l} \left| \begin{array}{ccc} x0-'x & y0-'y & z0-'z \\ 'X0-'x & 'Y0-'x & 'Z0-'z \\ 'X1-'x & 'Y1-'y & 'Z1-'z \end{array} \right| = 0 \\ \left| \begin{array}{ccc} x1-'x & y1-'y & z1-'z \\ 'X0-'x & 'Y0-'x & 'Z0-'z \\ 'X1-'x & 'Y1-'y & 'Z1-'z \end{array} \right| = 0 \\ \left| \begin{array}{ccc} x2-'x & y2-'y & z2-'z \\ 'X2-'x & 'Y2-'x & 'Z2-'z \\ 'X3-'x & 'Y3-'y & 'Z3-'z \end{array} \right| = 0 \\ \left| \begin{array}{ccc} x3-'x & y3-'y & z3-'z \\ 'X2-'x & 'Y2-'x & 'Z2-'z \\ 'X3-'x & 'Y3-'y & 'Z3-'z \end{array} \right| = 0 \\ \left| \begin{array}{ccc} x4-'x & y4-'y & z4-'z \\ 'X4-'x & 'Y4-'x & 'Z4-'z \\ 'X5-'x & 'Y5-'y & 'Z5-'z \end{array} \right| = 0 \\ \left| \begin{array}{ccc} x5-'x & y5-'y & z5-'z \\ 'X4-'x & 'Y4-'x & 'Z4-'z \\ 'X5-'x & 'Y5-'y & 'Z5-'z \end{array} \right| = 0 \\ \left| \begin{array}{ccc} x6-'x & y6-'y & z6-'z \\ 'X6-'x & 'Y6-'x & 'Z6-'z \\ 'X7-'x & 'Y7-'y & 'Z7-'z \end{array} \right| = 0 \\ \left| \begin{array}{ccc} x7-'x & y7-'y & z7-'z \\ 'X6-'x & 'Y6-'x & 'Z6-'z \\ 'X7-'x & 'Y7-'y & 'Z7-'z \end{array} \right| = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{array} \right.$$

wherein ('x,'y,'z) are the coordinates of the x-ray source, (x0,y0,z0) through (x7,y7,z7) are the coordinates of the eight strut connection points to the fixation members, ('X0,'Y0,Z0) to ('X1,Y1,Z1), . . . ('X6,'Y6,'Z6) to ('X7,'Y7,'Z7) are coordinates of a second set of projections of longitudinal axes of the struts on the second roentgenogram, and l01, l02, l03, l04, l06, l07, l12, l13, l14, l15, l16, l17, l23, l24, l25, l26, l27 are the predetermined distances between the strut connection points of the four struts.

14. The method of claim 9, further comprising:
identifying a first body part outline of the imaged body part in the first roentgenogram;

identifying a second body part outline of the imaged body part in the second roentgenogram;

preparing a first 3-D body part projection from the first body part outline to the first 3-D position of the x-ray source;

preparing a second 3-D body part projection from the second body part outline to the second 3-D position of the x-ray source;

creating a 3-D model of the imaged body part in the 3-D reference frame based on the first and second body part projections.

15. The method of claim 14, further comprising:

identifying a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation;

identifying one or more intersection planes passing through the tilt axis and through the first and second 3-D projections of the imaged body part in the 3-D reference frame;

for each of the one or more intersection planes, performing the following steps, a) through c):

a) identifying one or more intersection points between the first and second 3-D body part projections, and said intersection plane in the 3-D reference frame;

b) preparing one or more polygons connecting the intersection points in said intersection plane;

c) preparing one or more closed curves within the each of the one or more polygons, wherein the one or more closed curves corresponds to a cross-sectional view of the imaged body part in said intersection plane; and preparing a surface in the 3-D reference frame that connects each of the closed curves to form a 3-D model of the imaged body part.

16. A method of creating a 3-D model of an object, the object comprising a plurality of markers at predetermined distances along the object, the method comprising:

receiving a first roentgenogram of the object disposed between an x-ray source and an x-ray imager in a first orientation, wherein the first roentgenogram includes an image of:

the object, and the plurality of markers;

receiving a second roentgenogram of the object disposed between the x-ray source and the x-ray imager in a second orientation, wherein the second roentgenogram includes an image of:

the object, and the plurality of markers;

determining a first set of projections of the plurality of markers on the first roentgenogram;

determining a first 3-D position of the x-ray source and a first 3-D position of the object with respect to the x-ray imager in the first orientation by satisfying following mathematical equations:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z2-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein (x,y,z) are coordinates of the x-ray source, (x0,y0,z0) through (x3,y3,z3) are coordinates of the plurality of markers, (X0,Y0,Z0) through (X3,Y3,Z3) are coordinates of the first set of projections of the plurality of markers on the first roentgenogram, and l01, l02, l03, l04, l12, l13, l14, l23, l24, l34 are the predetermined distances between the plurality of markers to determine the distances between the plurality of markers and the first set of the projections of the plurality of markers on the first roentgenogram;

determining a second set of projections of the plurality of markers on the second roentgenogram;

determining a second 3-D position of the x-ray source and a second 3-D position of the object with respect to the x-ray imager in the second orientation by satisfying following mathematical equations:

$$\begin{cases} ('x-x0)*('Y0-y0)-('y-y0)-('X0-x0)=0 \\ ('x-x0)*('Z0-z0)-('z-z0)-('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-z2)-('y-y2)*('X2-x2)=0 \\ ('x-x2)*('Z1-z2)-('z-z2)*('X2-x2)=0 \\ ('x-x3)*('Y3-z3)-('y-y3)*('X3-x3)=0 \\ ('x-x3)*('Z3-z3)-('z-z3)*('X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein ('x,'y,'z) are coordinates of the x-ray source, (x0,y0,z0) through (x3,y3,z3) are coordinates of the plurality of markers, ('X0,'Y0,'Z0) through ('X3,'Y3,'Z3) are coordinates of the second set of projections of the plurality of markers on the second roentgenogram, and l01, l02, l03, l04, l12, l13, l14, l23, l24, l34 are the predetermined distances between the plurality of markers to determine the distances between the plurality of markers and the second set of projections of the plurality of markers on the second roentgenogram;

aligning the first and second 3-D object projections in a 3-D reference frame using the 3-D positions of the plurality of markers with respect to the x-ray imager in the first and second orientations; and creating a 3-D model of the imaged object in the 3-D reference frame based on the first and second 3-D object projections.

17. The method of claim 16, wherein the plurality of markers comprises a plurality of joints where a plurality of struts are connected to at least one fixation member.

18. The method of claim 16, wherein the object is an orthopedic fixator.

19. The method of claim 16, wherein the plurality of markers comprises five markers, and further wherein the first 3-D positions of the x-ray source and of the object are determined by satisfying following mathematical equations:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z2-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x-x4)*(Y4-y4)-(y-y4)*(X4-x4)=0 \\ (x-x4)*(Z4-z4)-(z-z4)*(X4-x4)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x2-x3)^2-(y2-y3)^2-(z2-z3)^2-l23^2=0 \end{cases}$$

further satisfying one of following mathematical equations:

$$\begin{cases} (x2-x3)^2-(y2-y3)^2-(z2-z3)^2-l23^2=0, \\ (x2-x4)^2-(y2-y4)^2-(z2-z4)^2-l24^2=0, \\ (x3-x4)^2-(y3-y4)^2-(32-z4)^2-l34^2=0. \end{cases}$$

wherein (x,y,z) are coordinates of the x-ray source, (x0,y0,z0) through (x4,y4,z4) are coordinates of the five markers, (X0,Y0,Z0) through (X4,Y4,Z4) are coordinates of the first set of projections of the five markers on the first roentgenogram, and l01, l02, l03, l04, l12, l13, l14, l23, l24, l34 are the predetermined distances between the five markers; and further wherein the second 3-D positions of the x-ray source and of the object are determined by satisfying following mathematical equations:

$$\begin{cases} ('x-x0)*('Y0-y0)-('y-y0)*('X0-x0)=0 \\ ('x-x0)*('Z0-z0)-('z-z0)*('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-y2)-('y-y2)*('X2-x2)=0 \\ ('x-x2)*('Z2-z2)-('z-z2)*('X2-x2)=0 \\ ('x-x3)*('Y3-y3)-('y-y3)*('X3-x3)=0 \\ ('x-x3)*('Z3-z3)-('z-z3)*('X3-x3)=0 \\ ('x-x4)*('Y4-y4)-('y-y4)*('X4-x4)=0 \\ ('x-x4)*('Z4-z4)-('z-z4)*('X4-x4)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x2-x3)^2-(y2-y3)^2-(z2-z3)^2-l23^2=0 \end{cases}$$

further satisfying one of following mathematical equations:

$$\begin{cases} (x2-x3)^2-(y2-y3)^2-(z2-z3)^2-l23^2=0, \\ (x2-x4)^2-(y2-y4)^2-(z2-z4)^2-l24^2=0, \\ (x3-x4)^2-(y3-y4)^2-(32-z4)^2-l34^2=0. \end{cases}$$

wherein ('x,'y,'z) are the coordinates of the x-ray source, (x0,y0,z0) through (x4,y4,z4) are the coordinates of the five markers, ('X0,'Y0,'Z0) through ('X4,'Y4,'Z4) are coordinates of the second set of the projections of the five markers on the second roentgenogram, and l01, l02, l03, l04, l12, l13, l14, l23, l24, l34 are the predetermined distances between the five markers.

20. The method of claim 16, wherein the plurality of markers comprises four markers, and further wherein the first 3-D positions of the x-ray source and of the object are determined by-satisfying following mathematical equations:

$$\begin{cases} (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein (x0,y0,z0) through (x3,y3,z3) are coordinates of the four markers and l01, l02, l03, l12, l13, l23 are the predetermined distances between the four markers; and further wherein the second 3-D positions of the x-ray source and of the object are determined by satisfying following mathematical equations:

$$\begin{cases} (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x2-x3)^2 - (y2-y3)^2 - (z2-z3)^2 - l23^2 = 0 \end{cases}$$

wherein (x0,y0,z0) through (x3,y3,z3) are the coordinates of the four markers and l01, l02, l03, l12, l13, l23 are the predetermined distances between the four markers.

21. The method of claim 16, wherein the plurality of markers comprises four markers, and further wherein the first 3-D positions of the x-ray source and of the object are determined by satisfying following mathematical equations:

$$\begin{cases} \begin{vmatrix} x0-x & y0-y & z0-z \\ X0-x & Y0-y & Z0-z \\ X1-x & Y1-y & Z1-z \end{vmatrix} = 0 \\ \begin{vmatrix} x1-x & y1-y & z1-z \\ X0-x & Y0-x & Z0-z \\ X1-x & Y1-y & Z1-z \end{vmatrix} = 0 \\ \begin{vmatrix} x1-x & y1-y & z1-z \\ X1-x & Y1-x & Z1-z \\ X2-x & Y2-y & Z2-z \end{vmatrix} = 0 \\ \begin{vmatrix} x2-x & y2-y & z2-z \\ X1-x & Y1-x & Z1-z \\ X2-x & Y2-y & Z2-z \end{vmatrix} = 0 \\ \begin{vmatrix} x2-x & y2-y & z2-z \\ X2-x & Y2-x & Z2-z \\ X3-x & Y3-y & Z3-z \end{vmatrix} = 0 \\ \begin{vmatrix} x3-x & y3-y & z3-z \\ X2-x & Y2-x & Z2-z \\ X3-x & Y3-y & Z3-z \end{vmatrix} = 0 \\ \begin{vmatrix} x3-x & y3-y & z3-z \\ X3-x & Y3-x & Z3-z \\ X0-x & Y0-y & Z0-z \end{vmatrix} = 0 \\ \begin{vmatrix} x0-x & y0-y & z0-z \\ X3-x & Y3-x & Z3-z \\ X0-x & Y0-y & Z0-z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x2-x3)^2 - (y2-y3)^2 - (z2-z3)^2 - l23^2 = 0 \end{cases}$$

wherein (x,y,z) are coordinates of the x-ray source, (x0,y0,z0) through (x3,y3,z3) are coordinates of the four markers, (X0,Y0,Z0) through (X3,Y3,Z3) are coordinates of the first set of the projections of the four markers on the first roentgenogram, and l01, l02, l03, l12, l13, l23 are the predetermined distances between the four markers; and further wherein the second 3-D positions of the x-ray source and of the object are determined by satisfying following mathematical equations:

$$\begin{cases} \begin{vmatrix} x0-'x & y0-'y & z0-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X1-'x & 'Y1-'x & 'Z1-'z \\ 'X2-'x & 'Y2-'y & 'Z2-'z \end{vmatrix} = 0 \\ \begin{vmatrix} x2-'x & y2-'y & z2-'z \\ 'X1-'x & 'Y1-'x & 'Z1-'z \\ 'X2-'x & 'Y2-'y & 'Z2-'z \end{vmatrix} = 0 \\ \begin{vmatrix} x2-'x & y2-'y & z2-'z \\ 'X2-'x & 'Y2-'x & 'Z2-'z \\ 'X3-'x & 'Y3-'y & 'Z3-'z \end{vmatrix} = 0 \\ \begin{vmatrix} x3-'x & y3-'y & z3-'z \\ 'X2-'x & 'Y2-'x & 'Z2-'z \\ 'X3-'x & 'Y3-'y & 'Z3-'z \end{vmatrix} = 0 \\ \begin{vmatrix} x3-'x & y3-'y & z3-'z \\ 'X3-'x & 'Y3-'x & 'Z3-'z \\ 'X0-'x & 'Y0-'y & 'Z0-'z \end{vmatrix} = 0 \\ \begin{vmatrix} x0-'x & y0-'y & z0-'z \\ 'X3-'x & 'Y3-'x & 'Z3-'z \\ 'X0-'x & 'Y0-'y & 'Z0-'z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x2-x3)^2 - (y2-y3)^2 - (z2-z3)^2 - l23^2 = 0 \end{cases}$$

wherein, ('x,'y,'z) are the coordinates of the x-ray source, (x0,y0,z0) through (x3,y3,z3) are the coordinates of the four markers, ('X0,'Y0,'Z0) through ('X3,'Y3,'Z3) are coordinates of the second set of the projections of the four markers on the second roentgenogram, and l01, l02, l03, l12, l13, l23 are the predetermined distances between the four markers.

22. A method of creating a 3-D model of an object, the object comprising a plurality of struts with predetermined lengths that are each connected to at least two fixation members with predetermined dimensions, the method comprising:

receiving a first roentgenogram of the object disposed between an x-ray source and an x-ray imager in a first orientation, wherein the first roentgenogram includes an image of:

the object, and the plurality of struts with predetermined lengths that are each connected to the at least two fixation members at two connection points, wherein the distances between the two connection points are predetermined;

receiving a second roentgenogram of the object disposed between the x-ray source and the x-ray imager in a second orientation, wherein the second roentgenogram includes an image of:

the object, and the plurality of struts with predetermined lengths that are each connected to the at least two fixation members at two connection points, wherein the distances between the two connection points are predetermined;

determining a first set of projections of longitudinal axes of the plurality of struts on the first roentgenogram;

determining a first 3-D position of the x-ray source and a first 3-D position of the object with respect to the x-ray imager by satisfying following mathematical equations:

$$\begin{cases} (x-x0)*(Y'0-y0)-(y-y0)*(X'0-x0)=0 \\ (x-x0)*(Z'0-z0)-(z-z0)*(X'0-x0)=0 \\ (x-x1)*(Y'1-y1)-(y-y1)*(X'1-x1)=0 \\ (x-x1)*(Z'1-z1)-(z-z1)*(X'1-x1)=0 \\ (x-x2)*(Y'2-y2)-(y-y2)*(X'2-x2)=0 \\ (x-x2)*(Z'1-z2)-(z-z2)*(X'2-x2)=0 \\ (x-x3)*(Y'3-y3)-(y-y3)*(X'3-x3)=0 \\ (x-x3)*(Z'3-z3)-(z-z3)*(X'3-x3)=0 \\ (x-x4)*(Y'4-y4)-(y-y4)*(X'4-x4)=0 \\ (x-x4)*(Z'4-z4)-(z-z4)*(X'4-x4)=0 \\ (x-x5)*(Y'5-y5)-(y-y5)*(X'5-x5)=0 \\ (x-x5)*(Z'5-z5)-(z-z5)*(X'5-x5)=0 \\ (x-x6)*(Y'6-y6)-(y-y6)*(X'6-x6)=0 \\ (x-x6)*(Z'6-z6)-(z-z6)*(X'6-x6)=0 \\ (x-x7)*(Y'7-y7)-(y-y7)*(X'7-x7)=0 \\ (x-x7)*(Z'7-z7)-(z-z7)*(X'7-x7)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x0-x5)^2-(y0-y5)^2-(z0-z5)^2-l05^2=0 \\ (x0-x6)^2-(y0-y6)^2-(z0-z6)^2-l06^2=0 \\ (x0-x7)^2-(y0-y7)^2-(z0-z7)^2-l07^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x1-x5)^2-(y1-y5)^2-(z1-z5)^2-l15^2=0 \\ (x1-x6)^2-(y1-y6)^2-(z1-z6)^2-l16^2=0 \\ (x1-x7)^2-(y1-y7)^2-(z1-z7)^2-l17^2=0 \\ (x2-x3)^2-(y2-y3)^2-(z2-z3)^2-l23^2=0 \\ (x2-x4)^2-(y2-y4)^2-(z2-z4)^2-l24^2=0 \\ (x2-x5)^2-(y2-y5)^2-(z2-z5)^2-l25^2=0 \\ (x2-x6)^2-(y2-y6)^2-(z2-z6)^2-l26^2=0 \\ (x2-x7)^2-(y2-y7)^2-(z2-z7)^2-l27^2=0 \end{cases}$$

wherein (x,y,z) are coordinates of the x-ray source, (x0,y0,z0) through (x7,y7,z7) are coordinates of the eight strut connection points to the fixation members, (X0,Y0,Z0) to (X1,Y1,Z1), . . . (X6,Y6,Z6) to (X7,Y7,Z7) are coordinates of a first set of projections of longitudinal axes of the plurality of struts on the first roentgenogram, (X'0,Y'0,Z'0) through (X'7,Y'7,Z'7) are coordinates of a first set of projections of the eight strut connection points on the first roentgenogram, and l01, l02, l03, l04, l06, l07, l12, l13, l14, l15, l16, l17, l23, l24, l25, l26, l27 are the predetermined distances between the strut connection points of the four struts, si are unknown ratios, and v(i−1)ix, v(i−1)iy, v(i−1)iz are vectors of projections of the longitudinal axes of the struts, wherein v(i−1)ix=Xi−X(i−1), v(i−1)iy=Yi−Y(i−1), v0iz=Zi−Z(i−1);

determining a second set of projections of longitudinal axes of the plurality of struts on the second roentgenogram;

determining a second 3-D position of the x-ray source and a second 3-D position of the object with respect to the x-ray imager by satisfying following mathematical equations:

$$\begin{cases} ('x-x0)*('Y0-y0)-('y-y0)*('X0-x0)=0 \\ ('x-x0)*('Z0-z0)-('z-z0)*('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-y2)-('y-y2)*('X2-x2)=0 \\ ('x-x2)*('Z1-z2)-('z-z2)*('X2-x2)=0 \\ ('x-x3)*('Y3-y3)-('y-y3)*('X3-x3)=0 \\ ('x-x3)*('Z3-z3)-('z-z3)*('X3-x3)=0 \\ ('x-x4)*('Y4-y4)-('y-y4)*('X4-x4)=0 \\ ('x-x4)*('Z4-z4)-('z-z4)*('X4-x4)=0 \\ ('x-x5)*('Y5-y5)-('y-y5)*('X5-x5)=0 \\ ('x-x5)*('Z5-z5)-('z-z5)*('X5-x5)=0 \\ ('x-x6)*('Y6-y6)-('y-y6)*('X6-x6)=0 \\ ('x-x6)*('Z6-z6)-('z-z6)*('X6-x6)=0 \\ ('x-x7)*('Y7-y7)-('y-y7)*('X7-x7)=0 \\ ('x-x7)*('Z7-z7)-('z-z7)*('X7-x7)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x0-x5)^2-(y0-y5)^2-(z0-z5)^2-l05^2=0 \\ (x0-x6)^2-(y0-y6)^2-(z0-z6)^2-l06^2=0 \\ (x0-x7)^2-(y0-y7)^2-(z0-z7)^2-l07^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x1-x5)^2-(y1-y5)^2-(z1-z5)^2-l15^2=0 \\ (x1-x6)^2-(y1-y6)^2-(z1-z6)^2-l16^2=0 \\ (x1-x7)^2-(y1-y7)^2-(z1-z7)^2-l17^2=0 \\ (x2-x3)^2-(y2-y3)^2-(z2-z3)^2-l23^2=0 \\ (x2-x4)^2-(y2-y4)^2-(z2-z4)^2-l24^2=0 \\ (x2-x5)^2-(y2-y5)^2-(z2-z5)^2-l25^2=0 \\ (x2-x6)^2-(y2-y6)^2-(z2-z6)^2-l26^2=0 \\ (x2-x7)^2-(y2-y7)^2-(z2-z7)^2-l27^2=0 \end{cases}$$

wherein ('x,'y,'z) are the coordinates of the x-ray source, (x0,y0,z0) through (x7,y7,z7) are the coordinates of the eight strut connection points to the fixation members, ('X0,'Y0,'Z0) to ('X1,'Y1,'Z1), . . . ('X6,'Y6,'Z6) to ('X7,'Y7,'Z7) are coordinates of a second set of projections of longitudinal axes of the struts on the second roentgenogram, ('X'0,'Y'0,'Z'0) through ('X'7,'Y'7,'Z'7) are coordinates of a second set of projections of the eight strut connection points on the second roentgenogram, and l01, l02, l03, l04, l06, l07, l12, l13, l14, l15, l16, l17, l23, l24, l25, l26, l27 are the predetermined distances between the strut connection points of the four struts, si are unknown ratios, and 'v(i−1)ix, 'v(i−1)iy, 'v(i−1)iz are vectors of projections of the longitudinal axes of the struts, wherein 'v(i−1)ix='Xi−'X(i−1), 'v(i−1)iy, 'Yi−'Y(i−1), 'v0iz, 'Zi−'Z(i−1);

aligning the first and second 3-D object projections in a 3-D reference frame using the 3-D positions of the plurality of struts with respect to the x-ray imager in the first and second orientations; and creating a 3-D model of the imaged object in the 3-D reference frame based on the first and second 3-D object projections.

23. The method of claim 22, wherein the object is an orthopedic fixator.

24. The method of claim 22, wherein the plurality of struts comprises five struts, and further wherein the first 3-D positions of the x-ray source and of the object are determined by satisfying following mathematical equations:

$$\begin{cases} (x-x0)*(Y0+v01y*s0-y0)-(y-y0)*(X0+v01x*s0-x0)=0 \\ (x-x0)*(Z0+v01z*s0-z0)-(z-z0)*(X0+v01x*s0-x0)=0 \\ (x-x1)*(Y1+v01y*s1-y1)-(y-y1)*(X1+v01x*s1-x1)=0 \\ (x-x1)*(Z1+v01z*s1-z1)-(z-z1)*(X1+v01x*s1-x1)=0 \\ (x-x2)*(Y2+v23y*s2-y2)-(y-y2)*(X2+v23x*s2-x2)=0 \\ (x-x2)*(Z2+v23z*s2-z2)-(z-z2)*(X2+v23x*s2-x2)=0 \\ (x-x3)*(Y3+v23y*s3-y3)-(y-y3)*(X3+v23x*s3-x3)=0 \\ (x-x3)*(Z3+v23z*s3-z3)-(z-z3)*(X3+v23x*s3-x3)=0 \\ (x-x4)*(Y4+v45y*s4-y4)-(y-y4)*(X4+v45x*s4-x4)=0 \\ (x-x4)*(Z4+v45z*s4-z4)-(z-z4)*(X4+v45x*s4-x4)=0 \\ (x-x5)*(Y5+v45y*s5-y5)-(y-y5)*(X5+v45x*s5-x5)=0 \\ (x-x5)*(Z5+v45z*s5-z5)-(z-z5)*(X5+v45x*s5-x5)=0 \\ (x-x6)*(Y6+v67y*s6-y6)-(y-y6)*(X6+v67x*s6-x6)=0 \\ (x-x6)*(Z6+v67z*s6-z6)-(z-z6)*(X6+v67x*s6-x6)=0 \\ (x-x7)*(Y7+v67y*s7-y7)-(y-y7)*(X7+v67x*s7-x7)=0 \\ (x-x7)*(Z7+v67z*s7-z7)-(z-z7)*(X7+v67x*s7-x7)=0 \\ (x-x8)*(Y8+v89y*s8-y8)-(y-y8)*(X8+v89x*s8-x8)=0 \\ (x-x8)*(Z8+v89z*s8-z8)-(z-z8)*(X8+v89x*s8-x8)=0 \\ (x-x9)*(Y9+v89y*s9-y9)-(y-y9)*(X9+v89x*s9-x9)=0 \\ (x-x9)*(Z9+v89z*s9-z9)-(z-z9)*(X9+v89x*s9-x9)=0 \end{cases}$$

$$\begin{cases} (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x0-x4)^2-(y0-y4)^2-(z0-z4)^2-l04^2=0 \\ (x0-x5)^2-(y0-y5)^2-(z0-z5)^2-l05^2=0 \\ (x0-x6)^2-(y0-y6)^2-(z0-z6)^2-l06^2=0 \\ (x0-x7)^2-(y0-y7)^2-(z0-z7)^2-l07^2=0 \\ (x0-x8)^2-(y0-y8)^2-(z0-z8)^2-l08^2=0 \\ (x0-x9)^2-(y0-y9)^2-(z0-z9)^2-l09^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x1-x4)^2-(y1-y4)^2-(z1-z4)^2-l14^2=0 \\ (x1-x5)^2-(y1-y5)^2-(z1-z5)^2-l15^2=0 \\ (x1-x6)^2-(y1-y6)^2-(z1-z6)^2-l16^2=0 \\ (x1-x7)^2-(y1-y7)^2-(z1-z7)^2-l17^2=0 \\ (x1-x8)^2-(y1-y8)^2-(z1-z8)^2-l18^2=0 \\ (x1-x9)^2-(y1-y9)^2-(z1-z9)^2-l19^2=0 \\ (x2-x3)^2-(y2-y3)^2-(z2-z3)^2-l23^2=0 \\ (x2-x4)^2-(y2-y4)^2-(z2-z4)^2-l24^2=0 \\ (x2-x5)^2-(y2-y5)^2-(z2-z5)^2-l25^2=0 \\ (x2-x6)^2-(y2-y6)^2-(z2-z6)^2-l26^2=0 \\ (x2-x7)^2-(y2-y7)^2-(z2-z7)^2-l27^2=0 \end{cases}$$

further satisfying one of following mathematical equations:

$$\begin{cases} (x2-x8)^2-(y2-y8)^2-(z2-z8)^2-l28^2=0 \\ (x2-x9)^2-(y2-y9)^2-(z2-z9)^2-l29^2=0 \end{cases}$$

wherein (x,y,z) are coordinates of the x-ray source, (x0, y0,z0) through (x9,y9,z9) are coordinates of the ten strut connection points to the fixation members, (X0, Y0,Z0) to (X1,Y1,Z1), . . . (X8,Y8,Z8) to (X9,Y9,Z9) are coordinates of the first set of the projections of the longitudinal axes of the struts on the first roentgenogram, and l01, l02, l03, l04, l06, l07, l08, l09, l12, l13, l14, l15, l16, l17, l18, l19, l23, l24, l25, l26, l27, l28, l29 are the predetermined distances between the strut connection points of the five struts, si are unknown ratios, and v(i−1)ix, v(i−1)iy, v(i−1)iz are vectors of projections of longitudinal axes of the struts, wherein v(i−1)ix, Xi−X(i−1), v(i−1)iy, Yi−Y(i−1), v0iz=Zi−Z(i−1); and further wherein the second 3-D positions of the x-ray source and of the object are determined by satisfying following mathematical equations:

$$\begin{cases}
('x-x0)*('Y0+'v01y*'s0-y0)-('y-y0)*('X0+'v01x*'s0-x0)=0 \\
('x-x0)*('Z0+'v01z*'s0-z0)-('z-z0)*('X0+'v01x*'s0-x0)=0 \\
('x-x1)*('Y1+'v01y*'s1-y1)-('y-y1)*('X1+'v01x*'s1-x1)=0 \\
('x-x1)*('Z1+'v01z*'s1-z1)-('z-z1)*('X1+'v01x*'s1-x1)=0 \\
('x-x2)*('Y2+'v23y*'s2-y2)-('y-y2)*('X2+'v23x*'s2-x2)=0 \\
('x-x2)*('Z2+'v23z*'s2-z2)-('z-z2)*('X2+'v23x*'s2-x2)=0 \\
('x-x3)*('Y3+'v23y*'s3-y3)-('y-y3)*('X3+'v23x*'s3-x3)=0 \\
('x-x3)*('Z3+'v23z*'s3-z3)-('z-z3)*('X3+'v23x*'s3-x3)=0 \\
('x-x4)*('Y4+'v45y*'s4-y4)-('y-y4)*('X4+'v45x*'s4-x4)=0 \\
('x-x4)*('Z4+'v45z*'s4-z4)-('z-z4)*('X4+'v45x*'s4-x4)=0 \\
('x-x5)*('Y5+'v45y*'s5-y5)-('y-y5)*('X5+'v45x*'s5-x5)=0 \\
('x-x5)*('Z5+'v45z*'s5-z5)-('z-z5)*('X5+'v45x*'s5-x5)=0 \\
('x-x6)*('Y6+'v67y*'s6-y6)-('y-y6)*('X6+'v67x*'s6-x6)=0 \\
('x-x6)*('Z6+'v67z*'s6-z6)-('z-z6)*('X6+'v67x*'s6-x6)=0 \\
('x-x7)*('Y7+'v67y*'s7-y7)-('y-y7)*('X7+'v67x*'s7-x7)=0 \\
('x-x7)*('Z7+'v67z*'s7-z7)-('z-z7)*('X7+'v67x*'s7-x7)=0 \\
('x-x8)*('Y8+'v89y*'s8-y8)-('y-y8)*('X8+'v89x*'s8-x8)=0 \\
('x-x8)*('Z8+'v89z*'s8-z8)-('z-z8)*('X8+'v89x*'s8-x8)=0 \\
('x-x9)*('Y9+'v89y*'s9-y9)-('y-y9)*('X9+'v89x*'s9-x9)=0 \\
('x-x9)*('Z9+'v89z*'s9-z9)-('z-z9)*('X9+'v89x*'s9-x9)=0
\end{cases}$$

$$\begin{cases}
(x0-x1)^2-(y0-y1)^2-(z0-z1)^2-l01^2=0 \\
(x0-x2)^2-(y0-y2)^2-(z0-z2)^2-l02^2=0 \\
(x0-x3)^2-(y0-y3)^2-(z0-z3)^2-l03^2=0 \\
(x0-x4)^2-(y0-y4)^2-(z0-z4)^2-l04^2=0 \\
(x0-x5)^2-(y0-y5)^2-(z0-z5)^2-l05^2=0 \\
(x0-x6)^2-(y0-y6)^2-(z0-z6)^2-l06^2=0 \\
(x0-x7)^2-(y0-y7)^2-(z0-z7)^2-l07^2=0 \\
(x0-x8)^2-(y0-y8)^2-(z0-z8)^2-l08^2=0 \\
(x0-x9)^2-(y0-y9)^2-(z0-z9)^2-l09^2=0 \\
(x1-x2)^2-(y1-y2)^2-(z1-z2)^2-l12^2=0 \\
(x1-x3)^2-(y1-y3)^2-(z1-z3)^2-l13^2=0 \\
(x1-x4)^2-(y1-y4)^2-(z1-z4)^2-l14^2=0 \\
(x1-x5)^2-(y1-y5)^2-(z1-z5)^2-l15^2=0 \\
(x1-x6)^2-(y1-y6)^2-(z1-z6)^2-l16^2=0 \\
(x1-x7)^2-(y1-y7)^2-(z1-z7)^2-l17^2=0 \\
(x1-x8)^2-(y1-y8)^2-(z1-z8)^2-l18^2=0 \\
(x1-x9)^2-(y1-y9)^2-(z1-z9)^2-l19^2=0 \\
(x2-x3)^2-(y2-y3)^2-(z2-z3)^2-l23^2=0 \\
(x2-x4)^2-(y2-y4)^2-(z2-z4)^2-l24^2=0 \\
(x2-x5)^2-(y2-y5)^2-(z2-z5)^2-l25^2=0 \\
(x2-x6)^2-(y2-y6)^2-(z2-z6)^2-l26^2=0 \\
(x2-x7)^2-(y2-y7)^2-(z2-z7)^2-l27^2=0
\end{cases}$$

further satisfying one of following mathematical equations:

$$\begin{cases}
(x2-x8)^2-(y2-y8)^2-(z2-z8)^2-l28^2=0 \\
(x2-x9)^2-(y2-y9)^2-(z2-z9)^2-l29^2=0
\end{cases}$$

wherein ('x,'y,'z) are the coordinates of the x-ray source, (x0,y0,z0) through (x9,y9,z9) are the coordinates of the ten strut connection points to the fixation members, ('X0,'Y0,'Z0) to ('X1,'Y1,'Z1), . . . ('X8,'Y8,'Z8) to ('X9,'Y9,'Z9) are coordinates of the second set of the projections of the longitudinal axes of the struts on the second roentgenogram, and l01, l02, l03, l04, l06, l07, l08, l09, l12, l13, l14, l15, l16, l17, l18, l19, l23, l24, l25, l26, l27, l28, l29 are the predetermined distances between the strut connection points of the five struts, si are unknown ratios, and 'v(i−1)ix, 'v(i−1)iy, 'v(i−1)iz are the vectors of projections of the longitudinal axes of the struts, wherein 'v(i−1)ix, 'Xi−'X(i−1), 'v(i−1)iy, 'Yi−'Y(i−1), 'v0iz, 'Zi−'Z(i−1).

25. The method of claim 22, wherein the plurality of struts comprises four struts, and further wherein the first 3-D positions of the x-ray source and of the object are determined by satisfying following mathematical equations:

$$\begin{cases} (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

wherein (x0,y0,z0) through (x7,y7,z7) are coordinates of the eight strut connection points to the fixation members and l01, l02, l03, l04, l06, l07, l12, l13, l14, l15, l16, l17, l23, l24, l25, l26, l27 are the predetermined distances between the strut connection points of the four struts; and further wherein the second 3-D positions of the x-ray source and of the object are determined by satisfying following mathematical equations:

$$\begin{cases} (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

wherein (x0,y0,z0) through (x7,y7,z7) are the coordinates of the eight strut connection points to the fixation members and l01, l02, l03, l04, l06, l07, l12, l13, l14, l15, l16, l17, l23, l24, l25, l26, l27 are the predetermined distances between the strut connection points of the four struts.

26. The method of claim 22, wherein the plurality of struts comprises four struts, and further wherein the first 3-D positions of the x-ray source and of the object are determined by satisfying following mathematical equations:

$$\begin{cases} \begin{vmatrix} x0-x & y0-y & z0-z \\ X0-x & Y0-x & Z0-z \\ X1-x & Y1-y & Z1-z \end{vmatrix} = 0 \\ \begin{vmatrix} x1-x & y1-y & z1-z \\ X0-x & Y0-x & Z0-z \\ X1-x & Y1-y & Z1-z \end{vmatrix} = 0 \\ \begin{vmatrix} x2-x & y2-y & z2-z \\ X2-x & Y2-x & Z2-z \\ X3-x & Y3-y & Z3-z \end{vmatrix} = 0 \\ \begin{vmatrix} x3-x & y3-y & z3-z \\ X2-x & Y2-x & Z2-z \\ X3-x & Y3-y & Z3-z \end{vmatrix} = 0 \\ \begin{vmatrix} x4-x & y4-y & z4-z \\ X4-x & Y4-x & Z4-z \\ X5-x & Y5-y & Z5-z \end{vmatrix} = 0 \\ \begin{vmatrix} x5-x & y5-y & z5-z \\ X4-x & Y4-x & Z4-z \\ X5-x & Y5-y & Z5-z \end{vmatrix} = 0 \\ \begin{vmatrix} x6-x & y6-y & z6-z \\ X6-x & Y6-x & Z6-z \\ X7-x & Y7-y & Z7-z \end{vmatrix} = 0 \\ \begin{vmatrix} x7-x & y7-y & z7-z \\ X6-x & Y6-x & Z6-z \\ X7-x & Y7-y & Z7-z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

wherein (x,y,z) are coordinates of the x-ray source, (x0, y0,z0) through (x7,y7,z7) are coordinates of the eight strut connection points to the fixation members, (X0, Y0,Z0) to (X1,Y1,Z1), . . . (X6,Y6,Z6) to (X7,Y7,Z7) are coordinates of the first set of projections of longitudinal axes of the struts on the first roentgenogram, and l01, l02, l03, l04, l06, l07, l12, l13, l14, l15, l16, l17, l23, l24, l25, l26, l27 are the predetermined distances between the strut connection points of the four struts; and further wherein the second 3-D positions of the x-ray source and of the object are determined by satisfying following mathematical equations:

$$\begin{cases} \begin{vmatrix} x0-'x & y0-'y & z0-'z \\ 'X0-'x & 'Y0-'x & 'Z0-'z \\ 'X1-'x & 'Y1-'y & 'Z1-'z \end{vmatrix} = 0 \\ \begin{vmatrix} x1-'x & y1-'y & z1-'z \\ 'X0-'x & 'Y0-'x & 'Z0-'z \\ 'X1-'x & 'Y1-'y & 'Z1-'z \end{vmatrix} = 0 \\ \begin{vmatrix} x2-'x & y2-'y & z2-'z \\ 'X2-'x & 'Y2-'x & 'Z2-'z \\ 'X3-'x & 'Y3-'y & 'Z3-'z \end{vmatrix} = 0 \\ \begin{vmatrix} x3-'x & y3-'y & z3-'z \\ 'X2-'x & 'Y2-'x & 'Z2-'z \\ 'X3-'x & 'Y3-'y & 'Z3-'z \end{vmatrix} = 0 \\ \begin{vmatrix} x4-'x & y4-'y & z4-'z \\ 'X4-'x & 'Y4-'x & 'Z4-'z \\ 'X5-'x & 'Y5-'y & 'Z5-'z \end{vmatrix} = 0 \\ \begin{vmatrix} x5-'x & y5-'y & z5-'z \\ 'X4-'x & 'Y4-'x & 'Z4-'z \\ 'X5-'x & 'Y5-'y & 'Z5-'z \end{vmatrix} = 0 \\ \begin{vmatrix} x6-'x & y6-'y & z6-'z \\ 'X6-'x & 'Y6-'x & 'Z6-'z \\ 'X7-'x & 'Y7-'y & 'Z7-'z \end{vmatrix} = 0 \\ \begin{vmatrix} x7-'x & y7-'y & z7-'z \\ 'X6-'x & 'Y6-'x & 'Z6-'z \\ 'X7-'x & 'Y7-'y & 'Z7-'z \end{vmatrix} = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x0-x4)^2 - (y0-y4)^2 - (z0-z4)^2 - l04^2 = 0 \\ (x0-x5)^2 - (y0-y5)^2 - (z0-z5)^2 - l05^2 = 0 \\ (x0-x6)^2 - (y0-y6)^2 - (z0-z6)^2 - l06^2 = 0 \\ (x0-x7)^2 - (y0-y7)^2 - (z0-z7)^2 - l07^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x1-x4)^2 - (y1-y4)^2 - (z1-z4)^2 - l14^2 = 0 \\ (x1-x5)^2 - (y1-y5)^2 - (z1-z5)^2 - l15^2 = 0 \\ (x1-x6)^2 - (y1-y6)^2 - (z1-z6)^2 - l16^2 = 0 \\ (x1-x7)^2 - (y1-y7)^2 - (z1-z7)^2 - l17^2 = 0 \\ (x2-x3)^2 - (y2-y3)^2 - (z2-z3)^2 - l23^2 = 0 \\ (x2-x4)^2 - (y2-y4)^2 - (z2-z4)^2 - l24^2 = 0 \\ (x2-x5)^2 - (y2-y5)^2 - (z2-z5)^2 - l25^2 = 0 \\ (x2-x6)^2 - (y2-y6)^2 - (z2-z6)^2 - l26^2 = 0 \\ (x2-x7)^2 - (y2-y7)^2 - (z2-z7)^2 - l27^2 = 0 \end{cases}$$

wherein ('x,'y,'z) are the coordinates of the x-ray source, (x0,y0,z0) through (x7,y7,z7) are the coordinates of the eight strut connection points to the fixation members, ('X0,'Y0,'Z0) to ('X1,'Y1,'Z1), . . . ('X6,'Y6,'Z6) to ('X7, 'Y7,'Z7) are coordinates of the second set of projections of the longitudinal axes of the struts on the second roentgenogram, and l01, l02, l03, l04, l06, l07, l12, l13, l14, l15, l16, l17, l23, l24, l25, l26, l27 are the predetermined distances between the strut connection points of the four struts.

27. A computer memory device encoded with instructions for causing a computer to perform the following steps:

receiving a first roentgenogram of the body part and the object disposed between an x-ray source and an x-ray imager in a first orientation, wherein the first roentgenogram includes an image of:

the body part, the object, and the plurality of markers;

receiving a second roentgenogram of the body part and the object disposed between the x-ray source and the x-ray imager in a second orientation, wherein the second roentgenogram includes an image of:

the body part, the object, and the plurality of markers;

determining a first set of projections of the plurality of markers on the first roentgenogram;

determining a first 3-D position of the x-ray source and a first 3-D position of the object with respect to the x-ray imager in the first orientation by satisfying following mathematical equations:

$$\begin{cases} (x-x0)*(Y0-y0) - (y-y0)*(X0-x0) = 0 \\ (x-x0)*(Z0-z0) - (z-z0)*(X0-x0) = 0 \\ (x-x1)*(Y1-y1) - (y-y1)*(X1-x1) = 0 \\ (x-x1)*(Z1-z1) - (z-z1)*(X1-x1) = 0 \\ (x-x2)*(Y2-y2) - (y-y2)*(X2-x2) = 0 \\ (x-x2)*(Z2-z2) - (z-z2)*(X2-x2) = 0 \\ (x-x3)*(Y3-y3) - (y-y3)*(X3-x3) = 0 \\ (x-x3)*(Z3-z3) - (z-z3)*(X3-x3) = 0 \\ (x0-x1)^2 - (y0-y1)^2 - (z0-z1)^2 - l01^2 = 0 \\ (x0-x2)^2 - (y0-y2)^2 - (z0-z2)^2 - l02^2 = 0 \\ (x0-x3)^2 - (y0-y3)^2 - (z0-z3)^2 - l03^2 = 0 \\ (x1-x2)^2 - (y1-y2)^2 - (z1-z2)^2 - l12^2 = 0 \\ (x1-x3)^2 - (y1-y3)^2 - (z1-z3)^2 - l13^2 = 0 \\ (x2-x3)^2 - (y2-y3)^2 - (z2-z3)^2 - l23^2 = 0 \end{cases}$$

wherein (x,y,z) are coordinates of the x-ray source, (x0,y0, z0) through (x3,y3,z3) are coordinates of the plurality of markers, (X0,Y0,Z0) through (X3,Y3,Z3) are coordinates of the first set of projections of the plurality of markers on the first roentgenogram, and l01, l02, l03, l04, 112, 113, 114, 123, 124, 134 are the predetermined distances between the plurality of markers to determine the distances between the plurality of markers and the first set of the projections of the plurality of markers on the first roentgenogram;

determining a second set of projections of the plurality of markers on the second roentgenogram;

determining a second 3-D position of the x-ray source and a second 3-D position of the object with respect to the x-ray imager in the second orientation by satisfying following mathematical equations:

$$\begin{cases} ('x-x0)*('Y0-y0)-('y-y0)*('X0-x0)=0 \\ ('x-x0)*('Z0-z0)-('z-z0)*('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-y2)-('y-y2)*('X2-x2)=0 \\ ('x-x2)*('Z1-z2)-('z-z2)*('X2-x2)=0 \\ ('x-x3)*('Y3-y3)-('y-y3)*('X3-x3)=0 \\ ('x-x3)*('Z3-z3)-('z-z3)*('X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein ('x,'y,'z) are coordinates of the x-ray source, (x0, y0,z0) through (x3,y3,z3) are coordinates of the plurality of markers, ('X0,'Y0,'Z0) through ('X3,'Y3,'Z3) are coordinates of the second set of projections of the plurality of markers on the second roentgenogram, and l01, l02, l03, l04, 112, 113, 114, 123, 124, 134 are the predetermined distances between the plurality of markers to determine the distances between the plurality of markers and the second set of projections of the plurality of markers on the second roentgenogram;

aligning the first and second 3-D object projections in a 3-D reference frame using the 3-D positions of the plurality of markers with respect to the x-ray imager in the first and second orientations; and creating a 3-D model of the imaged body part in the 3-D reference frame based on the first and second 3-D object projections.

28. A computer code segment operable to cause a computer to perform the following steps:

receive a first roentgenogram of the body part and the object disposed between an x-ray source and an x-ray imager in a first orientation, wherein the first roentgenogram includes an image of:
the body part,
the object, and
the plurality of markers;

receive a second roentgenogram of the body part and the object disposed between the x-ray source and the x-ray imager in a second orientation, wherein the second roentgenogram includes an image of:
the body part,
the object, and
the plurality of markers;

determine a first set of projections of the plurality of markers on the first roentgenogram;

determine a first 3-D position of the x-ray source and a first 3-D position of the object with respect to the x-ray imager in the first orientation by satisfying following mathematical equations:

$$\begin{cases} (x-x0)*(Y0-y0)-(y-y0)*(X0-x0)=0 \\ (x-x0)*(Z0-z0)-(z-z0)*(X0-x0)=0 \\ (x-x1)*(Y1-y1)-(y-y1)*(X1-x1)=0 \\ (x-x1)*(Z1-z1)-(z-z1)*(X1-x1)=0 \\ (x-x2)*(Y2-y2)-(y-y2)*(X2-x2)=0 \\ (x-x2)*(Z1-z2)-(z-z2)*(X2-x2)=0 \\ (x-x3)*(Y3-y3)-(y-y3)*(X3-x3)=0 \\ (x-x3)*(Z3-z3)-(z-z3)*(X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein (x,y,z) are coordinates of the x-ray source, (x0,y0, z0) through (x3,y3,z3) are coordinates of the plurality of markers, (X0,Y0,Z0) through (X3,Y3,Z3) are coordinates of the first set of projections of the plurality of markers on the first roentgenogram, and l01, l02, l03, l04, 112, 113, 114, 123, 124, 134 are the predetermined distances between the plurality of markers to determine the distances between the plurality of markers and the first set of the projections of the plurality of markers on the first roentgenogram;

determine a second set of projections of the plurality of markers on the second roentgenogram;

determine a second 3-D position of the x-ray source and a second 3-D position of the object with respect to the x-ray imager in the second orientation by satisfying following mathematical equations:

$$\begin{cases} ('x-x0)*('Y0-y0)-('y-y0)*('X0-x0)=0 \\ ('x-x0)*('Z0-z0)-('z-z0)*('X0-x0)=0 \\ ('x-x1)*('Y1-y1)-('y-y1)*('X1-x1)=0 \\ ('x-x1)*('Z1-z1)-('z-z1)*('X1-x1)=0 \\ ('x-x2)*('Y2-y2)-('y-y2)*('X2-x2)=0 \\ ('x-x2)*('Z1-z2)-('z-z2)*('X2-x2)=0 \\ ('x-x3)*('Y3-y3)-('y-y3)*('X3-x3)=0 \\ ('x-x3)*('Z3-z3)-('z-z3)*('X3-x3)=0 \\ (x0-x1)^2-(y0-y1)^2-(z0-z1)^2-l01^2=0 \\ (x0-x2)^2-(y0-y2)^2-(z0-z2)^2-l02^2=0 \\ (x0-x3)^2-(y0-y3)^2-(z0-z3)^2-l03^2=0 \\ (x1-x2)^2-(y1-y2)^2-(z1-z2)^2-l12^2=0 \\ (x1-x3)^2-(y1-y3)^2-(z1-z3)^2-l13^2=0 \\ (x2-x3)^2-(y2-y3)^2-(z2-z3)^2-l23^2=0 \end{cases}$$

wherein ('x,'y,'z) are coordinates of the x-ray source, (x0,y0,z0) through (x3,y3,z3) are coordinates of the plurality of markers, ('X0,'Y0,'Z0) through ('X3,'Y3, 'Z3) are coordinates of the second set of projections of the plurality of markers on the second roentgenogram, and l01, l02, l03, l04, 112, 113, 114, 123, 124, 134 are the predetermined distances between the plurality of markers to determine the distances between the plurality of markers and the second set of projections of the plurality of markers on the second roentgenogram;

align the first and second 3-D object projections in a 3-D reference frame using the 3-D positions of the plurality of markers with respect to the x-ray imager in the first and second orientations; and create a 3-D model of the imaged body part in the 3-D reference frame based on the first and second 3-D object projections.

\* \* \* \* \*